United States Patent
Bass et al.

(10) Patent No.: US 11,255,843 B2
(45) Date of Patent: Feb. 22, 2022

(54) COMPOSITIONS AND METHODS FOR IDENTIFYING METABOLICALLY ACTIVE AGENTS

(71) Applicant: Northwestern University, Evanston, IL (US)

(72) Inventors: Joseph T. Bass, Winnetka, IL (US); Clara Bien Peek, Chicago, IL (US); Akihiko Taguchi, Chicago, IL (US); Mark Perelis, Evanston, IL (US); Biliana Marcheva, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/560,597

(22) Filed: Sep. 4, 2019

(65) Prior Publication Data

US 2019/0391133 A1    Dec. 26, 2019

Related U.S. Application Data

(63) Continuation of application No. 15/652,968, filed on Jul. 18, 2017, now abandoned.

(60) Provisional application No. 62/363,585, filed on Jul. 18, 2016.

(51) Int. Cl.
| | |
|---|---|
| *G01N 33/50* | (2006.01) |
| *C12N 5/071* | (2010.01) |
| *C07K 14/47* | (2006.01) |
| *C12Q 1/6897* | (2018.01) |
| *C12N 5/077* | (2010.01) |

(52) U.S. Cl.
CPC ....... *G01N 33/507* (2013.01); *C07K 14/4702* (2013.01); *C12N 5/0658* (2013.01); *C12N 5/0676* (2013.01); *C12Q 1/6897* (2013.01); *G01N 33/5061* (2013.01); *C12N 2510/00* (2013.01); *C12N 2510/04* (2013.01); *G01N 33/5005* (2013.01); *G01N 33/5008* (2013.01); *G01N 2333/62* (2013.01); *G01N 2800/042* (2013.01)

(58) Field of Classification Search
CPC ............. C12Q 1/6897; G01N 33/5061; G01N 33/507; G01N 2333/62; G01N 33/5005; G01N 33/5008; G01N 2800/042; C12N 5/0676; C12N 5/0658; C12N 2510/00; C12N 2510/04; C07K 14/4702

See application file for complete search history.

(56) References Cited

PUBLICATIONS

Nichols et al. Bioenergetic Profile Experiment using C2C12 Myoblast Cells. JOVE (2010), 46, e2511, 6 pages. (Year: 2010).*

Lysenkova et al. The first examples of chemical modification of oligomycin A. The Journal of Antibiotics (2010), 63, 17-22. (Year: 2010).*

Chatterjee et al. Brain and muscle Arnt-like 1 is a key regulator of myogenesis. Journal of Cell Science (2013), 126, 2213-2224. (Year: 2013).*

Delfel et al. Distribution of Rotenone and Deguelin in Tephrosia vogelii and Separation of Rotenoid-Rich Fractions. J. Agr. Food Chem. (1970), 18(3), 385-390. (Year: 1970).*

Balsalobre et al., A serum shockA18:A62 induces circadian gene expression in mammalian tissue culture cells. Cell. Jun. 12, 1998;93(6):929-37.

Benner et al., The transcriptional landscape of mouse beta cells compared to human beta cells reveals notable species differences in long non-coding RNA and protein-coding gene expression. BMC Genomics. Jul. 22, 2014;15:620.

Biden et al., The diverse roles of protein kinase C in pancreatic beta-cell function. Biochem Soc Trans. Oct. 2008;36(Pt 5):916-9.

Bonnefond et al., Rare MTNR1B variants impairing melatonin receptor 1B function contribute to type 2 diabetes. Nat Genet. Jan. 29, 2012;44(3):297-301.

Buxton et al., Adverse metabolic consequences in humans of prolonged sleep restriction combined with circadian disruption. Sci Transl Med. Apr. 11, 2012;4(129):129ra43.

Carninci et al., Genome-wide analysis of mammalian promoter architecture and evolution. Nat Genet. Jun. 2006;38(6):626-35.

Chen et al., SEC24A deficiency lowers plasma cholesterol through reduced PCSK9 secretion. Elife. Apr. 9, 2013;2:e00444.

Cooper et al., Comprehensive analysis of transcriptional promoter structure and function in 1% of the human genome. Genome Res. Jan. 2006;16(1):1-10.

Creyghton et al., Histone H3K27ac separates active from poised enhancers and predicts developmental state. Proc Natl Acad Sci U S A. Dec. 14, 2010;107(50):21931-6.

Dobin et al., STAR: Ultrafast universal RNA-seq aligner. Bioinformatics. Jan. 1, 2013;29(1):15-21.

Easom, CaM kinase II: A protein kinase with extraordinary talents germane to insulin exocytosis. Diabetes. Apr. 1999;48(4):675-84.

Fang et al., Circadian enhancers coordinate multiple phases of rhythmic gene transcription in vivo. Cell. Nov. 20, 2014;159(5):1140-1152.

Fujimoto et al., Piccolo, a Ca2+ sensor in pancreatic beta-cells. Involvement of cAMP-GEFII.Rim2. Piccolo complex in cAMP-dependent exocytosis. J Biol Chem. Dec. 27, 2002;277(52):50497-502.

Fukuda, Molecular cloning, expression, and characterization of a novel class of synaptotagmin (Syt XIV) conserved from Drosophila to humans. J Biochem. May 2003;133(5):641-9.

(Continued)

*Primary Examiner* — Sean C. Barron
(74) *Attorney, Agent, or Firm* — Casimir Jones, S.C.; David W. Staple

(57) ABSTRACT

The present invention relates to cells with altered cell cycle control. In particular, the present invention provides cells with altered cell cycle control and uses of such cells to identify metabolically active agents.

4 Claims, 55 Drawing Sheets

Specification includes a Sequence Listing.

(56) References Cited

PUBLICATIONS

Gen et al., Munc18-1 is a dynamically regulated PKC target during short-term enhancement of transmitter release. Elife. Feb. 11, 2014;3:e01715.

Gu et al., Direct evidence for the pancreatic lineage: NGN3+ cells are islet progenitors and are distinct from duct progenitors. Development. May 2002;129(10):2447-57.

Gu et al., Pancreatic beta cells require NeuroD to achieve and maintain functional maturity. Cell Metab. Apr. 7, 2010;11(4):298-310.

He et al., Nucleosome dynamics define transcriptional enhancers. Nat Genet. Apr. 2010;42(4):343-7.

Heintzman et al., Distinct and predictive chromatin signatures of transcriptional promoters and enhancers in the human genome. Nat Genet. Mar. 2007;39(3):311-8.

Heinz et al., Simple combinations of lineage-determining transcription factors prime cis-regulatory elements required for macrophage and B cell identities. Mol Cell. May 28, 2010;38(4):576-89.

Hoffman et al., Locus co-occupancy, nucleosome positioning, and H3K4me1 regulate the functionality of FOXA2-, HNF4A-, and PDX1-bound loci in islets and liver. Genome Res. Aug. 2010;20(8):1037-51.

Hutchison et al., Improved statistical methods enable greater sensitivity in rhythm detection for genome-wide data. PLoS Comput Biol. Mar. 20, 2015;11(3):e1004094.

Jedd et al., Two new Ypt GTPases are required for exit from the yeast trans-Golgi compartment. J Cell Biol. May 5, 1997;137(3):563-80.

Johnson et al., The hepatocyte circadian clock controls acetaminophen bioactivation through NADPH-cytochrome P450 oxidoreductase. Proc Natl Acad Sci U S A. Dec. 30, 2014;111(52):18757-62.

Kanehisa et al., Data, information, knowledge and principle: Back to metabolism in KEGG. Nucleic Acids Res. Jan. 2014;42(Database issue):D199-205.

Kang et al., Munc13-1 is required for the sustained release of insulin from pancreatic beta cells. Cell Metab. 3, 463-468 (2006).

Koike et al., Transcriptional architecture and chromatin landscape of the core circadian clock in mammals. Science. Oct. 19, 2012;338(6105):349-54.

Lamia et al., Physiological significance of a peripheral tissue circadian clock. Proc Natl Acad Sci USA. Sep. 30, 2008;105(39):15172-7.

Langmead et al., Ultrafast and memory-efficient alignment of short DNA sequences to the human genome. Genome Biol. 2009;10(3):R25.

Lee et al., Bmal1 and Beta-Cell Clock Are Required for Adaptation to Circadian Disruption, and Their Loss of Function Leads to Oxidative Stress-Induced Beta-Cell Failure in Mice. MCB. Jun. 2013;33(11):2327-2338.

Liu et al., The role of synaptobrevin1/VAMP1 in Ca2+-triggered neurotransmitter release at the mouse neuromuscular junction. J Physiol. Apr. 1, 2011;589(Pt 7):1603-18.

Love et al., Moderated estimation of fold change and dispersion for RNA-seq data with DESeq2. Genome Biol. 2014;15(12):550.

Marcheva et al., Disruption of the clock components CLOCK and BMAL1 leads to hypoinsulinaemia and diabetes. Nature. Jul. 29, 2010;466(7306):627-31.

Menet et al., Nascent-Seq reveals novel features of mouse circadian transcriptional regulation. Elife. Nov. 13, 2012;1:e00011.

Milochau et al., Synaptotagmin 11 interacts with components of the RNA-induced silencing complex RISC in clonal pancreatic β-cells. FEBS Lett. Jun. 27, 2014;588(14):2217-22.

Morris et al., Endogenous circadian system and circadian misalignment impact glucose tolerance via separate mechanisms in humans. Proc Natl Acad Sci U S A. Apr. 28, 2015;112(17):E2225-34.

Noble et al., A pseudoatomic model of the COPII cage obtained from cryo-electron microscopy and mass spectrometry. Nat Struct Mol Biol. Feb. 2013;20(2):167-73.

O'Neill et al., cAMP-dependent signaling as a core component of the mammalian circadian pacemaker. Science. May 16, 2008;320(5878):949-53.

Ogata et al., KEGG: Kyoto Encyclopedia of Genes and Genomes. Nucleic Acids Res. Jan. 1, 1999;27(1):29-34.

Ohara-Imaizumi et al., Correlation of syntaxin-1 and SNAP-25 clusters with docking and fusion of insulin granules analysed by total internal reflection fluorescence microscopy. Diabetologia. Dec. 2004;47(12):2200-7.

Pasquali et al., Pancreatic islet enhancer clusters enriched in type 2 diabetes risk-associated variants. Nat Genet. Feb. 2014;46(2):136-143.

Peek et al., Circadian clock NAD+ cycle drives mitochondrial oxidative metabolism in mice.Science. Nov. 1, 2013;342(6158):1243417.

Preitner et al., The orphan nuclear receptor REV-ERBα controls circadian transcription within the positive limb of the mammalian circadian oscillator. Cell. Jul. 26, 2002;110(2):251-60.

Pulimeno et al., Autonomous and self-sustained circadian oscillators displayed in human islet cells. Diabetologia. Mar. 2013;56(3):497-507.

Rey et al., Genome-wide and phase-specific DNA-binding rhythms of BMAL1 control circadian output functions in mouse liver. PLoS Biol. Feb. 2011;9(2):e1000595.

Sadacca et al., An intrinsic circadian clock of the pancreas is required for normal insulin release and glucose homeostasis in mice. Diabetologia. Jan. 2011;54(1):120-4.

Stoffers et al., Pancreatic agenesis attributable to a single nucleotide deletion in the human IPF1 gene coding sequence. Nat Genet. Jan. 1997;15(1):106-10.

Takahashi et al., Role of Epac2A/Rap1 signaling in interplay between incretin and sulfonylurea in insulin secretion. Diabetes. Apr. 2015;64(4):1262-72.

Turek et al., Obesity and metabolic syndrome in circadian Clock mutant mice. Science. May 13, 2005;308(5724):1043-5.

Ueda et al., System-level identification of transcriptional circuits underlying mammalian circadian clocks. Nat Genet. Feb. 2005;37(2):187-92.

Vollmers et al., Circadian oscillations of protein-coding and regulatory RNAs in a highly dynamic mammalian liver epigenome. Cell Metab. Dec. 5, 2012;16(6):833-45.

Wang et al., Mechanisms of biphasic insulin-granule exocytosis—roles of the cytoskeleton, small GTPases and SNARE proteins. J Cell Sci. Apr. 1, 2009;122(Pt 7):893-903.

Yoo et al., PERIOD2:LUCIFERASE real-time reporting of circadian dynamics reveals persistent circadian oscillations in mouse peripheral tissues. Proc Natl Acad Sci U S A. Apr. 13, 2004;101(15):5339-46.

Zamir et al., A nuclear hormone receptor corepressor mediates transcriptional silencing by receptors with distinct repression domains. Mol Cell Biol. Oct. 1996;16(10):5458-65.

Zhang et al., Membrane association and functional regulation of Sec3 by phospholipids and Cdc42. J Cell Biol. Jan. 14, 2008;180(1):145-58.

* cited by examiner

FIG. 18

AGCGCCCAATACGCAAACCGCCTCTCCCCGCGCGTTGGCCGATTCA
TTAATGCAGCTGGCACGACAGGTTTCCCGACTGGAAAGCGGGCAG
TGAGCGCAACGCAATTAATGTGAGTTAGCTCACTCATTAGGCACCC
CAGGCTTTACACTTTATGCTTCCGGCTCGTATGTTGTGTGGAATTG
TGAGCGGATAACAATTTCACACAGGAAACAGCTATGACCATGATTA
CGCCAAGCTTCAGGGACAGGCCAAAAGTCTGTTACATCTAGCCAG
GTCCTGGTTGGTCCAAGAATATGTCAGTACAGATTGCCTCCATCAG
ACAGAAGTGATGGCCTCAGCAGGCCACACGGTGGCTGCTCACAGG
CTGCAGAGGCACTGGCTGTGGGACCCGAGTGCTCTATGGCTGTTT
GGGTGCTGGGTTATTCCAACCCTCTACCTCCCTTCTTCCTCCTCTTA
TCCACATCCACCAAACCTGGTCGTCTGGAATCTAAAGAACAACCAG
GAAAAATAAGCAATTCAGTTTCTTGTGAAGGACAATTGCCATTTG
TTTTTCCTTAAAAGATGGGGTAAGCATCAAAAACAAATAAATGAAA
ACTACAAATCAGCTACCTAATTCACCTTTTGGGGAGGACTTTTAGT
ATAAAAGTCTAAATTTCCCATGTCAGAGAATATTGGAAGCAGTCAC
AACTCAGTTTTTTGTTTGTTTGTTTGTTTTTTGAGACAGGGTTTCTT
TTTATAGCCCTGGCTGTCCTGGAACTCACTTTGTAGACCAGGCTGG
CCTTGAACTCAGAAATCCACCTGCCTCTGCCTCCTGAGTGCTGGGA
TTAAAGGCATGCACCACCAAGCCCAGCAACTCAGTTATTTTATCA
ACGTTGTTTCGATGCTCGTGTACATCTCAGATGAATCCATTCTCTTT
CCCATGTTCAGGGAGGCCCACAGTCAGATTGAAAAGAGGCGTCGG
GACAAAATGAACAGTTTCATTGATGAATTGGCTTCTTTGGTACTAG
TAACGGCCGCCAGTGTGCTGGAATTCGCCCTT

TGTGTCAGTTAGGGTGTGGAAAGTCCCCAGGCTCCCCAGCAGGCA
GAAGTATGCAAAGCATGCATCTCAATTAGTCAGCAACCAGGTGTGG
AAAGTCCCCAGGCTCCCCAGCAGGCAGAAGTATGCAAAGCATGCA
TCTCAATTAGTCAGCAACCATAGTCCCGCCCCTAACTCCGCCCATC
CCGCCCCTAACTCCGCCCAGTTCCGCCCATTCTCCGCCCCATGGCT
GACTAATTTTTTTATTTATGCAGAGGCCGAGGCCGCCTCTGCCTC
TGAGCTATTCCAGAAGTAGTGAGGAGGCTTTTTTGGAGGCCTAGGC
TTTTGCAAAAAGCTCCCGGGAGCTTGTATATCCATTTTCGGATCTG
ATCAAGAGACAGGATGAGGATCGTTTCGCATGATTGAACAAGATG
GATTGCACGCAGGTTCTCCGGCCGCTTGGGTGGAGAGGCTATTCG
GCTATGACTGGGCACAACAGACAATCGGCTGCTCTGATGCCGCCG
TGTTCCGGCTGTCAGCGCAGGGGCGCCCGGTTCTTTTTGTCAAGAC
CGACCTGTCCGGTGCCCTGAATGAACTGCAGGACGAGGCAGCGCG
GCTATCGTGGCTGGCCACGACGGGCGTTCCTTGCGCAGCTGTGCT
CGACGTTGTCACTGAAGCGGGAAGGGACTGGCTGCTATTGGGCGA
AGTGCCGGGGCAGGATCTCCTGTCATCTCACCTTGCTCCTGCCGAG
AAAGTATCCATCATGGCTGATGCAATGCGGCGGCTGCATACGCTTG
ATCCGGCTACCTGCCCATTCGACCACCAAGCGAAACATCGCATCGA
GCGAGCACGTACTCGGATGGAAGCCGGTCTTGTCGATCAGGATGA
TCTGGACGAAGAGCATCAGGGGCTCGCGCCAGCCGAACTGTTCGC
CAGGCTCAAGGCGCGCATGCCCGACGGCGAGGATCTCGTCGTGAC
CCATGGCGATGCCTGCTTGCCGAATATCATGGTGGAAAATGGCCG
CTTTTCTGGATTCATCGACTGTGGCCGGCTGGGTGTGGCGGACCG
CTATCAGGACATAGCGTTGGCTACCCGTGATATTGCTGAAGAGCTT
GGCGGCGAATGGGCTGACCGCTTCCTCGTGCTTTACGGTATCGCC
GCTCCCGATTCGCAGCGCATCGCCTTCTATCGCCTTCTTGACGAGT
TCTTCTGAGCGGGACTCTGGGGTTCGAAacgttactggccgaagccgcttggaata
aggccggtgtgcgtttgtctatatgttattttccaccatattgccgtcttttggcaatgtgagggcccggaaacctg

FIG. 18 (cont.)

gccctgtcttcttgacgagcattcctaggggtctttcccctctcgccaaaggaatgcaaggtctgttgaatgtcgt
gaaggaagcagttcctctggaagcttcttgaagacaaacaacgtctgtagcgacccttttgcaggcagcggaac
cccccacctggcgacaggtgcctctgcggccaaaagccacgtgtataagatacacctgcaaaggcggcacaa
ccccagtgccacgttgtgagttggatagttgtggaaagagtcaaatggctctcctcaagcgtattcaacaaggg
gctgaaggatgcccagaaggtaccccattgtatgggatctgatctggggcctcggtgcacatgctttacatgtgt
ttagtcgaggttaaaaaaacgtctaggcccccccgaaccacggggacgtggttttcctttgaaaaacacgataat
accatggtgagcaagggcgaggaggataacatggccatcatcaaggagttcatgcgcttcaaggtgcacatg
gagggctccgtgaacggccacgagttcgagatcgagggcgagggcgagggccgcccctacgagggcaccca
gaccgccaagctgaaggtgaccaagggtggccccctgcccttcgcctgggacatcctgtcccctcagttcatgt
acggctccaaggcctacgtgaagcaccccgccgacatccccgactacttgaagctgtccttccccgagggcttc
aagtgggagcgcgtgatgaacttcgaggacggcggcgtggtgaccgtgacccaggactcctccctgcaggac
ggcgagttcatctacaaggtgaagctgcgcggcaccaacttccctccgacggccccgtaatgcagaagaaga
cgatgggctgggaggcctcctccgagcggatgtaccccgaggacggcgccctgaagggcgagatcaagcag
aggctgaagctgaaggacggcggccactacgacgctgaggtcaagaccacctacaaggccaagaagcccgt
gcagctgcccggcgcctacaacgtcaacatcaagttggacatcacctcccacaacgaggactacaccatcgtg
gaacagtacgaacgcgcgagggccgccactccaccggcggcatggacgagctgtacaagtaaTTCGA
ATGACCGACCAAGCGACGCCCAACCTGCCATCACGAGATTTCGAT
TCCACCGCCGCCTTCTATGAAAGGTTGGGCTTCGGAATCGTTTTCC
GGGACGCCGGCTGGATGATCCTCCAGCGCGGGGATCTCATGCTGG
AGTTCTTCGCCCACCCCAACTTGTTTATTGCAGCTTATAATGGTTAC
AAATAAAGCAATAGCATCACAAATTTCACAAATAAAGCATTTTTTC
ACTGCATTCTAGTTGTGGTTTGTCCAAACTCATCAATGTATCTTATC
ATGTCTGTATACC AAGGGCGAATTCTGCAGATATCCATCACACTGGCGGCCGCTCGAG
ATGGCTGTTCAGCACATGAAAACTTTGAGAGGTAAGAGCTCAGGCT
TTATTGCCTATATGCCCTTGACTACAGGTATGACCACTCTTGCCTA
CACTGTCCCTGACACAAATGTTGATTTCTTTCAACACGTAACCCTA
AGTGACAGGCCTGTACATCTTGGCAGAAGATAGGGGGCCGAATCA
GGTTGTTAATGAGCTGATGTGGGTATTAAGATGTCATTTGCACTAA
TACTTCCCCAGAGCAGATAAGCAGATGAGCTCAGATACTTCTCTGT
GTACATAGCATATATACATTGACATATTCCTGTTTACCAAAGAGGA
CAGACACCTCTCATGTCCTCTTGCCTGTGCCTGGATCCCACCCCTT
GCAATGATCAAAATCAAGAAATGTGGGCGCACACAGGGAGGCAGG
AAAGAGCCTCCAACTTCTAAGAGAAAAACTTACCCTGGTTCCTCTG
ATGAATGAGTCACAGGTGGAGAGTTGTATCATCAGAAATGAACATT
GATGATATTTTCATCTTCTTGGAATTTTCCCGAACTAGATTGACTCT
CTGTGAGGGAGGCAGTATTTTCCTTCTTTGCTAAGTGTGGGGAGGG
TGAGAAAACAGAGGCAGGAAACTGGAAGTAACTTTATCAAACTGCA
GGAGGAATCTGAAATACATCACCCATTTTGGTGAATGTCGTTCCTG
GAATTTTCCAGTTAGTCTTGGGCTTTGGGACAAACTTGGGAAGGGT
GCTTGGCCCCATATGACCTACATGGTGAGAGAGGCATCCCTTCTAG
AGGGCCCAATTCGCCCTATAGTGAGTCGTATTACAATTCACTGGCC
GTCGTTTTACAACGTCGTGACTGGGAAAACCCTGGCGTTACCCAAC
TTAATCGCCTTGCAGCACATCCCCCTTTCGCCAGCTGGCGTAATAG
CGAAGAGGCCCGCACCGATCGCCCTTCCCAACAGTTGCGCAGCCT
GAATGGCGAATGGACGCGCCCTGTAGCGGCGCATTAAGCGCGGCG
GGTGTGGTGGTTACGCGCAGCGTGACCGCTACACTTGCCAGCGCC
CTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGG

FIG. 18 (cont.)

```
TTCCGATTTAGTGCTTTACGGCACCTCGACCCCAAAAAACTTGATT
AGGGTGATGGTTCACGTAGTGGGCCATCGCCCTGATAGACGGTTTT
TCGCCCTTTGACGTTGGAGTCCACGTTCTTTAATAGTGGACTCTTG
TTCCAAACTGGAACAACACTCAACCCTATCTCGGTCTATTCTTTTGA
TTTATAAGGGATTTTGCCGATTTCGGCCTATTGGTTAAAAAATGAG
CTGATTTAACAAAAATTTAACGCGAATTTTAACAAAATTCAGGGCG
CAAGGGCTGCTAAAGGAAGCGGAACACGTAGAAAGCCAGTCCGCA
GAAACGGTGCTGACCCCGGATGAATGTCAGCTACTGGGCTATCTG
GACAAGGGAAAACGCAAGCGCAAAGAGAAAGCAGGTAGCTTGCAG
TGGGCTTACATGGCGATAGCTAGACTGGGCGGTTTTATGGACAGC
AAGCGAACCGGAATTGCCAGCTGGGGCGCCCTCTGGTAAGGTTGG
GAAGCCCTGCAAAGTAAACTGGATGGCTTTCTTGCCGCCAAGGATC
TGATGGCGCAGGGGATCAAGATCTGATCAAGAGACAGGATGAGGA
TCGTTTCGCATGATTGAACAAGATGGATTGCACGCAGGTTCTCCGG
CCGCTTGGGTGGAGAGGCTATTCGGCTATGACTGGGCACAACAGA
CAATCGGCTGCTCTGATGCCGCCGTGTTCCGGCTGTCAGCGCAGG
GGCGCCCGGTTCTTTTTGTCAAGACCGACCTGTCCGGTGCCCTGAA
TGAACTGCAGGACGAGGCAGCGCGGCTATCGTGGCTGGCCACGAC
GGGCGTTCCTTGCGCAGCTGTGCTCGACGTTGTCACTGAAGCGGG
AAGGGACTGGCTGCTATTGGGCGAAGTGCCGGGGCAGGATCTCCT
GTCATCCCACCTTGCTCCTGCCGAGAAAGTATCCATCATGGCTGAT
GCAATGCGGCGGCTGCATACGCTTGATCCGGCTACCTGCCCATTCG
ACCACCAAGCGAAACATCGCATCGAGCGAGCACGTACTCGGATGG
AAGCCGGTCTTGTCGATCAGGATGATCTGGACGAAGAGCATCAGG
GGCTCGCGCCAGCCGAACTGTTCGCCAGGCTCAAGGCGCGCATGC
CCGACGGCGAGGATCTCGTCGTGACCCATGGCGATGCCTGCTTGC
CGAATATCATGGTGGAAAATGGCCGCTTTTCTGGATTCATCGACTG
TGGCCGGCTGGGTGTGGCGGACCGCTATCAGGACATAGCGTTGGC
TACCCGTGATATTGCTGAAGAGCTTGGCGGCGAATGGGCTGACCG
CTTCCTCGTGCTTTACGGTATCGCCGCTCCCGATTCGCAGCGCATC
GCCTTCTATCGCCTTCTTGACGAGTTCTTCTGAATTGAAAAAGGAA
GAGTATGAGTATTCAACATTTCCGTGTCGCCCTTATTCCCTTTTTG
CGGCATTTTGCCTTCCTGTTTTTGCTCACCCAGAAACGCTGGTGAA
AGTAAAAGATGCTGAAGATCAGTTGGGTGCACGAGTGGGTTACAT
CGAACTGGATCTCAACAGCGGTAAGATCCTTGAGAGTTTTCGCCCC
GAAGAACGTTTTCCAATGATGAGCACTTTTAAAGTTCTGCTATGTG
GCGCGGTATTATCCCGTATTGACGCCGGGCAAGAGCAACTCGGTC
GCCGCATACACTATTCTCAGAATGACTTGGTTGAGTACTCACCAGT
CACAGAAAAGCATCTTACGGATGGCATGACAGTAAGAGAATTATGC
AGTGCTGCCATAACCATGAGTGATAACACTGCGGCCAACTTACTTC
TGACAACGATCGGAGGACCGAAGGAGCTAACCGCTTTTTTGCACAA
CATGGGGGATCATGTAACTCGCCTTGATCGTTGGGAACCGGAGCT
GAATGAAGCCATACCAAACGACGAGCGTGACACCACGATGCCTGT
AGCAATGGCAACAACGTTGCGCAAACTATTAACTGGCGAACTACTT
ACTCTAGCTTCCCGGCAACAATTAATAGACTGGATGGAGGCGGATA
AAGTTGCAGGACCACTTCTGCGCTCGGCCCTTCCGGCTGGCTGGTT
TATTGCTGATAAATCTGGAGCCGGTGAGCGTGGGTCTCGCGGTATC
ATTGCAGCACTGGGGCCAGATGGTAAGCCCTCCCGTATCGTAGTTA
TCTACACGACGGGGAGTCAGGCAACTATGGATGAACGAAATAGAC
AGATCGCTGAGATAGGTGCCTCACTGATTAAGCATTGGTAACTGTC
```

FIG. 18 (cont.)

AGACCAAGTTTACTCATATATACTTTAGATTGATTTAAAACTTCATT
TTTAATTTAAAAGGATCTAGGTGAAGATCCTTTTTGATAATCTCATG
ACCAAAATCCCTTAACGTGAGTTTTCGTTCCACTGAGCGTCAGACC
CCGTAGAAAAGATCAAAGGATCTTCTTGAGATCCTTTTTTTCTGCG
CGTAATCTGCTGCTTGCAAACAAAAAAACCACCGCTACCAGCGGTG
GTTTGTTTGCCGGATCAAGAGCTACCAACTCTTTTTCCGAAGGTAA
CTGGCTTCAGCAGAGCGCAGATACCAAATACTGTTCTTCTAGTGTA
GCCGTAGTTAGGCCACCACTTCAAGAACTCTGTAGCACCGCCTACA
TACCTCGCTCTGCTAATCCTGTTACCAGTGGCTGCTGCCAGTGGCG
ATAAGTCGTGTCTTACCGGGTTGGACTCAAGACGATAGTTACCGGA
TAAGGCGCAGCGGTCGGGCTGAACGGGGGGTTCGTGCACACAGCC
CAGCTTGGAGCGAACGACCTACACCGAACTGAGATACCTACAGCG
TGAGCTATGAGAAAGCGCCACGCTTCCCGAAGGGAGAAAGGCGGA
CAGGTATCCGGTAAGCGGCAGGGTCGGAACAGGAGAGCGCACGAG
GGAGCTTCCAGGGGGAAACGCCTGGTATCTTTATAGTCCTGTCGG
GTTTCGCCACCTCTGACTTGAGCGTCGATTTTGTGATGCTCGTCA
GGGGGGCGGAGCCTATGGAAAAACGCCAGCAACGCGGCCTTTTTA
CGGTTCCTGGCCTTTTGCTGGCCTTTTGCTCACATGTTCTTTCCTGC
GTTATCCCCTGATTCTGTGGATAACCGTATTACCGCCTTTGAGTGA
GCTGATACCGCTCGCCGCAGCCGAACGACCGAGCGCAGCGAGTCA
GTGAGCGAGGAAGCGGAAG

FIG. 26B

| # | Compound | % | Targets | Function |
|---|---|---|---|---|
| 1 | Suloctidil | 242.9 | β adrenergic receptor, acidic phospholipids | Vasodilator |
| 2 | Alexidine hydrochloride | 168.7 | ERK2, acidic phospholipids | Mouthwash |
| 3 | Tomatine | 116.6 | Acetylcholinesterase | Plant antifungal/antibacterial |
| 4 | Benzalkonium chloride | 53.6 | M3R, PLA2 | Preservative in Visine eye drops |
| 5 | Clofibric acid | 48.9 | PPARα, PPARγ, PPARδ | Hypoglycemic agent |
| 6 | Rhodinyl acetate | 45.0 | TRPV1, TRPM8, ASIC, AMPA receptor | Antinociceptive; scent |
| 7 | Pilocarpine nitrate | 39.1 | M3R | Muscarinic agonist used in glaucoma |
| 8 | Trihexyphenidyl hydrochloride | 38.8 | M1R | Muscarinic antagonist |
| 9 | Dyclonine hydrochloride | 37.1 | Histamine H3R, acetylcholinesterase | Oral anaesthetic |
| 10 | Desoxycorticosterone acetate | 36.8 | Glucocorticoid receptor, androgen receptor | Mineralocorticoid |
| 11 | Ketoprofen | 34.9 | 5-HT1, 5-HT2, 5-HT3, 5-HT5, 5-HT7 receptors | Antinociceptive |
| 12 | Triamcinolone diacetate | 34.7 | Glucocorticoid receptor | Glucocorticoid |
| 13 | Isoetharine mesylate | 34.4 | β adrenergic receptor | Bronchodilator |
| 14 | Carbachol | 34.0 | M3R | Muscarinic and nicotinic agonist |
| 15 | Mecamylamine hydrochloride | 31.4 | Nicotinic acetylcholine receptor, NMDA receptor | Antihypertensive |
| 16 | Dehydrocholic acid | 31.1 | G coupled bile acid receptor 1, steroid-5-α-reductase | Hydrochloretic |
| 17 | Tacrine hydrochloride | 31.1 | Acetylcholinesterase | Acetylcholinesterase inhibitor, Alzheimer's associated dementia |
| 18 | Piperine | 30.9 | TRPV1, CYP450, Aryl hydrocarbon hydroxylase | Black pepper; enhances drug bioavailability |
| 19 | Ivermectin | 29.8 | Glycine gated chloride channel | Antihelmintic; round worm infection |
| 20 | Pipamperone | 26.4 | 5-HT2, Dopamine D4 receptors | Sedative; chronic psychosis |
| 21 | Ropinirole | 21.3 | 5-HT2a, D2, D3, D4 receptors | Parkinson's disease; neuroprotective; dopamine agonist |
| 22 | Colforsin | 21.1 | Adenyl cyclase | Water soluble forskolin derivative |
| 23 | Camylofine dihydrochloride | 16.3 | PDE4 | Cervical dilator; phosphodiesterase inhibitor |

SEQUENCE LISTING

<160> NUMBER OF SEQ ID NOS: 25

<210> SEQ ID NO 1
<211> LENGTH: 8219
<212> TYPE: DNA
<213> ORGANISM: Artificial sequence
<220> FEATURE:
<223> OTHER INFORMATION: Synthetic

<400> SEQUENCE: 1

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttc     240
agggacaggc caaaagtctg ttacatctag ccaggtcctg gttggtccaa gaatatgtca     300
gtacagattg cctccatcag acagaagtga tggcctcagc aggccacacg gtggctgctc     360
acaggctgca gaggcactgg ctgtgggacc cgagtgctct atggctgttt tgggtgctgg     420
gttattccaa ccctctacct cccttcttcc tcctcttatc cacatccacc aaacctggtc     480
gtctggaatc taaagaacaa ccaggaaaaa taagcaattc agtttcttgt gaaaggacaa     540
```

```
ttgccatttg ttttttcctta aaagatgggg taagcatcaa aaacaaataa atgaaaacta    600
caaatcagct acctaattca ccttttgggg aggacttta gtataaaagt ctaaatttcc      660
catgtcagag aatattggaa gcagtcacaa ctcagttttt tgtttgtttg tttgttttt      720 gagacagggt ttcttttat agccctggct gtcctggaac tcactttgta gaccaggctg      780
gccttgaact cagaaatcca cctgcctctg cctcctgagt gctgggatta aaggcatgca    840
ccaccaagcc cagcaactca gttattttta tcaacgttgt ttcgatgctc gtgtacatct    900
cagatgaatc cattctcttt cccatgttca gggaggccca cagtcagatt gaaaagaggc    960
gtcgggacaa aatgaacagt ttcattgatg aattggcttc tttggtacta gtaacggccg   1020
ccagtgtgct ggaattcgcc ctttgtgtca gttagggtgt ggaaagtccc caggctcccc   1080
agcaggcaga agtatgcaaa gcatgcatct caattagtca gcaaccaggt gtggaaagtc   1140
cccaggctcc ccagcaggca gaagtatgca aagcatgcat ctcaattagt cagcaaccat   1200
agtcccgccc ctaactccgc ccatcccgcc cctaactccg cccagttccg cccattctcc   1260
gccccatggc tgactaattt ttttattta tgcagaggcc gaggccgcct ctgcctctga    1320
gctattccag aagtagtgag gaggcttttt tggaggccta ggcttttgca aaaagctccc   1380
gggagcttgt atatccattt tcggatctga tcaagagaca ggatgaggat cgtttcgcat   1440
gattgaacaa gatggattgc acgcaggttc tccggccgct tgggtggaga ggctattcgg   1500
ctatgactgg gcacaacaga caatcggctg ctctgatgcc gccgtgttcc ggctgtcagc   1560
gcaggggcgc ccggttcttt ttgtcaagac cgacctgtcc ggtgccctga tgaactgca    1620 ggacgaggca gcgcggctat cgtggctggc cacgacgggc gttccttgcg cagctgtgct   1680
cgacgttgtc actgaagcgg gaagggactg gctgctattg ggcgaagtgc cggggcagga   1740
tctcctgtca tctcaccttg ctcctgccga gaaagtatcc atcatggctg atgcaatgcg   1800
gcggctgcat acgcttgatc cggctacctg cccattcgac caccaagcga aacatcgcat   1860
cgagcgagca cgtactcgga tggaagccgg tcttgtcgat caggatgatc tggacgaaga   1920
gcatcagggg ctcgcgccag ccgaactgtt cgccaggctc aaggcgcgca tgcccgacgg   1980
cgaggatctc gtcgtgaccc atggcgatgc ctgcttgccg aatatcatgg tggaaaatgg   2040
ccgcttttct ggattcatcg actgtggccg gctgggtgtg gcggaccgct atcaggacat   2100
agcgttggct acccgtgata ttgctgaaga gcttggcggc gaatgggctg accgcttcct   2160
cgtgctttac ggtatcgccg ctcccgattc gcagcgcatc gccttctatc gccttcttga   2220
cgagttcttc tgagcgggac tctggggttc gaaacgttac tggccgaagc cgcttggaat   2280
aaggccggtg tgcgtttgtc tatatgttat tttccaccat attgccgtct tttggcaatg   2340
tgagggcccg gaaacctggc cctgtcttct tgacgagcat tcctaggggt ctttcccctc   2400
tcgccaaagg aatgcaaggt ctgttgaatg tcgtgaagga agcagttcct ctggaagctt   2460
cttgaagaca acaacgtct gtagcgaccc tttgcaggca gcggaacccc ccacctggcg   2520
acaggtgcct ctgcggccaa aagccacgtg tataagatac acctgcaaag gcggcacaac   2580
cccagtgcca cgttgtgagt tggatagttg tggaaagagt caaatggctc tcctcaagcg   2640
tattcaacaa gggctgaag gatgcccaga aggtacccca ttgtatggga tctgatctgg   2700
ggcctcggtg cacatgcttt acatgtgttt agtcgaggtt aaaaaaacgt ctaggccccc   2760
cgaaccacgg ggacgtggtt ttcctttgaa aaacacgata taccatggt gagcaagggc    2820 gaggaggata acatggccat catcaaggag ttcatgcgct tcaaggtgca catggagggc   2880
tccgtgaacg gccacgagtt cgagatcgag ggcgagggcg agggccgccc ctacgagggc   2940
```

```
acccagaccg ccaagctgaa ggtgaccaag ggtggccccc tgcccttcgc ctgggacatc    3000
ctgtcccctc agttcatgta cggctccaag gcctacgtga agcaccccgc cgacatcccc    3060
gactacttga agctgtcctt ccccgagggc ttcaagtggg agcgcgtgat gaacttcgag    3120
gacggcggcg tggtgaccgt gacccaggac tcctccctgc aggacggcga gttcatctac    3180
aaggtgaagc tgcgcggcac caacttcccc tccgacggcc ccgtaatgca gaagaagacg    3240
atgggctggg aggcctcctc cgagcggatg taccccgagg acggcgccct gaagggcgag    3300
atcaagcaga ggctgaagct gaaggacggc ggccactacg acgctgaggt caagaccacc    3360
tacaaggcca agaagcccgt gcagctgccc ggcgcctaca acgtcaacat caagttggac    3420
atcacctccc acaacgagga ctacaccatc gtggaacagt acgaacgcgc cgagggccgc    3480
cactccaccg gcggcatgga cgagctgtac aagtaattcg aaatgaccga ccaagcgacg    3540
cccaacctgc catcacgaga tttcgattcc accgccgcct tctatgaaag gttgggcttc    3600
ggaatcgttt tccgggacgc cggctggatg atcctccagc gcggggatct catgctggag    3660
ttcttcgccc accccaactt gtttattgca gcttataatg ttacaaata aagcaatagc     3720 atcacaaatt tcacaaataa agcatttttt tcactgcatt ctagttgtgg tttgtccaaa    3780
ctcatcaatg tatcttatca tgtctgtata ccaagggcga attctgcaga tatccatcac    3840
actggcggcc gctcgagatg gctgttcagc acatgaaaac tttgagaggt aagagctcag    3900
gctttattgc ctatatgccc ttgactacag gtatgaccac tcttgcctac actgtccctg    3960
acacaaatgt tgatttcttt caacacgtaa ccctaagtga caggcctgta catcttggca    4020
gaagataggg ggccgaatca ggttgttaat gagctgatgt gggtattaag atgtcatttg    4080
cactaatact tccccagagc agataagcag atgagctcag atacttctct gtgtacatag    4140
catatataca ttgacatatt cctgtttacc aaagaggaca gacacctctc atgtcctctt    4200
gcctgtgcct ggatcccacc ccttgcaatg atcaaaatca agaaatgtgg gcgcacacag    4260
ggaggcagga aagagcctcc aacttctaag agaaaaactt accctggttc ctctgatgaa    4320
tgagtcacag gtggagagtt gtatcatcag aaatgaacat tgatgatatt ttcatcttct    4380
tggaattttc ccgaactaga ttgactctct gtgagggagg cagtattttc cttctttgct    4440
aagtgtgggg agggtgagaa aacagaggca ggaaactgga agtaacttta tcaaactgca    4500
ggaggaatct gaaatacatc acccattttg gtgaatgtcg ttcctggaat tttccagtta    4560
gtcttgggct ttgggacaaa cttgggaagg gtgcttggcc ccatatgacc tacatggtga    4620
gagaggcatc ccttctagag ggcccaattc gccctatagt gagtcgtatt acaattcact    4680
ggccgtcgtt ttacaacgtc gtgactggga aaaccctggc gttacccaac ttaatcgcct    4740
tgcagcacat ccccctttcg ccagctggcg taatagcgaa gaggcccgca ccgatcgccc    4800
ttcccaacag ttgcgcagcc tgaatggcga atggacgcgc cctgtagcgg cgcattaagc    4860
gcggcgggtg tggtggttac gcgcagcgtg accgctacac ttgccagcgc cctagcgccc    4920
gctcctttcg ctttcttccc ttcctttctc gccacgttcg ccggctttcc ccgtcaagct    4980
ctaaatcggg ggctcccttt agggttccga tttagtgctt tacggcacct cgaccccaaa    5040
aaacttgatt agggtgatgg ttcacgtagt gggccatcgc cctgatagac ggtttttcgc    5100
cctttgacgt tggagtccac gttctttaat agtggactct tgttccaaac tggaacaaca    5160
ctcaacccta tctcggtcta ttcttttgat ttataaggga ttttgccgat ttcggcctat    5220
tggttaaaaa atgagctgat ttaacaaaaa tttaacgcga attttaacaa aattcagggc    5280
```

```
gcaagggctg ctaaaggaag cggaacacgt agaaagccag tccgcagaaa cggtgctgac    5340
cccggatgaa tgtcagctac tgggctatct ggacaaggga aaacgcaagc gcaaagagaa    5400
agcaggtagc ttgcagtggg cttacatggc gatagctaga ctgggcggtt ttatggacag    5460
caagcgaacc ggaattgcca gctgggcgc cctctggtaa ggttgggaag ccctgcaaag     5520
taaactggat ggctttcttg ccgccaagga tctgatggcg caggggatca agatctgatc    5580
aagagacagg atgaggatcg tttcgcatga ttgaacaaga tggattgcac gcaggttctc    5640
cggccgcttg ggtggagagg ctattcggct atgactgggc acaacagaca atcggctgct    5700
ctgatgccgc cgtgttccgg ctgtcagcgc aggggcgccc ggttcttttt gtcaagaccg    5760
acctgtccgg tgccctgaat gaactgcagg acgaggcagc gcggctatcg tggctggcca    5820
cgacgggcgt tccttgcgca gctgtgctcg acgttgtcac tgaagcggga agggactggc    5880
tgctattggg cgaagtgccg gggcaggatc tcctgtcatc ccaccttgct cctgccgaga    5940
aagtatccat catggctgat gcaatgcggc ggctgcatac gcttgatccg gctacctgcc    6000
cattcgacca ccaagcgaaa catcgcatcg agcgagcacg tactcggatg gaagccggtc    6060
ttgtcgatca ggatgatctg gacgaagagc atcaggggct cgcgccagcc gaactgttcg    6120
ccaggctcaa ggcgcgcatg cccgacggcg aggatctcgt cgtgacccat ggcgatgcct    6180
gcttgccgaa tatcatggtg aaaatggcc gcttttctgg attcatcgac tgtggccggc    6240
tgggtgtggc ggaccgctat caggacatag cgttggctac ccgtgatatt gctgaagagc    6300
ttggcggcga atgggctgac cgcttcctcg tgctttacgg tatcgccgct cccgattcgc    6360
agcgcatcgc cttctatcgc cttcttgacg agttcttctg aattgaaaaa ggaagagtat    6420
gagtattcaa catttccgtg tcgcccttat ccctttttttt gcggcatttt gccttcctgt    6480
ttttgctcac ccagaaacgc tggtgaaagt aaaagatgct gaagatcagt tgggtgcacg    6540
agtgggttac atcgaactgg atctcaacag cggtaagatc cttgagagtt ttcgccccga    6600
agaacgtttt ccaatgatga gcacttttaa agttctgcta tgtggcgcgg tattatcccg    6660
tattgacgcc gggcaagagc aactcggtcg ccgcatacac tattctcaga atgacttggt    6720
tgagtactca ccagtcacag aaaagcatct tacggatggc atgacagtaa gagaattatg    6780
cagtgctgcc ataaccatga gtgataacac tgcggccaac ttacttctga caacgatcgg    6840
aggaccgaag gagctaaccg cttttttgca acatggggg gatcatgtaa ctcgccttga    6900
tcgttgggaa ccggagctga atgaagccat accaaacgac gagcgtgaca ccacgatgcc    6960
tgtagcaatg gcaacaacgt tgcgcaaact attaactggc gaactactta ctctagcttc    7020
ccggcaacaa ttaatagact ggatggaggc ggataaagtt gcaggaccac ttctgcgctc    7080
ggcccttccg gctggctggt ttattgctga taaatctgga gccggtgagc gtgggtctcg    7140
cggtatcatt gcagcactgg ggccagatgg taagccctcc cgtatcgtag ttatctacac    7200 gacgggagt caggcaacta tggatgaacg aaatagacag atcgctgaga taggtgcctc    7260
actgattaag cattggtaac tgtcagacca agtttactca tatatacttt agattgattt    7320
aaaacttcat ttttaattta aaaggatcta ggtgaagatc ctttttgata atctcatgac    7380
caaaatccct taacgtgagt tttcgttcca ctgagcgtca ccccgtag aaaagatcaa     7440 aggatcttct tgagatcctt ttttttctgcg cgtaatctgc tgcttgcaaa caaaaaaacc    7500
accgctacca gcggtggttt gtttgccgga tcaagagcta ccaactcttt ttccgaaggt    7560
aactggcttc agcagagcgc agataccaaa tactgttctt ctagtgtagc cgtagttagg    7620
ccaccacttc aagaactctg tagcaccgcc tacatacctc gctctgctaa tcctgttacc    7680
```

```
agtggctgct gccagtggcg ataagtcgtg tcttaccggg ttggactcaa gacgatagtt   7740
accggataag gcgcagcggt cgggctgaac gggggttcg tgcacacagc ccagcttgga    7800
gcgaacgacc tacaccgaac tgagatacct acagcgtgag ctatgagaaa gcgccacgct   7860
tcccgaaggg agaaaggcgg acaggtatcc ggtaagcggc agggtcggaa caggagagcg   7920
cacgagggag cttccagggg gaaacgcctg gtatctttat agtcctgtcg ggtttcgcca   7980
cctctgactt gagcgtcgat ttttgtgatg ctcgtcaggg gggcggagcc tatgaaaaa    8040 cgccagcaac gcggccttt tacggttcct ggccttttgc tggccttttg ctcacatgtt    8100 cttcctgcg ttatccctg attctgtgga taaccgtatt accgcctttg agtgagctga     8160
taccgctcgc cgcagccgaa cgaccgagcg cagcgagtca gtgagcgagg aagcggaag    8219
```

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
atcgcaagag gaaaggcagt                                               20

<210> SEQ ID NO 3
<211> LENGTH: 22
<212> TYPE: DNA
<213> ORGANISM: Artificial sequence
<220> FEATURE:
<223> OTHER INFORMATION: Synthetic

<400> SEQUENCE: 3
atccttcctt ggtgttctgc at                                            22

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
aggcccacag tcagattgaa                                               20

<210> SEQ ID NO 5
<211> LENGTH: 23
<212> TYPE: DNA
<213> ORGANISM: Artificial sequence
<220> FEATURE:
<223> OTHER INFORMATION: Synthetic

<400> SEQUENCE: 5
tggtaccaaa gaagccaatt cat                                           23

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
ggcgtcggga caaaatgaac                                               20

```
<210> SEQ ID NO 7
<211> LENGTH: 22
<212> TYPE: DNA
<213> ORGANISM: Artificial sequence
<220> FEATURE:
<223> OTHER INFORMATION: Synthetic

<400> SEQUENCE: 7
tctaacttcc tggacattgc at                                              22

<210> SEQ ID NO 8
<211> LENGTH: 22
<212> TYPE: DNA
<213> ORGANISM: Artificial sequence
<220> FEATURE:
<223> OTHER INFORMATION: Synthetic

<400> SEQUENCE: 8
tgcaatgtcc aggaagttag at                                              22

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
tggtggcacc tctcaaagtt                                                 20

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
taggatgtga ccgagggaag                                                 20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
agctctggcc aataaggtca                                                 20

<210> SEQ ID NO 12
<211> LENGTH: 15
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 12
cacgtgnnnc acgtg                                                      15

<210> SEQ ID NO 13
<211> LENGTH: 25
```

```
<212> TYPE: DNA
<213> ORGANISM: Artificial sequence
<220> FEATURE:
<223> OTHER INFORMATION: Synthetic

<400> SEQUENCE: 13
caccgctgga cattgcattg catgt                                          25

<210> SEQ ID NO 14
<211> LENGTH: 25
<212> TYPE: DNA
<213> ORGANISM: Artificial sequence
<220> FEATURE:
<223> OTHER INFORMATION: Synthetic

<400> SEQUENCE: 14
aaacacatgc aatgcaatgt ccagc                                          25

<210> SEQ ID NO 15
<211> LENGTH: 25
<212> TYPE: DNA
<213> ORGANISM: Artificial sequence
<220> FEATURE:
<223> OTHER INFORMATION: Synthetic

<400> SEQUENCE: 15
atcgtgccac tcaaatagat gccac                                          25

<210> SEQ ID NO 16
<211> LENGTH: 25
<212> TYPE: DNA
<213> ORGANISM: Artificial sequence
<220> FEATURE:
<223> OTHER INFORMATION: Synthetic

<400> SEQUENCE: 16
catctatttg agtggcacga tcaaa                                          25

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
tccatctttc tcgcgttacc                                                20

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
tcctggtaac gcgagaaaga                                                20

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
```

```
agatgctagt gagattcgac                                               20
```

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20

```
ccaccacacc tgaaagcaga a                                             21
```

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21

```
aggtgaaagg cagggactca                                               20
```

<210> SEQ ID NO 22
<211> LENGTH: 21
<212> TYPE: DNA
<213> ORGANISM: Artificial sequence
<220> FEATURE:
<223> OTHER INFORMATION: Synthetic

<400> SEQUENCE: 22

```
gctggagtca gttaccgtca a                                             21
```

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23

```
atgtgttgca gaacgcacct                                               20
```

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24

```
cacgcgagtg ttcttttccg                                               20
```

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25

```
aagtccgtgg tgatgctacg                                               20
```

COMPOSITIONS AND METHODS FOR IDENTIFYING METABOLICALLY ACTIVE AGENTS

CROSS-REFERENCE TO RELATED APPLICATION

The present application is a continuation of U.S. patent application Ser. No. 15/652,968, filed Jul. 18, 2017, which claims priority to U.S. Provisional Patent Application Ser. No. 62/363,585 filed Jul. 18, 2016, each of which is hereby incorporated by reference in its entirety.

STATEMENT REGARDING FEDERAL FUNDING

This invention was made with government support under DK090625 awarded by the National Institutes of Health. The government has certain rights in the invention.

FIELD

The present invention relates to cells with altered cell cycle control. In particular, the present invention provides cells with altered cell cycle control and uses of such cells to identify metabolically active agents.

BACKGROUND

Diabetes presently affects over 30 million individuals in the United States and over 400 million individuals worldwide and is caused by an inability of beta cells in the pancreas to produce insulin in sufficient quantities to maintain blood glucose levels within a healthy range. Type 2 diabetes (T2DM) is the most prevalent form of the disease and is caused increased demand for insulin when glucose-disposing organs become insulin resistant. While T2DM frequently occurs as a consequence of obesity, not all obese individuals develop diabetes indicating that the failure of beta cells to functionally compensate for insulin resistance is a key determinant of the disease. Despite the widespread and growing prevalence of diabetes, the only present therapies for diabetes that directly target beta cell funding are limited to: (1) sulfonylureas and glinides drugs that induce insulin secretion independent of nutrient demand, which lead to hypoglycemia and progression of beta cell failure, and (2) glucagon like-peptide 1 (glp-1) agonists which require injection and act downstream of a G-protein coupled receptor to stimulate insulin release, and dipeptidyl peptidase-4 inhibitors (DPP4), agents which stabilize endogenous glp-1 and exert modest anti-hyperglycemic effects. A goal in diabetes drug discovery is to identify genes and proteins regulating the capacity to sustain beta cell function in insulin resistance and to target these therapeutically while also preventing hypoglycemia. Importantly, agents which act synergistically with the glp-1 drug class and DPP4 inhibitors would have the significant benefit of introducing a new class of agents to both augment insulin secretion and protect beta cell survival in diabetes without causing either weight gain or hypoglycemia, two major complications of diabetes treatments with sulfonylureas, glinides and other therapies (e.g. insulin). At the clinical level, dysregulation of circadian rhythms in shift work and sleep disruption are bona-fide risk factors for human T2DM, exacerbating insulin resistance and inhibiting beta cell compensation.

New methods for identifying and screening diabetes drugs are needed.

SUMMARY

The present invention relates to cells with altered cell cycle control. In particular, the present invention provides cells with altered cell cycle control and uses of such cells to identify metabolically active agents.

In some embodiments, the present invention provides a plurality of immortalized or primary beta cells, wherein the beta cells lack a functional Bmal1 gene. In some embodiments, the Bmal1 gene comprises a deletion of at least a portion of the gene. In some embodiments, the cells further comprise a reporter gene that reports the level of insulin secretion. In some embodiments, the reporter gene expresses a fluorescent or bioluminescent marker (e.g., luciferase) in response to cleavage of proinsulin. In some embodiments, the reporter gene is present on a plasmid. In some embodiments, the cells lack glucose-stimulated insulin secretion. In some embodiments, the cells exhibit impaired glucose-stimulated insulin secretion. In some embodiments, the beta cells are in vitro, ex vivo, or in vivo in a non-human mammal.

Additional embodiments provide a composition, kit or system, comprising: a) the beta cells described herein; and b) glucose. In some embodiments, compositions, kits, and systems further comprise one or more of controls (e.g., insulin secretion control), buffers, analysis components (e.g., computer software, computer processor, or display screen), test compounds, and the like.

Yet other embodiments provide a method of screening for compounds that alter insulin secretion, comprising: a) contacting the beta cells described herein with a test compound and glucose; and b) measuring the level of insulin secretion in the beta cells in the presence and absence of the test compound. In some embodiments, test compounds that restore insulin secretion are identified. In some embodiments, the screening is high-throughput screening. Still other embodiments provide a compound identified by the methods described herein.

Further embodiments provide a plurality of immortalized or primary myoblasts, wherein the myoblasts lack a functional Bmal1 gene. In some embodiments, the myoblasts exhibit impaired oxygen consumption and/or extracellular lactate production. In some embodiments, the myoblasts exhibit reduced hypoxia induced HIF1α accumulation.

Still further embodiments provide a composition, kit or system, comprising: the myoblasts described herein.

Some embodiments provide a method of screening for compounds that alter oxygen consumption, comprising: a) contacting the myoblasts described herein with a test compound; and b) measuring the level of oxygen consumption said myoblasts in the presence and absence of said test compound. In some embodiments, test compounds that restore oxygen consumption are identified. In some embodiments, the method further comprises contacting the myoblasts with glucose. Still other embodiments provide a compound identified by the methods described herein.

Additional embodiments are provided herein.

BRIEF DESCRIPTION OF THE DRAWINGS

(FIG. 1A) Bottom: Glucose- and KCl-stimulated insulin secretion in synchronized wild-type mouse islets across 3 or 2 consecutive days, respectively (n=3 replicate sets of islets pooled from 6 to 9 mice each). Top: Bioluminescence monitoring (counts/s) in islets from Per2Luc reporter mice was performed in parallel. (FIG. 1B) Glucose-stimulated insulin secretion in ethanol- or tamoxifen-treated islets from PdxCreER;Bmal1flx/flx mice at the nadir (36 hours after forskolin shock) and zenith (48 hours after forskolin shock) of cyclic insulin secretion in wild-type islets from FIG. 1A (n=4 islet pools per time point, three replicates per islet pool). (FIG. 1C) Top: Bmal1 and Rev-erbα RNA expression. Middle: Heat map of all cycling genes identified by eJTK_CYCLE analysis. Bottom: Significantly enriched KEGG ontology pathways shown within the cycling gene set. (FIG. 1D) Left: Peak phase expression (hours after forskolin shock) of cycling genes in synchronized wild-type islets that were also altered in PdxCre; Bmal1flx/flx islets at ZT2. Right: Log 2 change in expression in PdxCre;Bmal1flx/flx (KO) islets relative to Bmal1flx/flx (control) at ZT2 for subset of genes relevant to insulin secretion. (FIG. 1E) Heat map showing expression patterns of cycling trafficking and exocytosis genes in synchronized human islets. (FIG. 1F) Mapping of cycling RNAs in both human and mouse islets onto the "Insulin Secretion" KEGG pathway. All values in (A) and (B) represent mean±SEM; *P<0.05, ***P<0.001.

(FIG. 2A) Top: Model of transcriptional targets and chromatin modifications for ChIP-seq experiments. Bottom: UCSC Genome Browser tracks at Nr1d1 (Rev-erbα) locus in β cells. (FIG. 2B) Distribution of BMAL1 and CLOCK peaks at cycling and noncycling gene targets expressed in islets. (FIG. 2C) KEGG ontology terms enriched in cycling and noncycling BMAL1 and CLOCK target genes.

(FIG. 3A) Top: Overlap of genes identified at BMAL1 binding sites in β cells and liver. Middle: Scatterplots show BMAL1 binding in liver (y axis) versus β cells (x axis) within 500-bp windows surrounding peaks identified in each tissue. Bottom: Browser track view of BMAL1 binding in β cells and liver at the Gpr137 locus. (FIG. 3B) Top: Overlap of cycling and direct BMAL1 target genes in β cells that have been reported to cycle in liver. Bottom: Cycling BMAL1 direct target genes containing shared or unique binding sites in β cells and liver. (FIG. 3C) Top: Heat maps comparing binding of indicated factors within 1-kb windows surrounding promoter (3492) and enhancer (5771) localized H3K4Me2 peaks annotating to genes containing cycling RNAs in wild-type islets. Bottom: Histograms summarizing normalized tag counts for H3K27Ac (in β cells and liver) and PDX1 (in β cells) across 6-kb span centered at all β cell H3K4Me2 peaks. (FIG. 3D) Box-and-whisker plots (whiskers represent interquartile range 1.5) comparing BMAL1 binding in β cells and liver at loci corresponding to H3K4Me2 peaks defined in heat maps.

(FIG. 4A) Blood glucose levels in ad libitum-fed PdxCreER; Bmal1flx/flx mice and littermate controls before and after tamoxifen administration (n=6 to 12 mice per genotype). (FIG. 4B) Glucose tolerance and insulin secretion at ZT2 after intraperitoneal glucose administration in PdxCreER; Bmal1flx/flx mice and littermate controls before and after tamoxifen treatment (n=4 to 11 mice per genotype). Inset represents area under the curve for glucose (104 mg/dl per 120 min). (FIG. 4C) Model of intersecting pathways driving insulin exocytosis. Nutrient, Gs, and Gq receptor signaling that are used to stimulate insulin secretion in (FIG. 4D) to (FIG. 4F) are highlighted. (FIG. 4D to FIG. 4F) Glucose- and nutrient-stimulated (D), cyclase pathway-stimulated (FIG. 4E), and catecholamine-stimulated (FIG. 4F) insulin secretion in islets isolated from tamoxifen-treated Pdx-CreER;Bmal1flx/flx and control mice (n=3 to 8 mice per genotype, three repeats per mouse). Inset of (FIG. 4F) shows ratiometric determination of intracellular Ca2+ using Fura2-AM dye in Beta-TC6 cells in response to insulin secretagogs (n=3 replicates per condition).

(FIG. 7A) Schematic showing timing of PdxCre;Bmal1flx/flx islet isolation (ZT2) for RNA-seq in relation to endogenous diurnal patterns of in vivo insulin secretion. (FIG. 7B) Scatterplot showing RNA expression levels in PdxCre; Bmal1flx/flx and control Bmal1flx/flx islets and volcano plot comparing FDR-adjusted p-values and fold-change among significantly differentially expressed genes (FDR-adjusted p<0.05). (FIG. 7C) Breakdown of up- and down-regulated genes in PdxCre;Bmal1flx/flx islets and overlap with cycling genes identified in synchronized WT islets. (FIG. 7D) Peak phase distribution of all cycling genes with reference to timing of maximal glucose-stimulated insulin secretion and Bmal1 and Rev-erbα expression. (FIG. 7E) Enrichment of KEGG terms among all RNA and cycling genes differentially expressed in PdxCre;Bmal1flx/flx islets. (FIG. 7F) Model of basic vesicular transport pathway depicting proteins involved in i) vesicle budding from the donor membrane, ii) trafficking along cytoskeletal filaments, iii) tethering to the target membrane, and iv) fusion with the target membrane.

(FIG. 8A) Summary of human islet donor information. (FIG. 8B) RNA expression of BMAL1 and REV-ERBα (top) and heatmap showing expression patterns of all cycling RNAs in human islets identified by eJTK_CYCLE analysis (bottom) (Bonferroni corrected p<0.05). (FIG. 8C) Overlap between cycling RNAs identified in mouse and human islets, highlighting the significant enrichment in shared genes involved in synaptic and vesicle signaling. (FIG. 8D) Expression profiles for cycling genes mapping to the "Insulin Secretion" KEGG pathway in FIG. 1F.

(FIG. 9A) Top known HOMER motifs enriched at BMAL1 and CLOCK binding sites from Chip-seq analysis in β-cells (top panel). (FIG. 9B) Scatter plot showing BMAL1 (x-axis) and CLOCK (y-axis) binding as log 2 normalized tag count within 500 bp windows surrounding BMAL1 peaks (blue) and CLOCK peaks (yellow) normalized per 10 million tags. (FIG. 9C) Venn diagram showing overlap of CLOCK/BMAL1 targets in BetaTC6 cells, cycling RNAs in wild type islets, and genes that are differentially expressed genes in PdxCre;Bmal1flx/flx compared to Bmal1flx/flx controls. (FIG. 9D) Distribution of genomic annotations of BMAL1 and CLOCK peaks from Chip-seq in β-cells. (FIG. 9E) Box and whiskers plots (whiskers represent IQR 1.5) comparing BMAL1 ChIPseq tags normalized per 10 million tags in β-cells and liver at loci corresponding to 500 bp windows surrounding BMAL1 peaks identified in either β-cells or in liver. (FIG. 9F) UCSC genome browser tracks at Per2, Cry1, and Dbp loci in β-cells and liver show comparable tag density in both liver and β-cells at core clock loci.

(FIG. 10A) Immunofluorescent staining of BMAL1 (red), insulin (blue), and glucagon (green) in PdxCreER;Bmal1flx/flx and control islets. Scale bars, 25 μm. Immunofluorescent staining of BMAL1 (red) and DAPI (blue) in (FIG. 10B) suprachiasmatic nucleus and (FIG. 10C) feeding centers in the hypothalamus of PdxCreER;Bmal1fix/fix and Bmal1flx/flx mice. SCN, suprachiasmatic nucleus. ARC, arcuate nucleus. DMH, dorsomedial hypothalamic nucleus. VMH, ventromedial hypothalamic nucleus. V3, third ventricle. Scale bars, 50 μm.

(FIG. 11A) Representative actograms showing locomotor activity over a 28 day period in individually-housed PdxCreER and PdxCreER;Bmal1flx/flx mice post-tamoxifen treatment. (FIG. 11B) Period of activity in total darkness (DD), calculated using Chi-square periodogram for days 7-14 in DD (n=4-5 mice per genotype). (FIG. 11C) Food intake (% total) during either the light or dark periods and (FIG. 11D) total food intake (g) in PdxCreER;Bmal1flx/fix and littermate control mice before and after tamoxifen treatment (n=3-5 mice per genotype). (FIG. 11E) Body weight in PdxCreER;Bmal1flx/fix and littermate control mice before and after tamoxifen treatment (n=7-10 mice per genotype).

FIG. 18 shows a sequence of Bmal1-HDR plasmid (SEQ ID NO: 1).

(FIG. 23A) Schematic for CRISPR/Cas9-mediated gene editing of Clock and Bmal1 in β-TC6 cells. (FIG. 23B) mRNA expression of Clock, Bmal1, and Rev-erbα with primers at indicated exon locations. (FIG. 23C) Protein expression of CLOCK and BMAL1 in Clock and Bmal1 (clone 3) KO cell lines. (FIG. 23D) Pert-Luc oscillations detected by bioluminescent imaging from Clock and Bmal1 KO cell lines (clone 3 for both) after temperature synchronization. (FIG. 23E) Glucose- and KCl-stimulated insulin secretion in Clock and Bmal1 KO cell lines (clone 3 for both). *$p<0.05$, **$p<0.01$.

FIGS. 26A-26B show identification of hit compounds from 2,700 compound Spectrum library that enhance insulin secretion in Bmal1 KO β-cells. Table indicates the 23 hit compounds from the Spectrum library that significantly enhanced insulin-Nano-luciferase secretion (z score>3). Many of these are known or predicted to target cell surface and intracellular beta cell proteins that regulate insulin secretion. In the model depicting the KEGG (Kyoto Encyclopedia of Genes and Genomes) pathway for insulin secretion, the targets of the hit compounds, which include major signaling factors downstream of glucose metabolism, GPCR signaling, and ion channel signaling are annotated by the red circled numbers.

DEFINITIONS

Figure 1A:
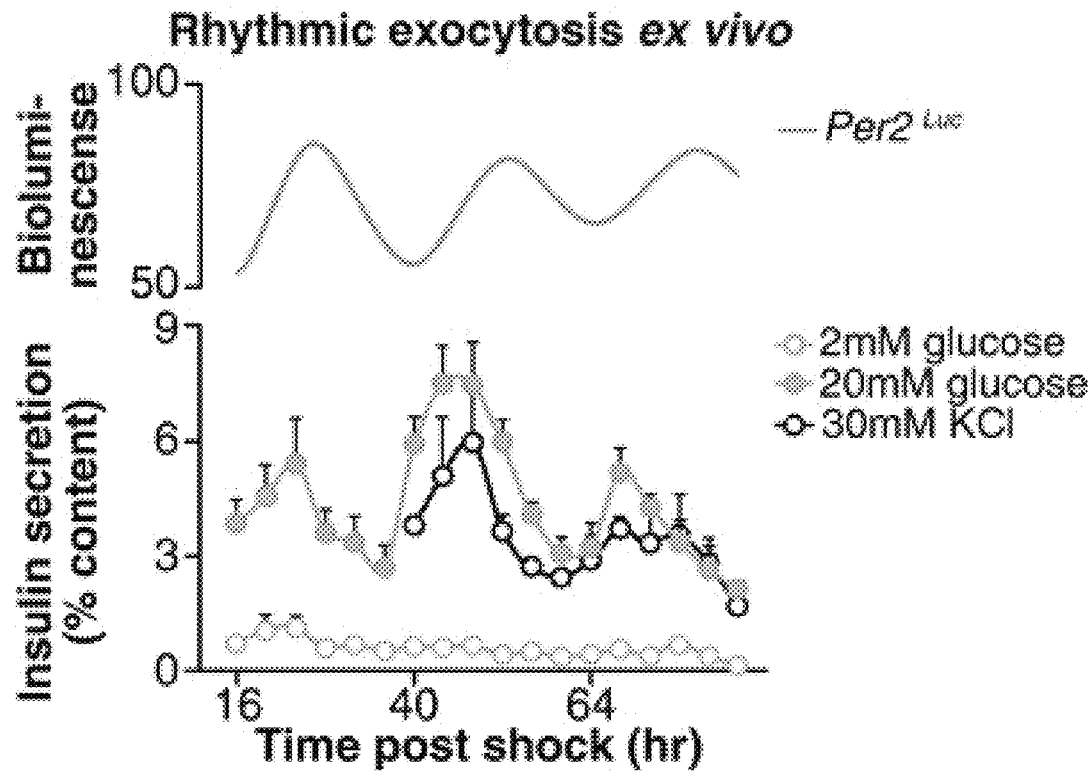
FIGS. 1A-1F show that isolated pancreatic islets display rhythmic insulin secretion and transcription of secretory genes in mice and humans.

As used herein, the terms "pancreatic lineage cells" or "cells of the pancreatic lineage" refer to any endocrine (e.g., alpha cells, beta cells, delta cells, PP cells, epsilon cells, etc.) or exocrine cells that comprise the pancreas, or the precursor cells (e.g., progenitor cells, intermediate development cells, etc.) that are committed to a pancreatic cell lineage.

As used herein, the terms "pancreatic beta cells," "islet beta cells," or "beta cells" refer to monohormonal, pancreatic lineage, endocrine cells located in the islets of Langerhans of the pancreas. Beta cells are capable of secreting insulin in response to elevated glucose concentrations (e.g., glucose-responsive) and express markers, including, but not limited to, insulin and pdx1.

DETAILED DESCRIPTION

The present invention relates to cells with altered cell cycle control. In particular, the present invention provides cells with altered cell cycle control and uses of such cells to identify metabolically active agents.

Intrinsic molecular circadian clock genes in the beta cell are new targets for diabetes therapeutics since they act as regulators of insulin secretion (*Nature* 2010; Science 2015), representing a novel pathway to intervene in conditions of diabetes caused by altered sleep-wake cycles, shiftwork, and jetlag, in addition to other common forms of the disease. A central theme in the approach to developing diabetes drugs stems from the discovery described herein that the molecular clock plays an essential role in beta cell function and insulin secretion. Using conditional gene targeting in mice and genomic profiling in mouse and human beta cells, a genetic map through which the molecular clock controls insulin secretion and survival in the beta cell was developed. Further experiments demonstrated that acutely disrupting circadian genes causes impaired insulin secretion and triggers the rapid onset of diabetes. Moreover, genetic mapping shows that heritable variants in the molecular clock are associated with human glucose metabolism, further indicating that manipulation of the clock pathway may have general implications for diabetes therapeutics in man (Dupuis et al, *Nature Genetics*). Further provided herein are immortalized beta cell lines that enable the discovery of new small molecule drugs to restore insulin secretion in the context of circadian clock gene disruption (e.g., using CRISPR-CAS9 gene editing) and a bioluminescent insulin Nanoluc reporter of endogenous insulin secretion. The Insulin Nanoluc reporter enables high throughput screening using insulin as an endpoint at significant time and cost savings compared with traditional immunoassay approaches. Given the strong association between circadian rhythm dysregulation and human diabetes, it is contemplated that this chemical genetics approach reveals new bioactive molecules that promote functional beta cell compensation in obesity-associated nutrient stress and insulin resistance. While the primary screening endpoint is insulin secretion, it was also found that the clock gene network promotes beta cell growth and survival in mice and as such it is contemplated that molecules enhancing insulin secretion also protect from injury and enhance regeneration. Experiments described herein identified small molecules that enhance insulin secretion in the setting of impaired molecular clock function.

Accordingly, provided herein are a plurality of immortalized or primary beta cells or myoblasts, wherein the beta cells or myoblasts lack a functional Bmal1 gene. In some embodiments, the beta cells are in vitro (e.g., immortalized cell lines), ex vivo, or in vivo in a non-human mammal. In some embodiments, the cells lack glucose-stimulated insulin secretion. In some embodiments, the cells exhibit impaired glucose-stimulated insulin secretion.

The Bmal1 deficient cells described herein find use in research, screening, and therapeutic applications. Exemplary applications are described herein.

In some embodiments, the cells further comprise a reporter gene that reports the level of insulin secretion. In some embodiments, the reporter gene expresses a fluorescent or bioluminescent marker (e.g., luciferase) in response to cleavage of proinsulin. In some embodiments, the reporter gene is present on a plasmid. In some embodiments, the plasmids described herein (e.g., Proinsulin-NanoLuc constructs) are utilized.

In some embodiments, cells are provided in the form of a composition, kit or system, comprising the cells described herein. In some embodiments, compositions, kits, and systems further comprise one or more of controls (e.g., insulin secretion control), glucose, buffers, analysis components (e.g., computer software, computer processor, or display screen), test compounds, and the like.

In some embodiments, the present invention provides methods of screening for compounds (e.g., compounds that find use in the treatment and prevention of diabetes and associated metabolic disorders). In some embodiments, screening methods are comprise contacting the cells described herein (e.g., beta cells or myoblasts that lack functional Bmal1 genes) with a test compound and optionally glucose. Test compounds that alter insulin secretion and/or oxygen consumption are identified (e.g., using insulin report cassettes or the methods described in example 3 below). In some embodiments, the screening is high-throughput screening.

Embodiments of the present invention provide compounds identified by the methods described herein. In some embodiments, such compounds find use in the treatment of diabetes and related disorders.

Embodiments of the present invention further provide pharmaceutical compositions (e.g., comprising one or more of the therapeutic agents described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

In some embodiments, methods of treating and preventing diabetes and/or related disorders are provided (e.g., utilizing compositions identified using the screening methods described herein). Dosing is dependent on severity and responsiveness of the disease state or condition to be treated, with the course of treatment lasting from several days to several months, or until a cure is effected or a diminution of the disease state is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering physician can readily determine optimum dosages, dosing methodologies and repetition rates.

In some embodiments, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues.

EXPERIMENTAL

Example 1

Pancreatic β Cell Enhancers Regulate Rhythmic Transcription of Genes Controlling Insulin Secretion Materials and Methods
Animals Male wild-type C57BL/6J mice were purchased from the Jackson Laboratory. Per2Luc (12) and PdxCre;Bmal1flx/flx (6) mice were produced and maintained on a C57BL/6J background at the Northwestern University Center for Comparative Medicine. Bmal1flx/flx mice (47) were crossed with PdxCreER transgenic mice (kindly provided by D. Melton, Harvard University) (48) to generate PdxCreER; Bmal1flx/flx mice, as well as Bmal1flx/flx and PdxCreER littermate controls. Unless otherwise stated, mice were maintained on a 12:12 light:dark (LD) cycle with free access to regular chow and water. All animal care and use procedures were conducted in accordance with regulations of the Institutional Animal Care and Use Committee at Northwestern University.

Islet Isolation, Insulin Secretion Assays, and In Vitro Islet Synchronization

Figure 5:
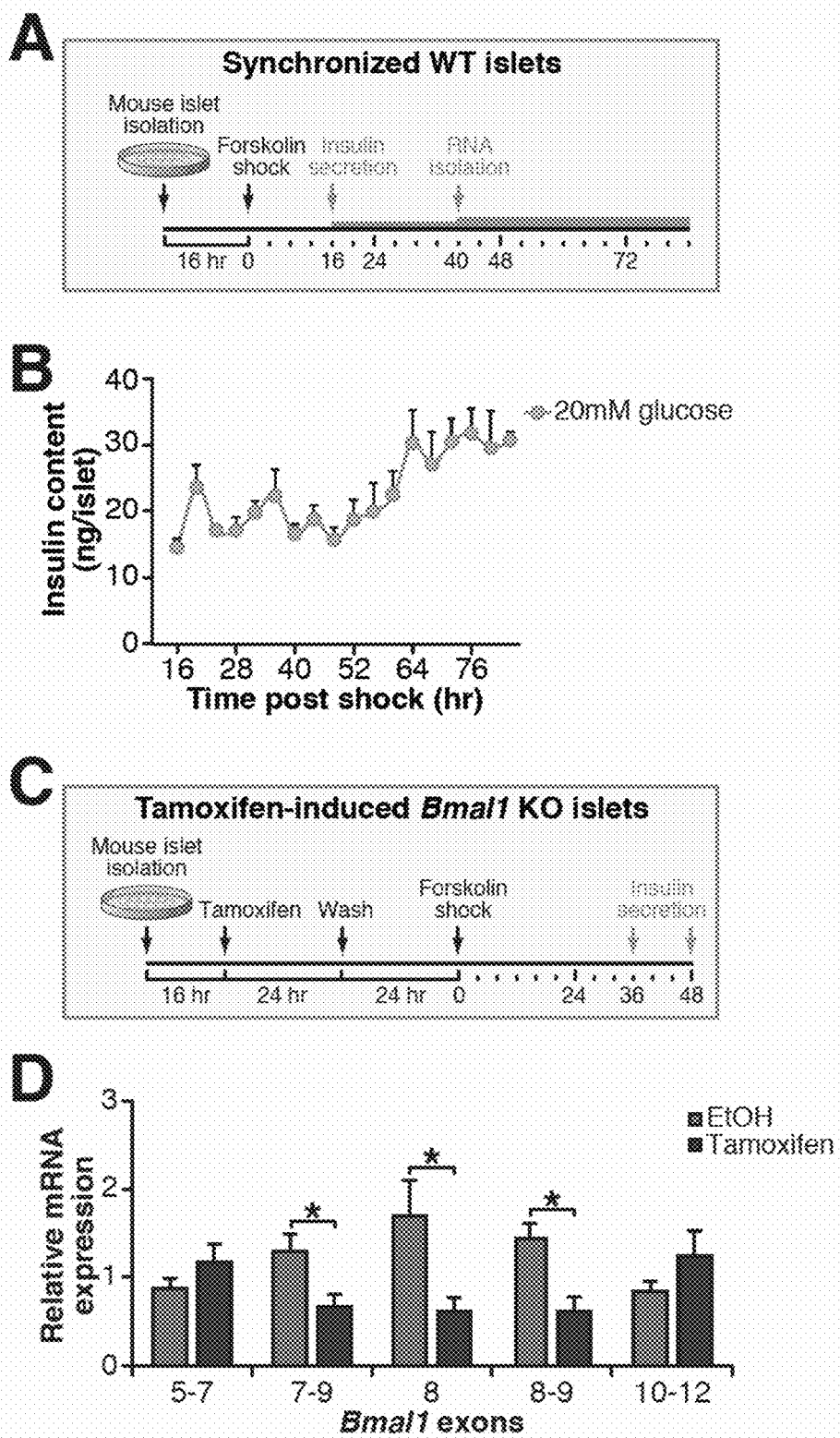
FIG. 5 shows that islet cell autonomous circadian clock controls rhythmic insulin secretion. (Panel A) Schematic of ex vivo experimental design for insulin secretion assays in forskolin-synchronized mouse islets. (Panel B) Average intracellular insulin content in WT islets stimulated with glucose at indicated time points following forskolin treatment (n=4 islet pools per time point, 3 replicates per islet pool). (Panel C) Schematic of ex vivo tamoxifen-induced Bmal1 ablation and insulin secretion in islets isolated from PdxCreER;Bmal1flx/flx mice. (Panel D) Excision of exon 8 of the Bmal1 gene in islets from PdxCreER;Bmal1flx/flx mice after in vitro tamoxifen treatment as assessed by real time PCR using primers specific to indicated exons (n=4 samples per condition).
Figure 6:
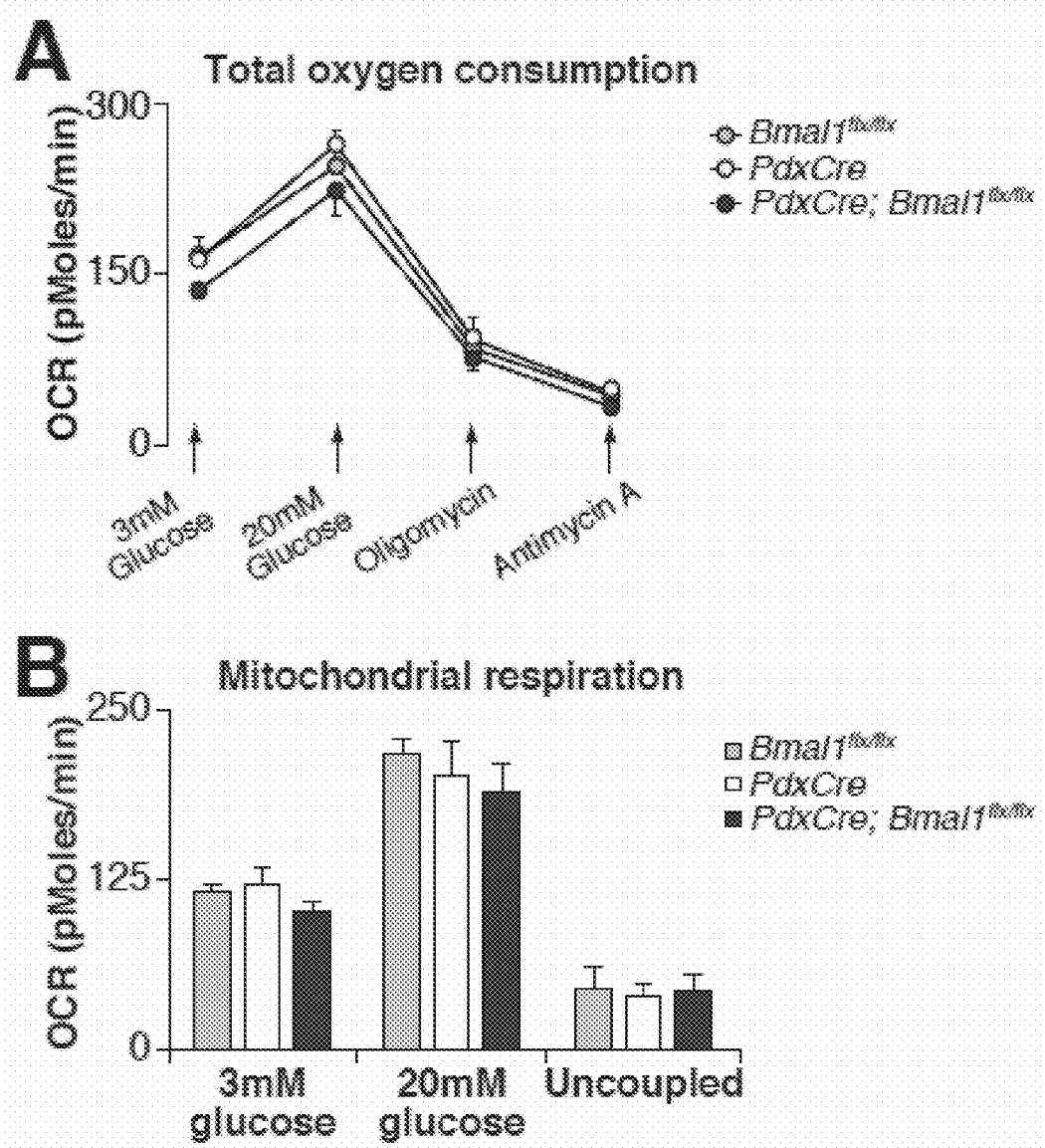
FIG. 6 shows that impaired glucose-stimulated insulin secretion in circadian mutant islets is independent of mitochondrial respiration. (Panel A) Total oxygen consumption rates (OCR) and (Panel B) mitochondrial respiration in islets in the presence of glucose, oligomycin (an ATP synthase inhibitor which inhibits mitochondrial respiration, enabling measurement of uncoupled respiration), and antimycin A (a mitochondrial toxin which enables measurement of nonmitochondrial respiration). Mitochondrial respiration is calculated by subtracting OCR value in the antimycin A condition from basal, glucose- and oligomycin-stimulated islets (n=3-4 mice per genotype, 4 replicates per mouse). All values represent mean±SEM.
Figure 7A:
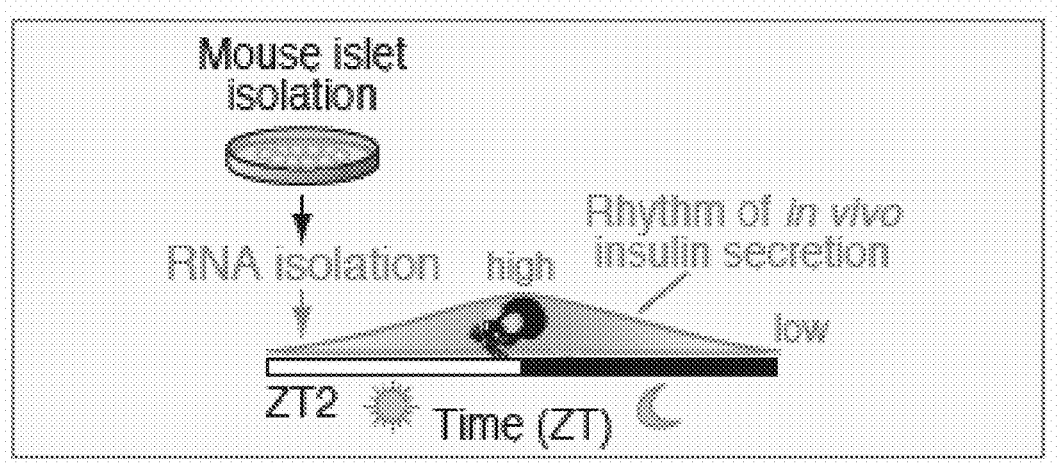
FIGS. 7A-7F show that circadian control of secretory gene expression is dependent on the pancreatic clock.
Figure 7B:
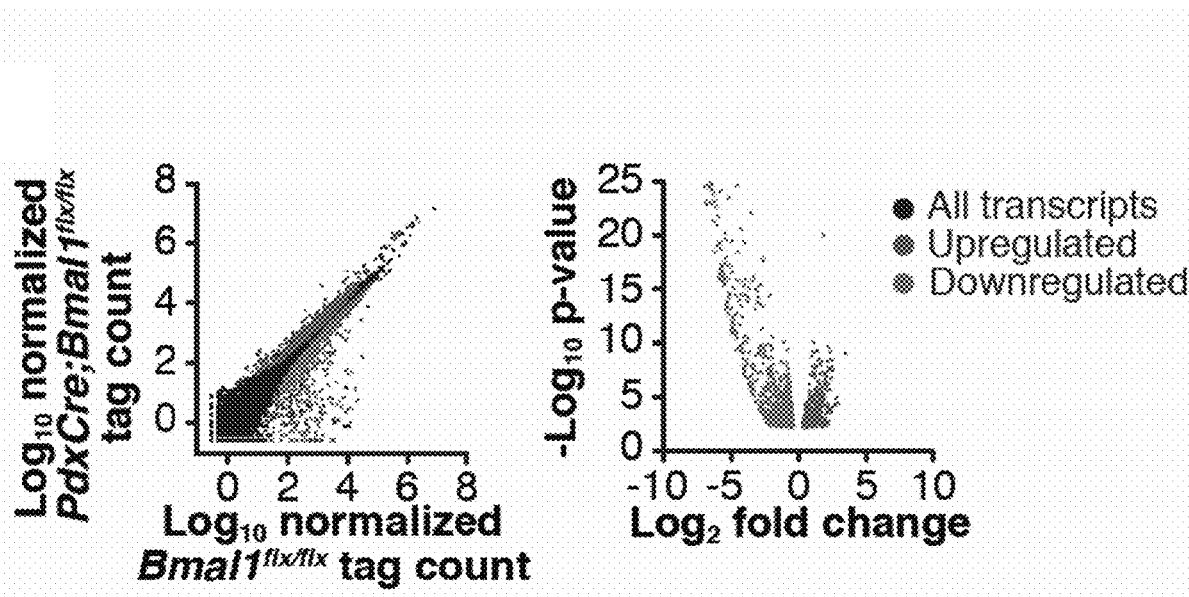
Figure 7C:
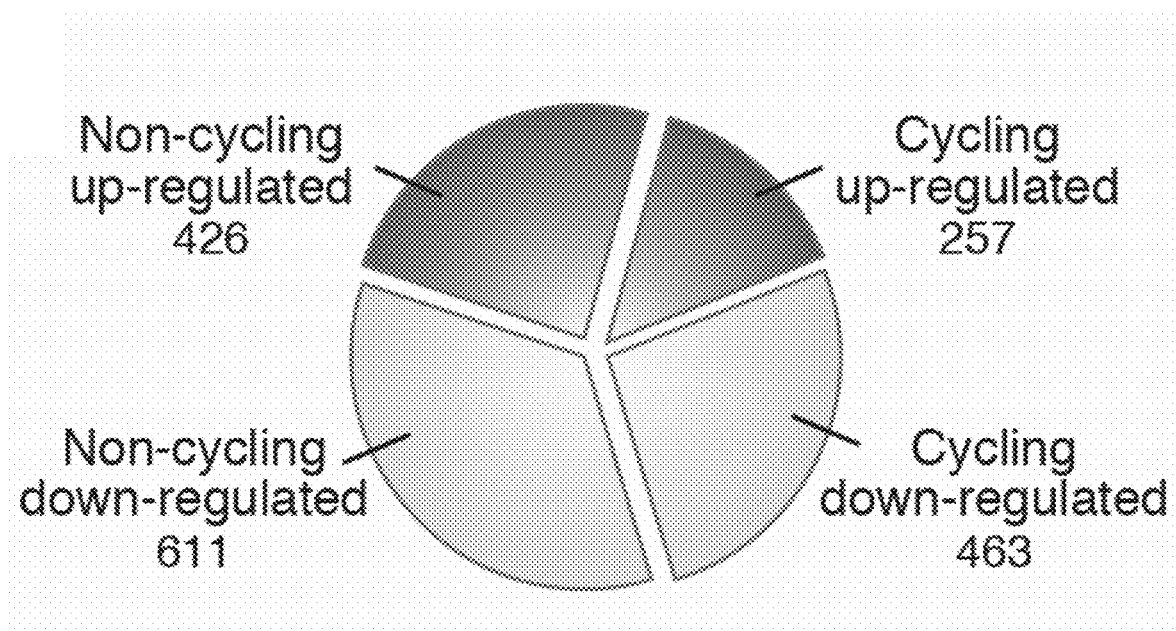
Figure 7D:
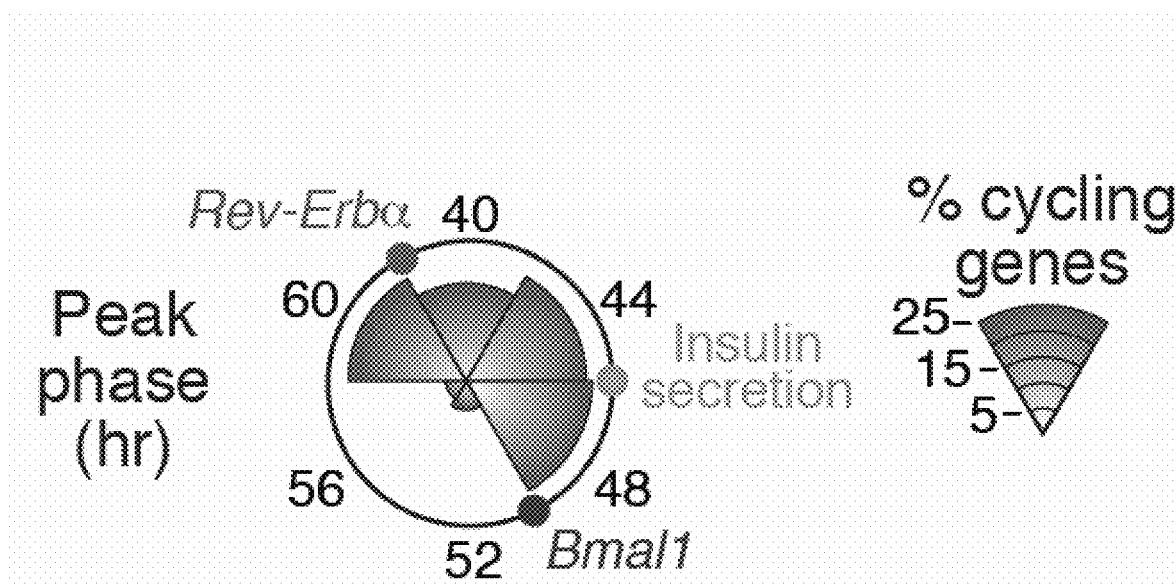
Figure 7E:
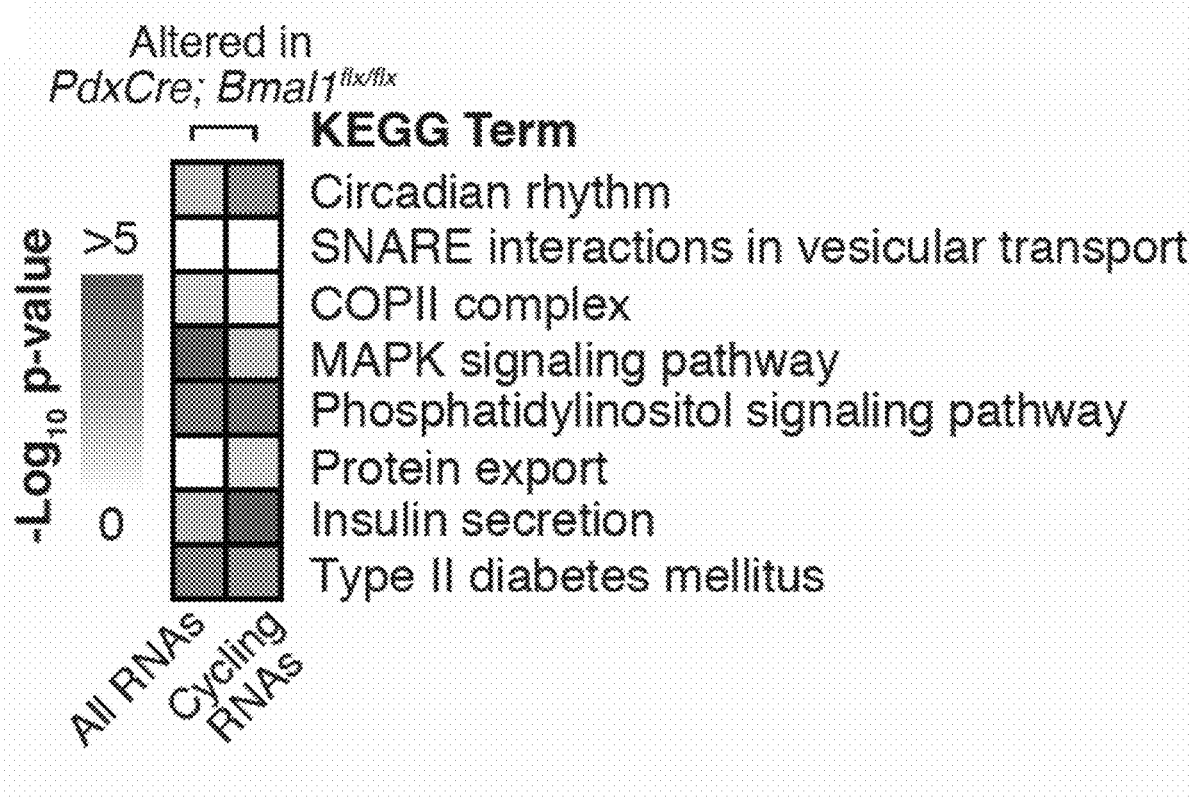
Figure 7F:
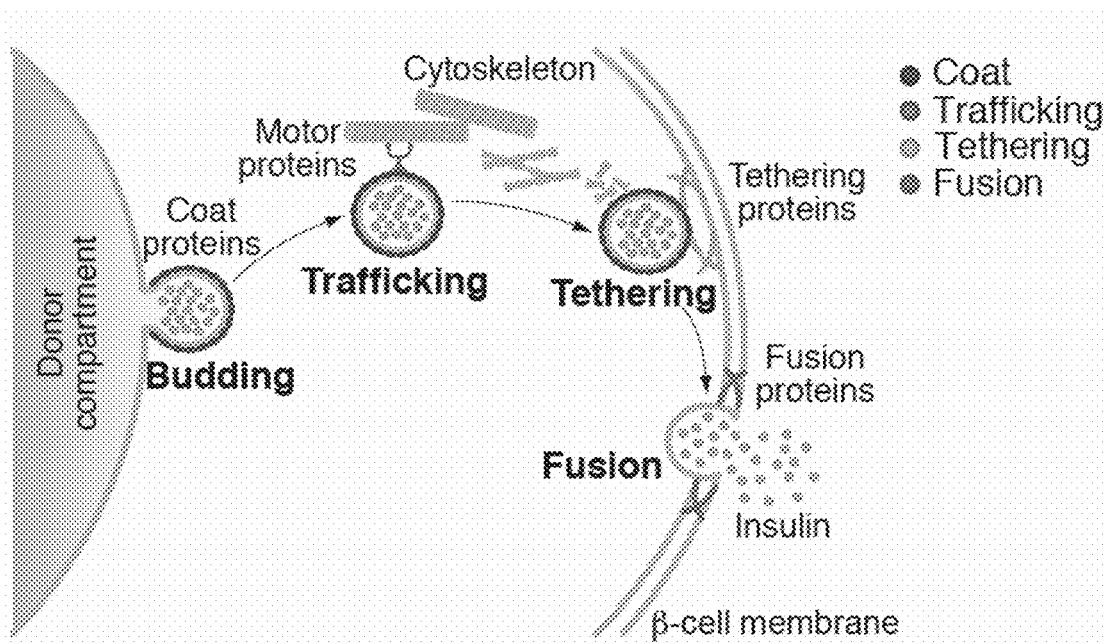

Mouse pancreatic islets were isolated via bile duct collagenase digestion (Collagenase P, Sigma) and Ficoll gradient separation and left to recover overnight (16 hours) at 37° C. in RPMI 1640 with 10% fetal bovine serum (FBS), 1% 1-glutamine, and 1% penicillin/streptomycin. For standard insulin release assays, five islets were statically incubated in Krebs-Ringer buffer (KRB) and stimulated for 1 hour at 37° C. with various glucose concentrations, 30 mM KCl, 2.5 µM forskolin, 1 mM 8-Br-cAMP, 10 mM 1-leucine+2 mM 1-glutamine, 1 mM carbachol, 10 µM PMA, or 10 µM ionomycin. Supernatant was collected and assayed for insulin content by enzyme-linked immunosorbent assay (ELISA; Crystal Chem Inc.). Islets were then sonicated in acid-ethanol solution and solubilized overnight at 4° C. before assaying total insulin content by ELISA. For rhythmic insulin release assays, islets were first synchronized with 10 µM forskolin (Sigma) for 1 hour and allowed to recover for 16 hours. Insulin secretion assays were then performed as above in individual groups of five islets every 4 hours for 72 hours (FIG. 5A). Human islets (obtained from IIDP) were cultured in RPMI 1640 with 10% human AB serum, 1% 1-glutamine, and 1% penicillin/streptomycin (see table in FIG. S4A for details of sex, age, BMI, and IIDP ID numbers of the three donors). For the rhythmic analysis of RNAs in murine and human islets, RNA was isolated (described below) in groups of 200 islets every 4 hours for 48 or 24 hours, respectively, starting 40 hours after forskolin synchronization (FIG. 5A).

LumiCycle Analysis

Approximately 2 hours before the start of the dark period (i.e., lights off), ~100 to 150 pancreatic islets were isolated from Per2Luc mice as described above. Islets were cultured on tissue culture membranes (Millipore) in Dulbecco's modified Eagle's medium (DMEM; Gibco, 1.2 ml) containing sodium bicarbonate (352.5 µg/ml), 10 mM HEPES (Gibco), 2 mM 1-glutamine, 2% B-27 serum-free supplement (Invitrogen), penicillin (25 U/ml), streptomycin (Gibco, 20 µg/ml), and 0.1 mM luciferin sodium salt (Biosynth AG). Sealed cultures were placed at 37° C. in a LumiCycle luminometer (Actimetrics) and bioluminescence from tissues was recorded continuously. After several days in culture, islets were synchronized by 10 µM forskolin (Sigma) treatment for 1 hour followed by incubation in fresh media. Period was calculated via a modified best-fit sine wave analysis using LumiCycle analysis software (Actimetrics).

Measurement of Islet Oxygen Consumption

After bile duct collagenase digestion, 40 purified pancreatic islets were plated in wells of a 96-well respirometry plate (Seahorse Bioscience) and cultured overnight in complete medium. The next day, culture medium was replaced with assay buffer containing 3 mM glucose, 0.8 mM Mg2+, 1.8 mM Ca2+, 143 mM NaCl, 5.4 mM KCl, 0.91 mM NaH2PO4, and phenol red (Seahorse Bioscience; 15 mg/ml) and allowed to equilibrate at 37° C. in a CO2-free incubator for 1 to 2 hours. The plate was then loaded into a Seahorse XF96 instrument, and the oxygen consumption rate (OCR) was measured for four sequential 3-min intervals at basal conditions and after injection of glucose (20 mM final concentration), oligomycin (FIFO ATP synthase inhibitor) (5 µM final concentration), and antimycin A (complex III inhibitor) (5 µM final concentration). OCR values given represent the average of four sequential measurements. Mitochondrial oxygen consumption was calculated by subtracting OCR values after antimycin A treatment (representing nonmitochondrial oxygen consumption).

RNA Isolation and qPCR mRNA Quantification

Islets were added to microfuge tubes containing Tri Reagent (Molecular Research Center Inc.) and frozen at −80° C. RNA was isolated according to the manufacturer's protocol and purified using RNeasy columns (Qiagen). cDNAs were then synthesized using the High Capacity cDNA Reverse Transcription Kit (Applied Biosystems). Real-time quantitative polymerase chain reaction (qPCR) analysis was performed with SYBR Green Master Mix (Applied Biosystems) and analyzed using an Applied Biosystems 7900 Fast Real-Time PCR System. Relative expression levels were determined using the comparative CT method to normalize target gene mRNA to Gapdh. Exon-specific primer sequences for qPCR were as follows: Bmal1 exons 5 to 7, forward, 5'-ATCGCAAGAGGAAAGGCAGT-3' (SEQ ID NO: 2); reverse, 5'-ATCCTTCCTTGGTGTTCTGCAT-3'(SEQ ID NO: 3). Bmal1 exons 7 to 9, forward, 5'-AGGCCCACAGTCAGAT-TGAA-3'(SEQ ID NO: 4); reverse, 5'-TGGTAC-CAAAGAAGCCAATTCAT-3'(SEQ ID NO: 5). Bmal1 exon 8, forward, 5'-GGCGTCGGGACAAAATGAAC-3' (SEQ ID NO: 6); reverse, 5'-TCTAACTTCCTGGACAT-TGCAT-3'(SEQ ID NO: 7). Bmal1 exons 8 and 9, forward, 5'-TGCAATGTCCAGGAAGTTAGAT-3'(SEQ ID NO: 8); reverse, 5'-TGGTGGCACCTCTCAAAGTT-3'(SEQ ID NO: 9). Bmal1 exons 10 to 12, forward, 5'-TAG-GATGTGACCGAGGGAAG-3'(SEQ ID NO: 10); reverse, 5'-AGCTCTGGCCAATAAGGTCA-3'(SEQ ID NO: 11).

RNA Sequencing and Analysis

After RNA isolation (described above), RNA quality was assessed using a Bioanalyzer (Agilent), and sequencing libraries were constructed using an Illumina TruSeq Stranded mRNA sample prep kit LT (Illumina, RS-122-2101) according to the manufacturer's instructions. Libraries were quantified using both a Bioanalyzer (Agilent) and qPCR-based quantification (Kapa Biosystems) and sequenced on either an Illumina HiSEq 2000 or NextSEq 500 instrument to a depth of at least 30 million reads using 100-base pair (bp) or 75-bp paired-end reads, respectively.

For differential expression comparison between PdxCre; Bmal1flx/flx and Bmal1flx/flx islets, RNA raw sequence reads were aligned to the reference genome (mm10) using STAR version 2.3.1s_r366 (49). Differentially expressed RNAs were identified using DESEq 2 version 1.6.3 (50) (FDR-adjusted $P<0.05$).

For cycling RNAs, raw sequence reads were similarly aligned using STAR (mm10 index for mouse and hg19 for human), and uniquely mapped reads (tags) were normalized using the algorithm used in DESEq 2 (50). The geometric mean of the raw read counts was calculated for each gene. A normalization factor was calculated for each sample using the median of the raw read counts of each gene divided by the geometric mean of the gene. The normalized read counts were computed by dividing the raw read counts by the normalization factor. The normalized tags for the mouse and human time series were separately concatenated and z-scored within each gene (14). Rhythm detection of the z-scored and normalized counts was performed with empirical JTK_CYCLE with asymmetry search, which increases sensitivity of detecting cycling transcripts by extending comparisons to reference waveforms beyond cosines, including arbitrary asymmetric waveforms that better represent expression patterns seen in biological data. Rhythmic time series were examined with reference waveforms with a period of 24 hours; a phase of 0, 4, 8, 12, 16, or 20; and an asymmetry of 4, 12, or 20. Because of the small number of waveforms compared, the Bonferroni correction was used instead of the empirical P values. Genes with a Bonferroni-adjusted P value below 0.05 were considered to be rhythmic.

For KEGG ontology term enrichment (51, 52), Ensembl gene IDs were supplied and analyzed using Homer (version 4.7.2) command "findGO" (53). Genes exhibiting rhythmic mRNA accumulation in vivo in liver were derived from reported "exon cycling" transcripts (9).

β Cell Culture

Beta-TC6 cells were purchased from ATCC (CRL-11506) and cultured in DMEM supplemented with 15% FBS, 1% 1-glutamine, and 1% penicillin/streptomycin. All cells used in experiments were at fewer than 15 passages.

Mouse BMAL1 and CLOCK Polyclonal Antibody Generation

Guinea pig anti-mouse BMAL1 and CLOCK polyclonal antibodies were generated using a 37- and 39-amino acid peptide fragment of the mouse BMAL1 and CLOCK proteins, respectively (RS synthesis). Guinea pigs were immunized with KLH-conjugated peptides (Pocono Farms), and BMAL1- and CLOCK-specific antibodies were affinity-purified from whole serum using resin cross-linked with antigen peptides (Pierce).

Chromatin Immunoprecipitation (ChIP)

Beta-TC6 cells (~40 to 160 million) were fixed for 30 min in 2 mM disuccinimidyl glutarate and for 10 min in 1% formaldehyde and then either frozen at −80° C. or processed immediately. Nuclei were isolated in buffer containing 1% SDS, 10 mM EDTA, 50 mM Tris-HCl (pH 8.0), and protease inhibitors and sonicated using a Diagenode Bioruptor to shear chromatin into 200- to 1000-bp fragments. Protein-DNA complexes were incubated with antibodies against BMAL1 and CLOCK (affinity-purified guinea pig IgGs as described above), H3K4Me2 (Abcam), H3K27Ac (Active Motif), H2AZ (Active Motif), or PDX1 (Novus Biologicals) and immunoprecipitated with IgG paramagnetic beads (Invitrogen). Eluted chromatin was isolated using MinElute PCR purification columns (Qiagen).

ChIP Sequencing and Analysis

Sequencing libraries were generated using KAPA DNA Library Preparation kits (Kapa Biosystems, KK8504) according to manufacturer's instructions. Library concentrations were assessed by both a Bioanalyzer (Agilent) and qPCR-based quantification (Kapa Biosystems). Libraries were sequenced using 75-bp single-end reads on an Illumina Next-SEq 500 instrument to a depth of >10 million mapped reads.

Raw sequence reads were aligned to the mm10 reference genome and displayed using UCSC annotated genes using bowtie version 1.1.1 (54) with parameters "-best" and "-m 1" to ensure reporting of uniquely mapped reads (tags). ChIP-seq peaks were designated as regions with a factor of 4 enrichment over both the input sample and the local background and were normalized to 10 million reads using default parameters for the Homer "findPeaks" command (53) and specifying "-style factor" for BMAL1, CLOCK, and PDX1 and "-style histone" for H2A.Z, H3K4Me2, and H3K27Ac. For BMAL1 and CLOCK peaks, promoter binding was defined as peaks occurring within 2 kb of the nearest gene TSS, and distal binding was defined as those occurring greater than 2 kb from a nearest TSS.

To identify consensus motifs for BMAL1 and CLOCK, 50-bp windows surrounding transcription factor peaks we scanned using "findMotifsGenome.pl" with standard background (random genomic sequences sampled according to GC content of peak sequences). The occurrence of tandem E-boxes with variable-length spacing was identified by generating synthetic canonical E-box motifs separated by the indicated number of random spacers (i.e., CACGTGNNNCACGTG=3 spacers (SEQ ID NO: 12)) using "seq2profile.pl" allowing for two mismatches and testing for their occurrence at BMAL1 and CLOCK peaks using "annotatePeaks.pl".

Fastq files for all BMAL1 and H3K27Ac ChIP-seq were downloaded from the ENA server (study accession number SRP014752) and raw sequence reads for 12 sequential time points were concatenated into a single file. Alignments and peak calling were performed using bowtie and Homer as described above. Shared BMAL1 binding sites were identified by comparing binding locations between β cells and liver using the Homer command "mergePeaks" and specifying "-d 200," which identified peaks occurring within 200 bp as shared across tissues.

Tamoxifen Treatment

For in vivo delivery of tamoxifen (Sigma, dissolved in corn oil), mice received three intraperitoneal (i.p.) injections of 200 μg tamoxifen/g body weight, administered every other day. Subsequent experiments were conducted 10 to 14 days after tamoxifen treatment. For in vitro administration of tamoxifen, isolated islets were incubated for 24 hours with 1 mM tamoxifen (dissolved in ethanol) prior to transfer to complete media for 24 hours to recover. Islets were then synchronized with forskolin prior to insulin secretion assays as described above.

Immunohistochemical Analysis

Mice were anesthetized with i.p. injection of phenobarbital (Nembutal, 50 mg/ml) and perfused with heparinized saline, followed by 4% paraformaldehyde (PFA) (Sigma) in PBS. Brain and pancreas were removed and post-fixed with 4% PFA overnight at 4° C. Brain tissues were then cryoprotected in 30% sucrose (Sigma), frozen in O.T.C. (Tissue Tek), and 30-μm brain sections collected for antibody staining. Pancreata were embedded in paraffin, and blocks of 6-μm sections were mounted on slides. The following primary antibodies were used for staining: guinea pig anti-insulin (1:500, DAKO), mouse anti-glucagon (1:500, Sigma), and rabbit anti-BMAL1 (1:500, Novus Biological). Triple staining was visualized with the following secondary antibodies: AMCA goat anti-guinea pig (1:400, Jackson ImmunoResearch), Alexa Fluor 488-conjugated goat anti-mouse (1:400, Invitrogen), and Alexa Fluor 546-conjugated goat anti-rabbit (1:400, Life Technologies). Nuclei were counterstained with 4',6-diamidino-2-phenylindole (DAPI) as indicated. Images were acquired with PictureFrame 1.0 using a Zeiss Axioskop 50. β cell mass was assessed by morphometric analysis of insulin immunostained pancreatic sections (DAKO; Histomouse Plus kit, Life Technologies). Four pancreatic sections, spaced 50 μm apart, were stained for each animal, and endocrine versus total pancreas area was calculated using Image-Pro Premier software (Media Cybernetics) using the smart segmentation feature.

Glucose and Insulin Measurements and Glucose Tolerance Tests

Blood glucose and plasma insulin levels in ad libitum-fed mice were assessed at ZT2 and ZT14 from tail vein bleeds. Glucose tolerance tests were performed in mice after a 14-hour fast, and blood glucose and plasma insulin levels were measured at the indicated times after i.p. glucose injection of either 2 or 3 g/kg body weight, respectively. Plasma insulin levels were measured by ELISA.

Behavioral Analysis

Locomotor activity was analyzed in 2- to 4-month-old pancreas-specific Bmal1 knockout mice and their respective littermate controls after tamoxifen treatment. All animals were individually housed in standard mouse cages equipped with running wheels and allowed free access to food and water. Mice were placed in a 12:12 LD cycle for 14 days, followed by 14 days in constant darkness (DD). Total activity data was recorded and analyzed in 6-min bouts using ClockLab software (Actimetrics). The free-running period was determined as the duration of time between the major activity periods on consecutive days in DD. Period was calculated using a $\chi2$ periodogram for days 7 to 14 in DD. Food consumption was analyzed in pancreas-specific Bmal1 knockout mice and their littermate controls before and after tamoxifen treatment. All animals were individually housed with free access to water and regular chow. Daytime and nighttime food consumption was determined by manual measurement of food at both ZT0 and ZT12 for three consecutive days.

Intracellular Calcium Determination

BetaTC-6 cells were plated at a density of 100,000 cells per well in black 96-well plates with clear bottoms and cultured overnight at 37° C. and 5% CO2. Islets were dispersed to single cells by incubating in 0.05% Trypsin-EDTA at 37° C. for 3 min and plated at a density of 100 islets per well in laminin-treated black 96-well plates with clear bottoms and cultured in complete media for 48 hours at 37° C. and 5% CO2. Cells were then washed with BSA-free KRB buffer with no glucose and loaded with 5 µM Fura-2 (Invitrogen) and 0.04% Pluronic F-127 (Invitrogen) for 30 min at 37° C. Following a wash with BSA-free KRB, Fura-2 intensity was measured after injection of either glucose or ionomycin (Sigma) to final concentrations of 20 mM or 10 µM, respectively. Cells were alternately excited with 340- and 380-nm light, and the emitted light was detected at 510 nm using a Cytation 3 Cell Imaging Multi-Mode Reader (Bio Tek) at sequential 30-s intervals. Raw fluorescence data were exported to Microsoft Excel and expressed as the 340/380 ratio for each well.

Results

Figure 1B:
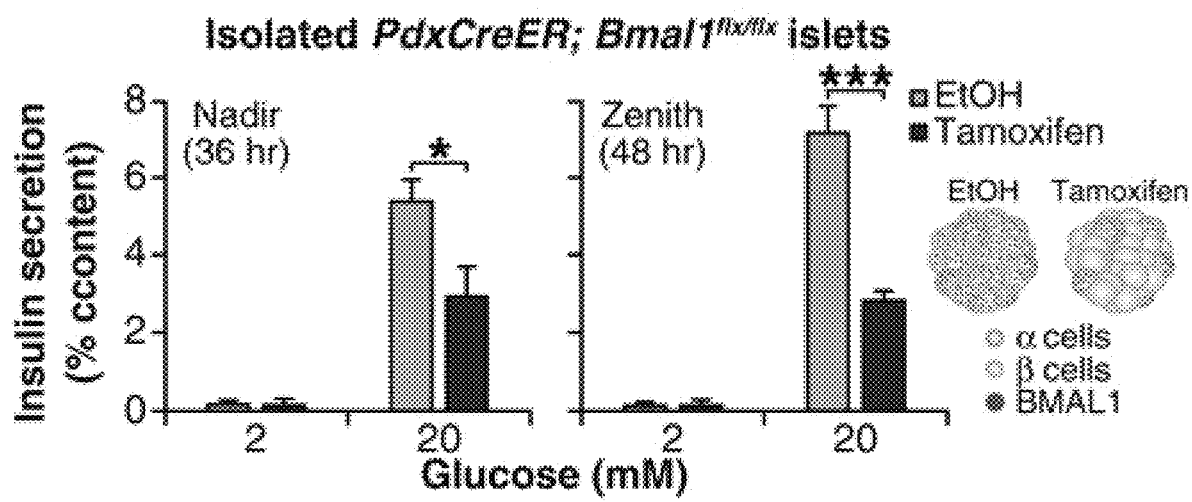

The β Cell Clock Produces Rhythmic Insulin Secretion and Secretory Gene Transcription First, to determine whether transcriptional oscillations in pancreatic islets give rise to rhythmic islet physiology, the phase dependence of pancreatic islet function was determined by analyzing nutrient-induced insulin secretion in parallel with live-cell clock oscillation in islets from Per2Luc reporter mice (12). After synchronization with forskolin (6, 13), insulin secretion was assessed every 4 hours in individual groups of five islets at each time point over the ensuing 72-hour window (FIG. 5A; materials and methods) and observed a striking self-sustained, time of day-dependent variation in the magnitude of response to stimulatory concentrations of both glucose and KCl, which triggers insulin exocytosis through direct depolarization of the β cell (FIG. 1A). Intracellular insulin content did not cycle (FIG. 5B) despite rhythmic glucose-stimulated insulin secretion (GSIS) (FIG. 1A), consistent with circadian regulation at a step after translation of insulin. We further confirmed that GSIS rhythms were autonomous by monitoring insulin secretion after forskolin synchronization at times corresponding to the nadir (36 hours after forskolin shock) and zenith (48 hours after forskolin shock) of the wild-type GSIS rhythm in islets isolated from PdxCreER; Bmal1flx/flx mice (FIG. 1B and FIG. S1C), which when treated with tamoxifen ex vivo displayed >60% reduction in Bmal1 expression (FIG. S1D). Vehicle-treated islets displayed significantly higher GSIS at the zenith than at the nadir, whereas tamoxifen-treated islets exhibited constitutively low levels of insulin secretion (FIG. 1B). Together, these data suggest that the islet molecular clock gates the rhythmic secretory response downstream of membrane depolarization.

Figure 1C:
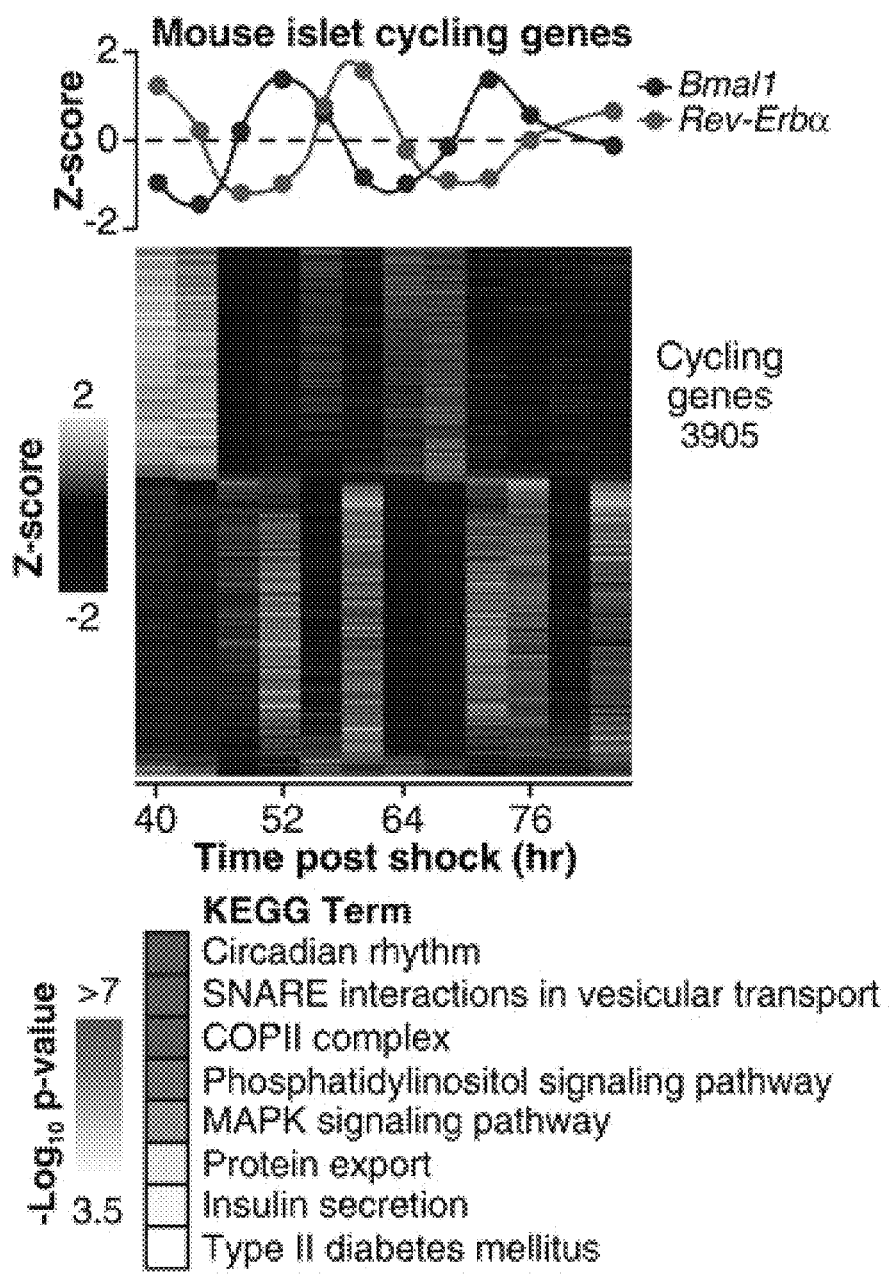

The genome-wide effect of rhythmic transcription on insulin secretory dynamics was examined by performing RNA sequencing (RNA-seq) over two circadian cycles in RNA isolated from wild-type islets synchronized ex vivo (FIG. 5A; materials and methods). Polyadenylated RNAs was analyzed using eJTK_CYCLE (14), a modified non-parametric algorithm with increased sensitivity for detecting cycling transcripts. A total of 3905 cycling transcripts (Bonferroni-corrected P<0.05), which accounted for ~27% of all expressed transcripts within the islet that met a minimum mean expression threshold of 10 normalized counts was identified (FIG. 1C). High-amplitude rhythms for the core clock transcription factors were observed, including Bmal1, Clock, Npas2, Per2, Cry1, Rev-Erbα, and Rorα, with Bmal1 and its repressor Rev-Erbα displaying antiphasic expression (FIG. 1C) (15).

To determine the identity of functional circadian gene networks in the islet, overrepresentation of defined KEGG (Kyoto Encyclopedia of Genes and Genomes) pathways among rhythmic RNAs were identified. Enrichment of factors mediating vesicle exocytosis was observed, which indicates that daily variation in insulin secretory capacity arises from genomic regulation of the transport and release of peptidergic hormone (FIG. 1C and table 1). Overrepresented pathways in the circadian transcriptome included factors involved in (i) vesicle budding, including genes encoding the COPII coat proteins (Sec24a and Sec31a), which mediate vesicle budding from the endoplasmic reticulum (16, 17); (ii) cargo trafficking, specifically the motor proteins (Kif1b, Myo9a, and Dync2h1) that enable vesicle transport along cytoskeletal filaments (18); and (iii) vesicle tethering and fusion to the plasma membrane, including v- and t-SNAREs such as Vamp1, Vamp5, Vamp8, Stx1a, Stx4a, and Stx8 (19, 20). In addition to the cycling of RNAs that encode factors involved in insulin exocytosis, rhythmic RNA expression of insulinotropic signals involved in vesicle movement and membrane fusion, including (i) targets of cAMP/EPAC (cyclic adenosine monophosphate/exchange protein activated by cAMP) signaling (Pclo, Rims2, Rab3b, Rap1a, Rap1b, Rapgef2, Rapgef6) was identified, which mediate vesicle docking and fusion to the plasma membrane (21, 22); (ii) Ca2+-sensing synaptotagmins (Syt11, Syt14, Syt16), which stimulate membrane fusion of synaptic vesicles (23, 24); and (iii) calmodulin-dependent protein kinases (Camk1, Camk4, Camkk2, Camk2g), which regulate vesicle exocytosis and recycling (25). Lastly, we detected significant oscillation in targets of phosphoinositide signaling, including protein kinase C (Prkca, Prkcb) (26), exocyst actin-interacting factors such as Exoc1/Sec3 (27), and the cytoskeletal filament-remodeling Rho guanosine triphosphatases (GTPases) Rho, RhoA, RhoB, and RhoC (18). Collectively, cycling of RNAs that encode factors involved in insulin exocytosis and signaling components reveals a genomic basis for circadian variation in insulin secretion.

To further understand the physiologic function of tissue-specific rhythmic gene transcription, genome-wide rhythms of RNA expression in wild-type islets were compared to those in pancreas-specific clock mutant mice (PdxCre; Bma1flx/flx), which exhibit severe hypoinsulinemic diabetes due to defects downstream of glucose metabolism and mitochondrial respiration (FIG. 7) (6). RNA-seq was performed using RNA isolated from PdxCre;Bmal1flx/flx and control littermate islets at the start of the light phase [zeitgeber time 2 (ZT2), the time of maximal GSIS impairment] (FIG. 8A) (6). Changes in the expression of 1757 genes in islets isolated from clock mutant animals relative to littermate controls (Bmal1flx/flx) were identified, including transcripts that were both decreased (1074) and increased (683) in expression, consistent with actions of the clock as both an activator and repressor of gene expression [false discovery rate (FDR)-adjusted P<0.05] (FIGS. 8, B and C).

Figure 1D:
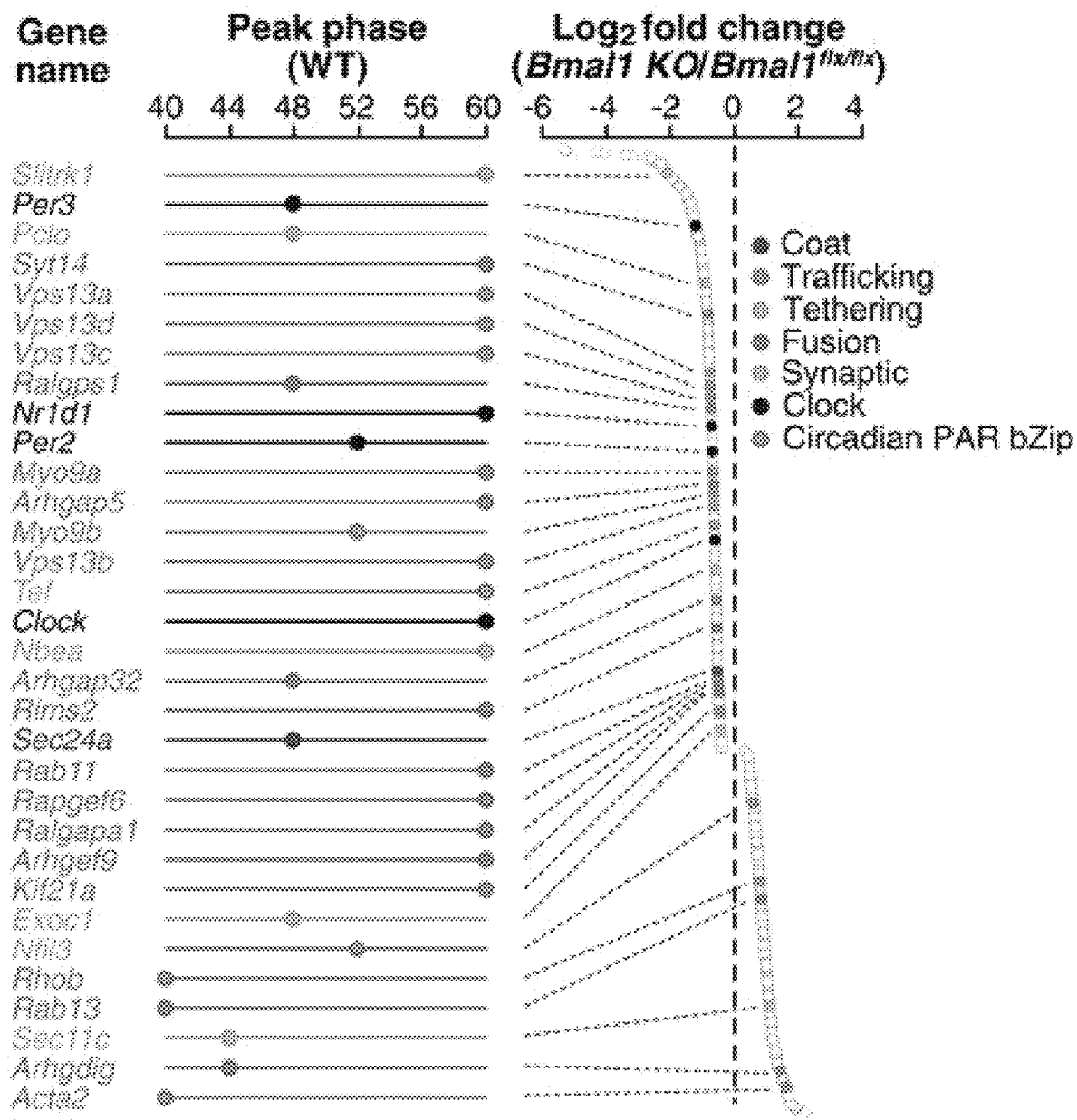
Figure 1E:
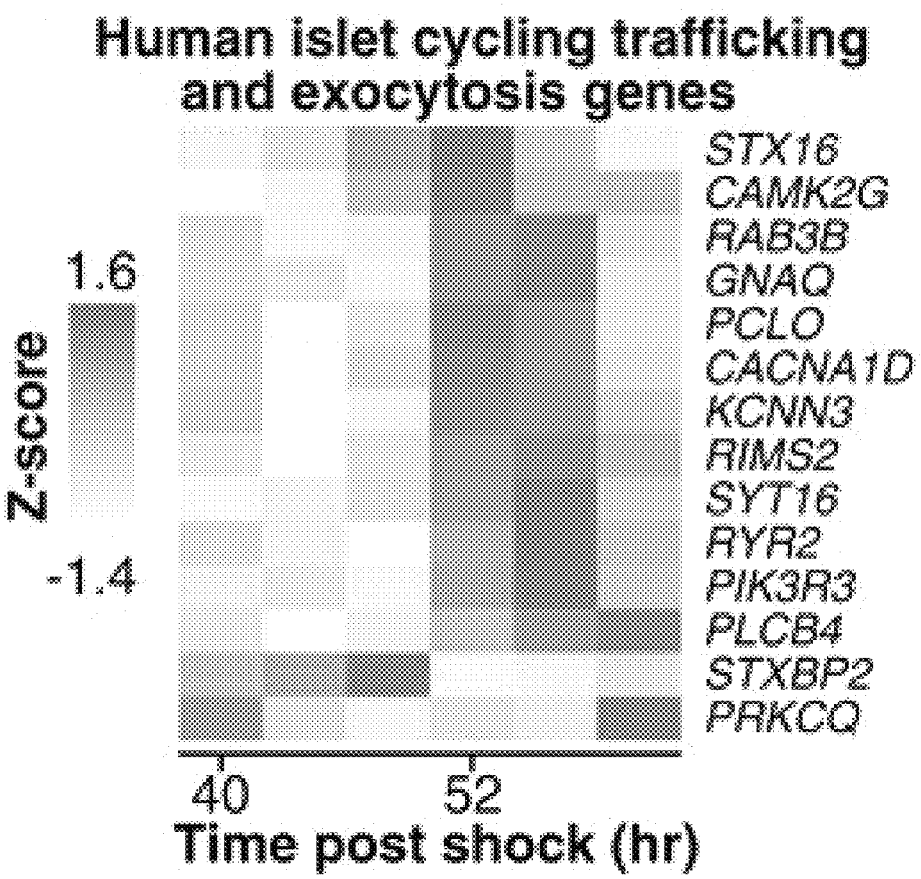
Figure 1F:
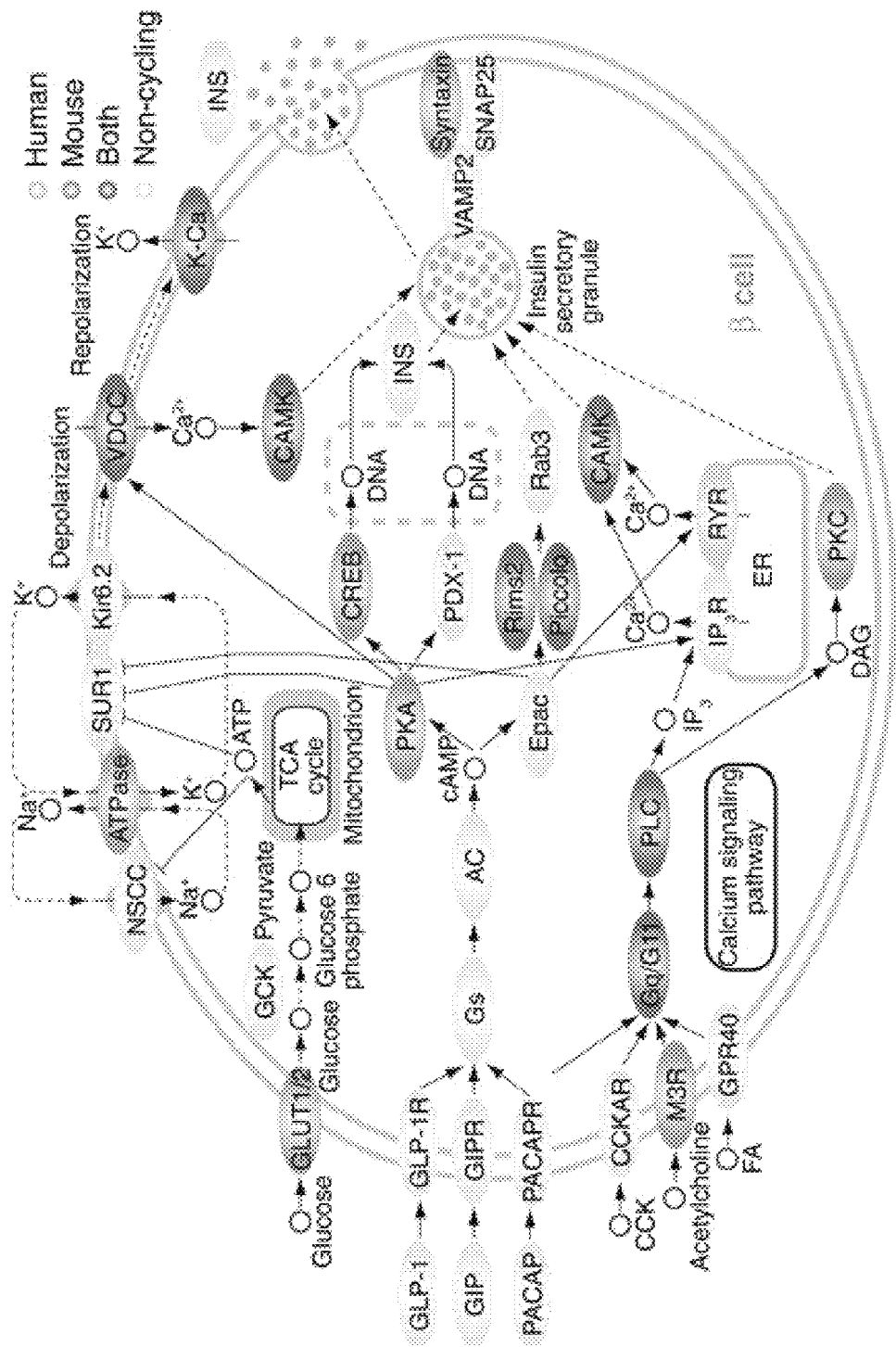

Many of the RNAs that were altered in islet clock knockout mice were identified as cycling RNAs in wild-type islets; overall, a total of 720 oscillating genes exhibited altered expression in animals with disrupted pancreatic clock function (FIG. 8C), indicating an autonomous role of the islet clock in the rhythmic transcriptional regulation of insulin secretion. Among the most significantly changed RNAs were factors in the negative limb of the core clock containing the canonical E-box transcription motif, in addition to circadian PAR bZip transcription factors including Per2, Rev-Erbα (Nr1d1), Tef, and E4bp4 (Nfil3) (FIG. 1D). A broad range of alterations in cycling genes that are circadian outputs and grouped by KEGG annotation into exocytosis networks similar to those described for the wild-type islets were also found, including genes encoding factors involved in trafficking, such as the vacuolar protein sorting factors Vps13b and Vps13c; Myo9, the motor protein involved in vesicular transport; the kinesin transport factor Kif21; and the small GTPase Rab11, a factor in trans-Golgi vesicular biogenesis (28) (FIG. 1D, FIGS. 8, E and F, and table 1). Ontology analysis also identified genes related to vesicle tethering and fusion as altered in clock-deficient islets, including the conserved exocyst component Exoc1/Sec3, cAMP/EPAC-controlled Rims2 and Pclo, and the synaptotagmin Syt14 (FIG. 1D); islet genes involved in glucose sensing were unchanged (table 2). Whereas the complete set of cycling RNAs displayed broadly distributed peak phases (FIG. 8D), the majority of exocytosis-related RNAs that were differentially expressed in clock mutants exhibited peak expression at two distinct phases (48 and 60 hours after forskolin shock) (FIG. 1D). Although this shows that these genes may represent direct targets of CLOCK/BMAL1 and/or a clock repressor (REVERBα/β or E4BP4), nascent RNA-seq studies indicate that peak circadian mRNA phases are not directly correlated with nascent transcription (11). Collectively, sequencing results indicate that secretory pathway genes represent a major output of the islet clock.

Figure 8A:
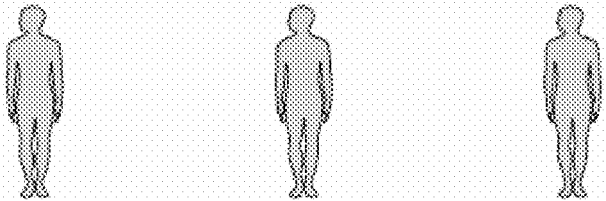
FIGS. 8A-8D show that the circadian transcriptome is conserved in human islets.
Figure 8B:
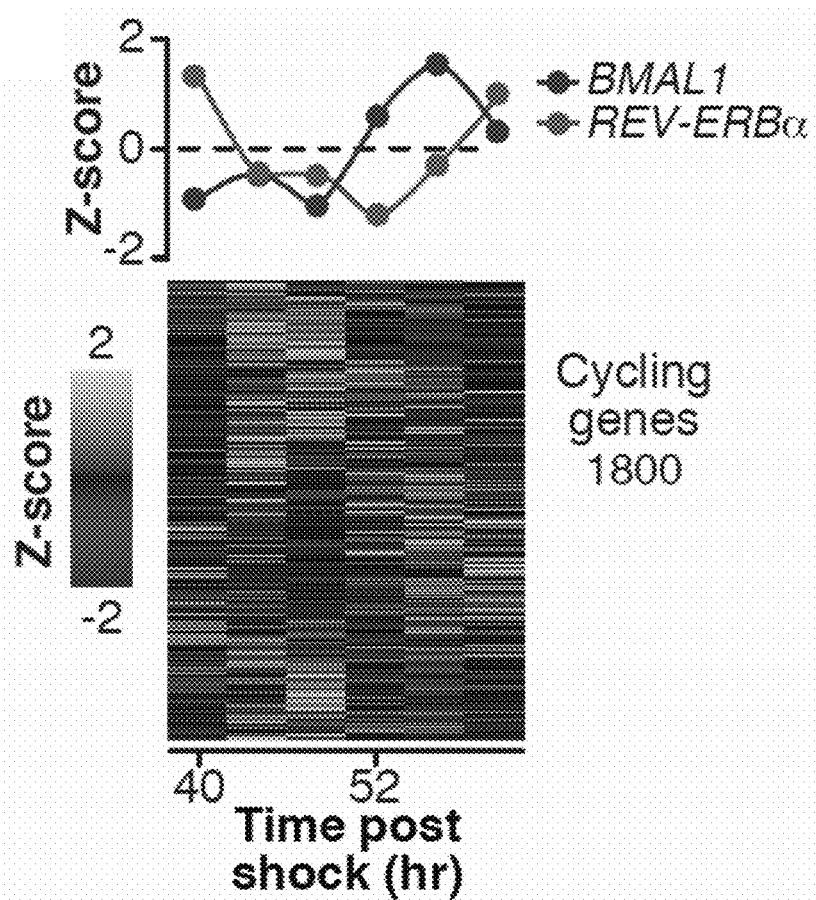
Figure 8C:
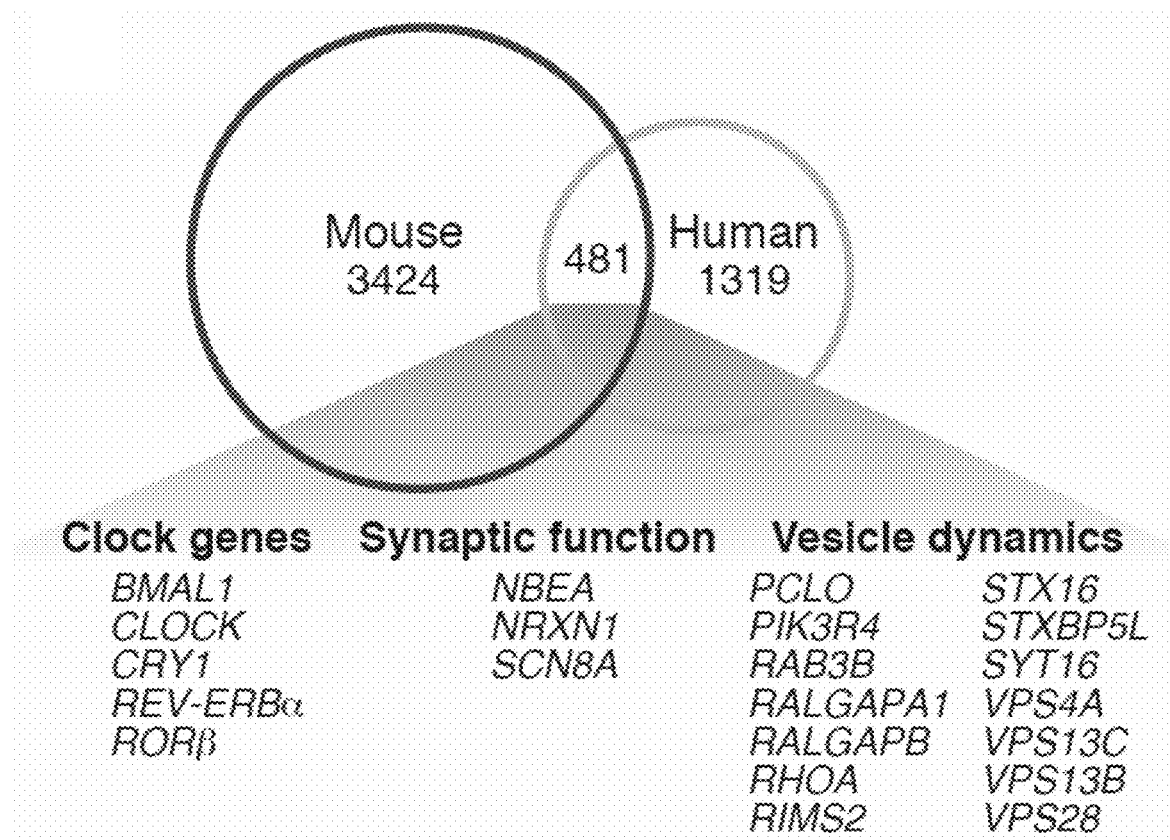
Figure 8D:
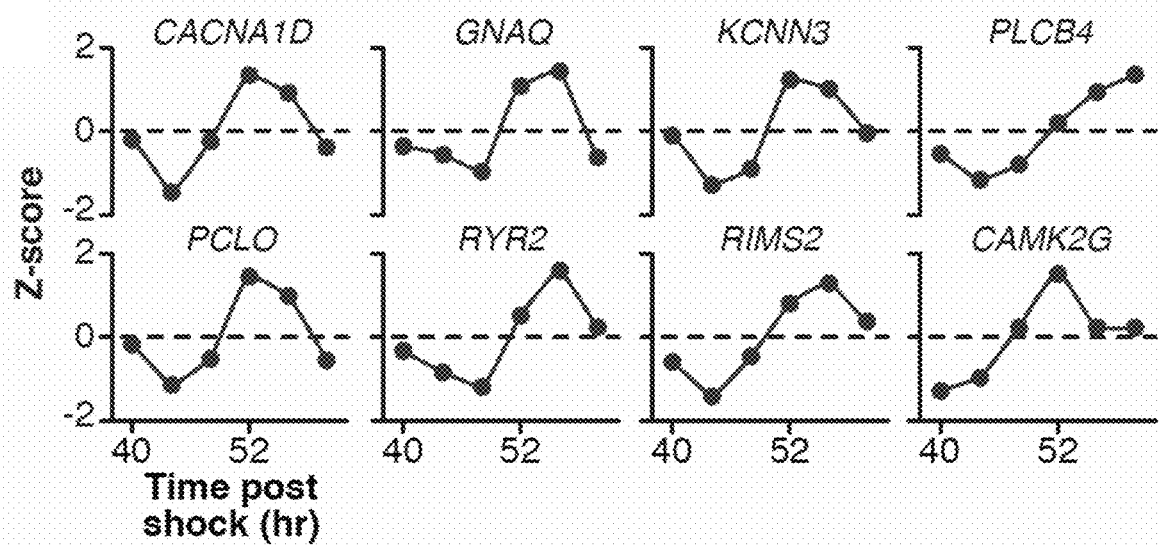
Figure 9A:
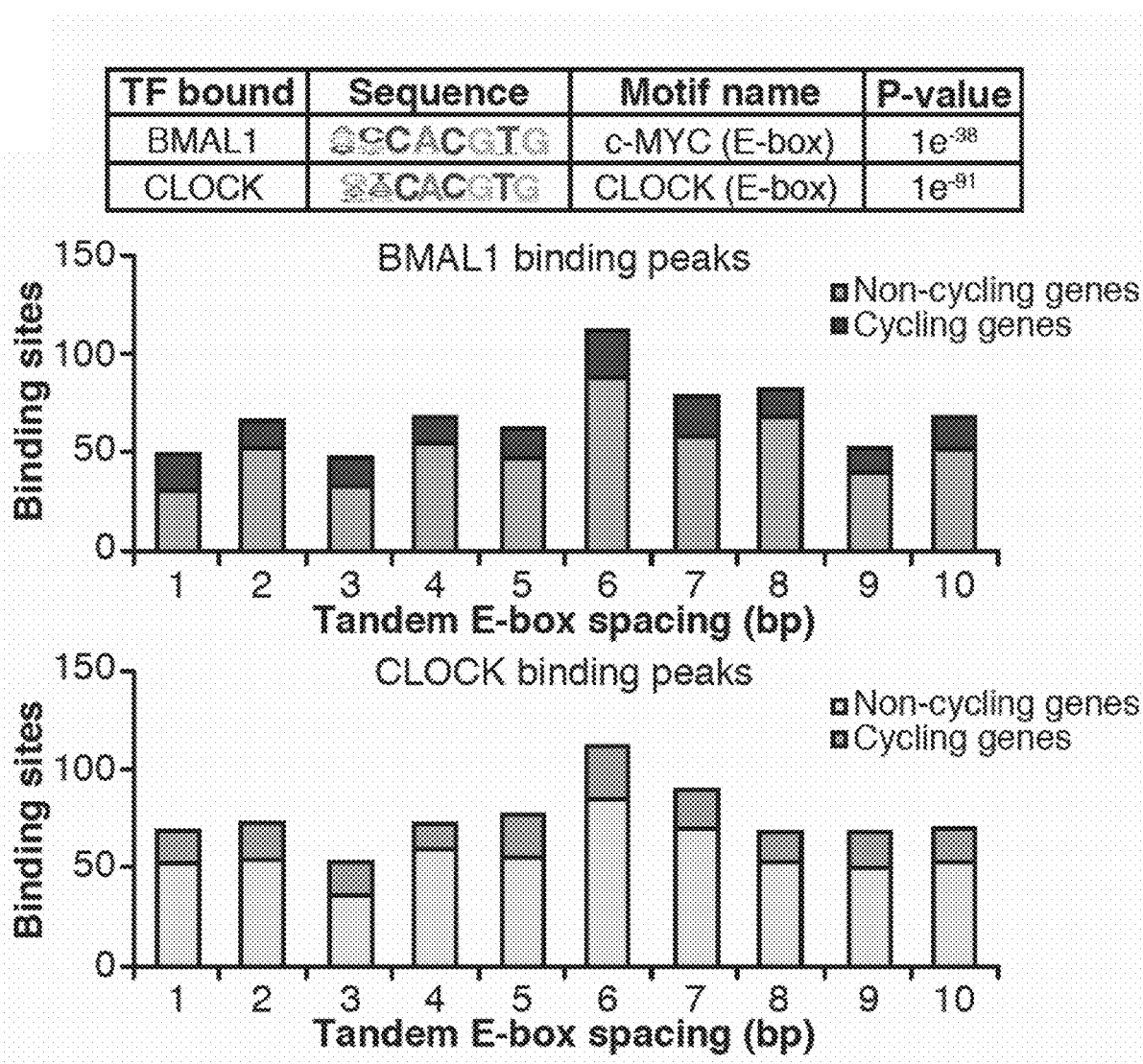
FIGS. 9A-9F show that BMAL1 and CLOCK bind distinct enhancer regulatory regions genome-wide in β-cells compared to liver.

To determine whether the rhythmic islet transcriptome is conserved from mouse to humans, RNA-seq was performed in RNA isolated from synchronized human islets (FIG. 9A). Human islets displayed characteristic circadian patterns in the expression of core clock components BMAL1 and REV-ERBα (FIG. 8B) (29) and genome-wide rhythmic patterns in the transcriptome with 1800 cycling RNAs (Bonferroni-corrected P<0.05) (FIG. 8B). Although striking differences have been described between mouse and human islet cell composition and cytoarchitecture (30), the expression of key genes involved in insulin release is conserved between species (30). In fact, 481 of the rhythmic human islet genes were orthologous to those in mouse islets (FIG. 8C), including factors involved in exocytosis, trafficking, and fusion (FIGS. 1, E and F, and FIG. 8C). Mapping cycling human islet RNAs onto KEGG-curated human insulin secretion pathways revealed regulation of heterotrimeric G protein-coupled receptor (GPCR), cAMP, Ca2+, and phosphoinositide-responsive signaling molecules important in nutrient response and hormone release (FIGS. 1, E and F). Specifically, these included GNAQ (Gq protein), RIMS2 and PCLO (insulin vesicle-associated), CAMK2G (calmodulin-activated protein kinase), and PLCB4 (phospholipase C), all of which were also rhythmic in mouse islets (FIGS. 1, E and F, and FIG. 8D). Circadian gene regulation in the endocrine pancreas of both mice and humans thus converges on the late secretory pathway, demonstrating conservation of clock control of rhythmic tissue function across species.

BMAL1 and CLOCK Bind Near Cell Type-Specific Enhancers in Pancreatic β Cells

Figure 2A:
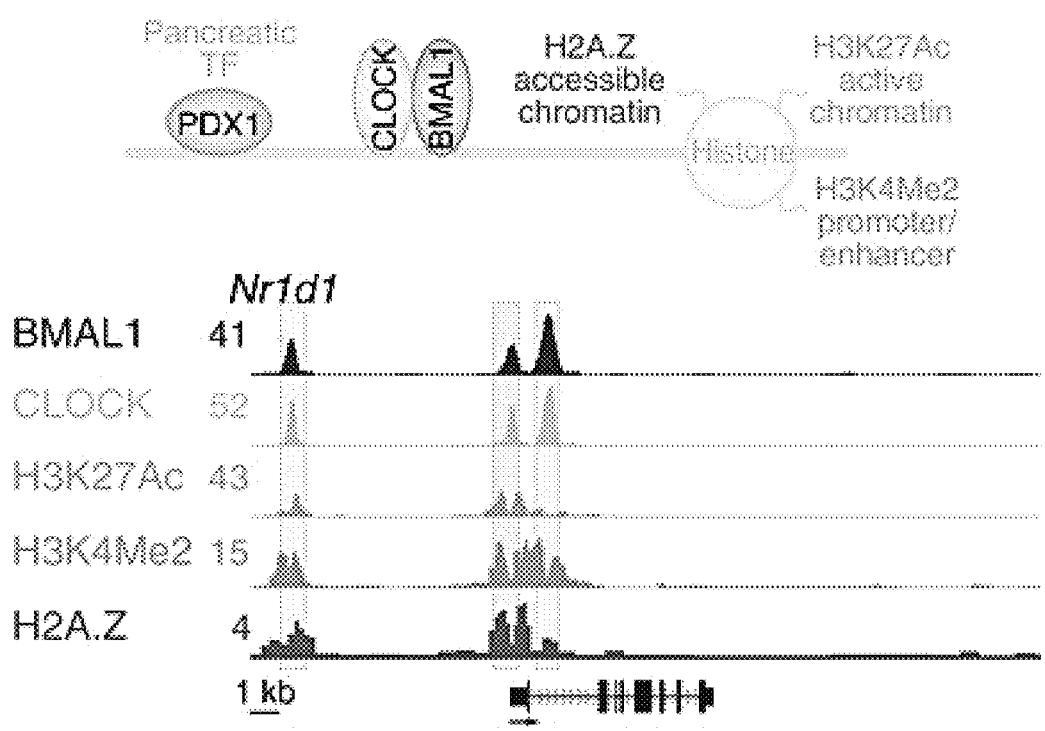
FIGS. 2A-2C show that BMAL1 and CLOCK bind to cycling genes at distal regulatory sites.
Figure 9B:
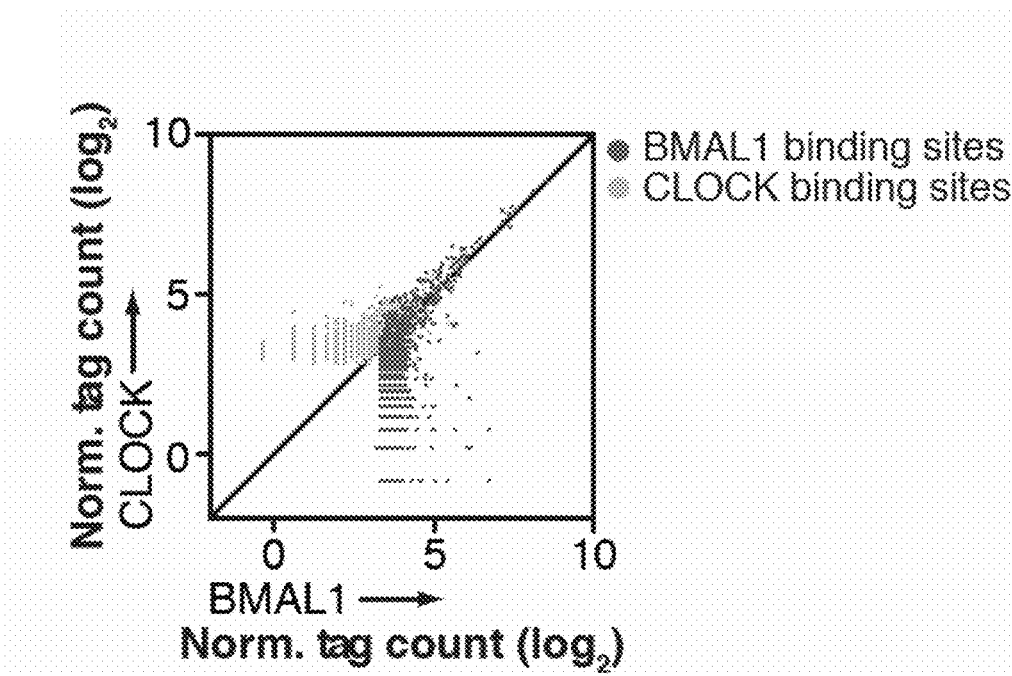

Because genome-wide RNA sequencing studies indicate that genomic regulation by the clock gives rise to rhythmic insulin secretion, it was next analyzed how core circadian transcription factors regulate this process by analyzing the extent of binding by BMAL1 and CLOCK to rhythmically expressed genes. In this context, cistrome studies have recently characterized β cell transcriptional hubs encoding genes that program both development and function (31), revealing colocalization within regions of accessible chromatin (H2A.Z) and active enhancers [monomethylated histone 3 Lys4 (H3K4Me1) colocalized with acetylated histone 3 Lys27 (H3K27Ac)] containing binding sites for lineage-determining transcription factors (PDX1, MAFB, FOXA2, NKX6-2, and NKX2-2) (31-33). To determine the intersection between circadian transcription factor regulation and genomic binding at regulatory loci, chromatin immunoprecipitation sequencing was performed (ChIP-seq) in the mouse β cell line Beta-TC6 (FIG. 2A). Both BMAL1 and CLOCK physically bound to sites at core clock and other gene targets in β cells that were enriched for the canonical CACGTG E-box motif, often occurring in tandem, as previously reported at BMAL1 binding sites in liver (FIG. 9A) (P=10-38 and P=10-91, respectively) (9, 34). Moreover, we also observed a correlation between the genome-wide binding of BMAL1 and CLOCK (FIG. 9B). A representative UCSC Genome Browser track at the Rev-erbα (Nr1d1) locus is shown in FIG. 2A, revealing colocalization of BMAL1 and CLOCK binding sites at three distinct regulatory regions at the Nr1d1 locus, including within the promoter region [shaded light orange and defined as within 2 kb of the transcription start site (TSS)] and within intragenic and intergenic distal enhancer regions (shaded light green and defined as binding regions greater than 2 kb from the TSS). Histone markers representing active and accessible chromatin (H3K27Ac and H2A.Z, respectively) localized to the same promoter and enhancer regions within the Nr1d1 locus, indicating active transcriptional regulation by BMAL1 and CLOCK (FIG. 2A).

Figure 9C:
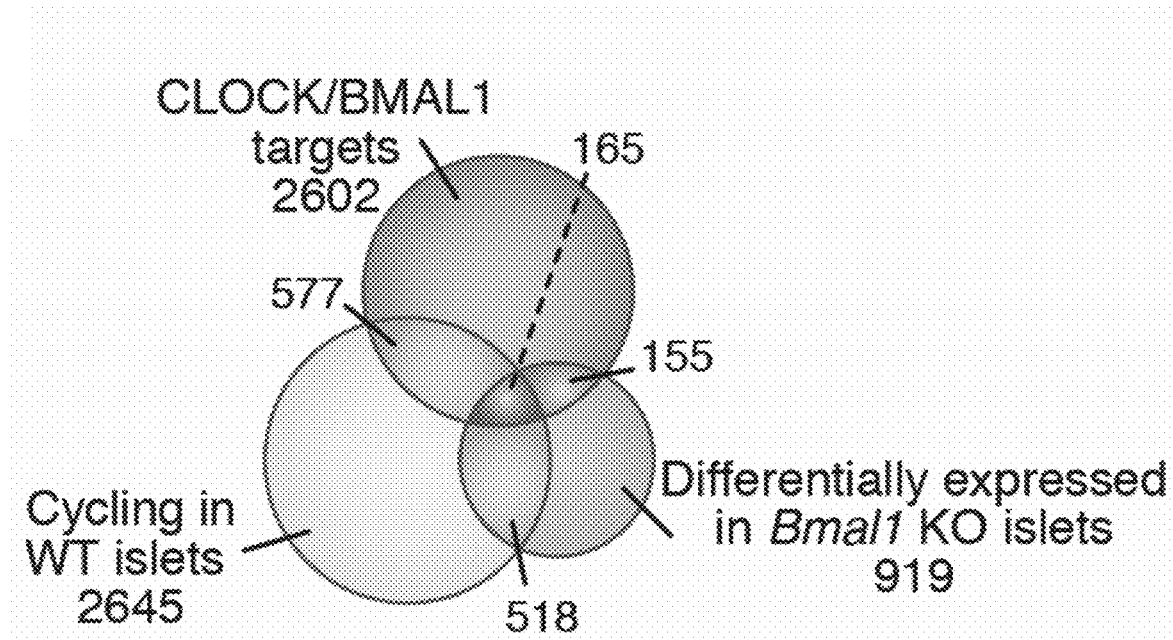

To determine whether BMAL1 and CLOCK directly regulate the oscillating transcripts identified in the synchronized wild-type islets (FIG. 1C), the overlap between the BMAL1 and CLOCK cistromes with genes oscillating in the wild-type islets was evaluated. Among binding sites localized to expressed RNAs, 30% (862 binding sites) and 29% (330 binding sites) of the BMAL1 and CLOCK targets, respectively, exhibited rhythmic transcription in synchronized wild-type islets (FIG. 2B), which collectively accounted for 742 cycling direct target genes, of which 165 were differentially expressed in Bmal1 knockouts (FIG. 9C). These findings show direct BMAL1 and CLOCK regulation. Moreover, KEGG analysis of the direct gene targets in mouse islets that were present in BMAL1 and CLOCK cistromes revealed enrichment in pathways related to protein export, COPII-mediated vesicle budding from the endoplasmic reticulum, and SNARE vesicular transport and membrane fusion, in the cycling set relative to the noncycling set of BMAL1- and CLOCK-controlled transcripts (KEGG pathways listed in order of descending −log 10 P values in FIG. 2C and table 1). Together, these findings identify direct transcriptional targets of CLOCK/BMAL1 that mediate rhythmic islet physiology.

BMAL1 Binds to Distinct Enhancers in Liver and Pancreatic β Cells

Figure 2B:
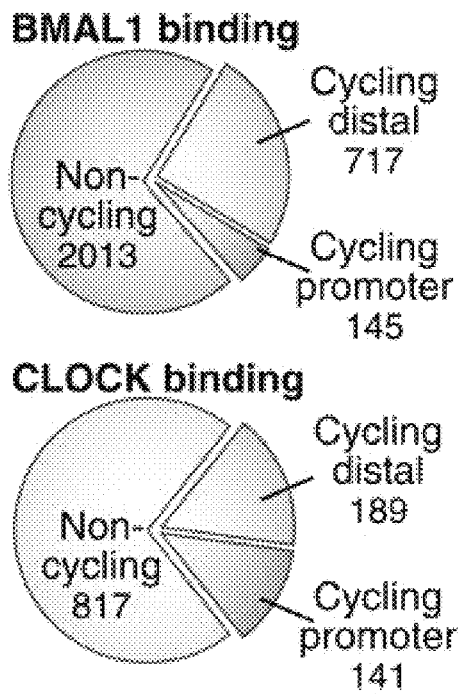
Figure 2C:
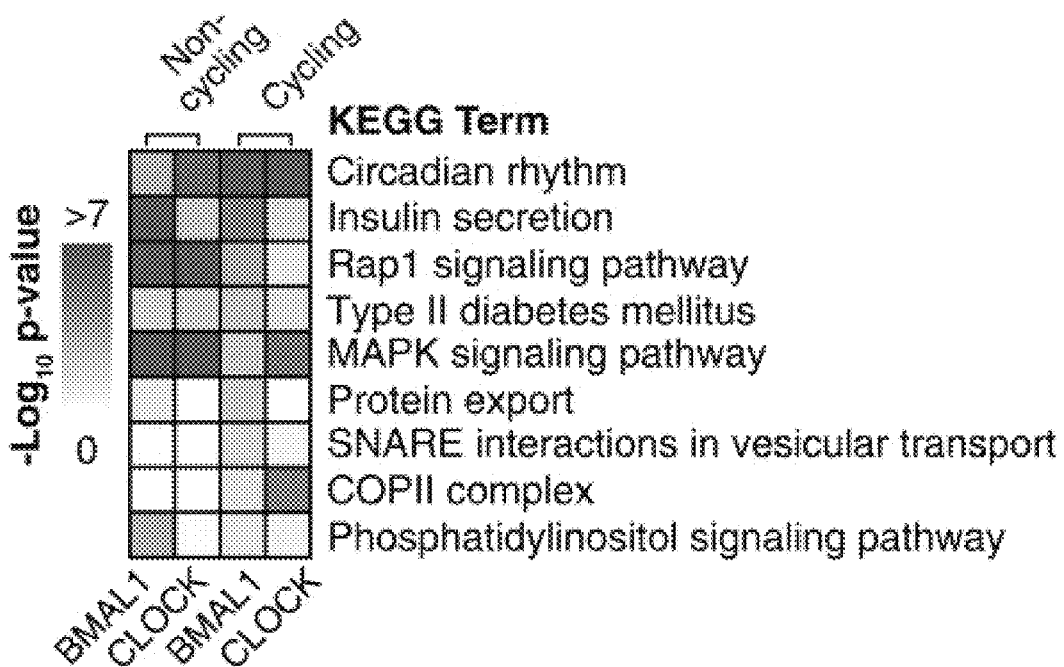
Figure 9D:
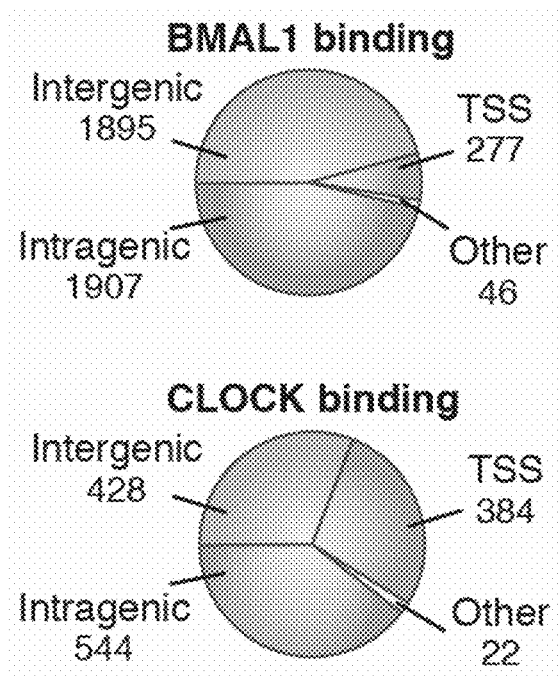

Given evidence for tissue-specific regulation at enhancers as a predominant mode of circadian regulation in liver (10), the binding position of BMAL1 and CLOCK in relation to the TSS of rhythmic genes in β cells was examined. Because genome-wide promoter activity studies and epigenetic characterization of mammalian regulatory regions have indicated that the majority of core promoter activity is localized within 2 kb of the TSS (35-37), binding events occurring within 2 kb of the nearest annotated gene TSS were classified as promoter-proximal. IT was found that BMAL1 and CLOCK bind predominantly at distal sites (defined as greater than 2 kb from the TSS) rather than at proximal promoter sites (defined as less than 2 kb from the TSS) of rhythmically regulated genes (FIG. 2B and FIG. 9D). This finding shows that the islet clock transcription factors affect rhythmic physiology through binding to distal regulatory sites, an observation concordant with the general finding that transcription factors exert physiologic effects through regulation within tissue-specific enhancers (31).

Figure 3A:
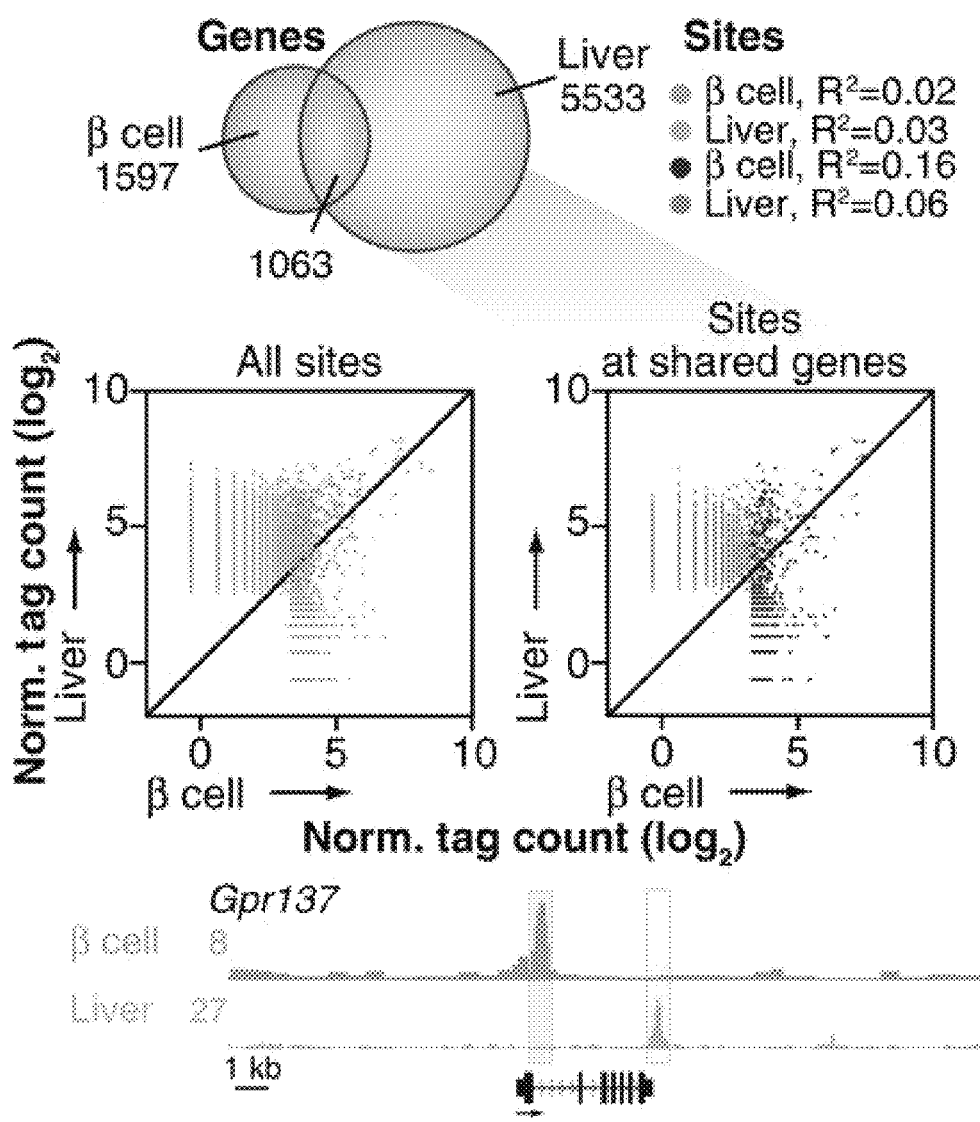
FIGS. 3A-3D show that β cell circadian cistrome is determined by tissue-specific enhancer repertoire.
Figure 3B:
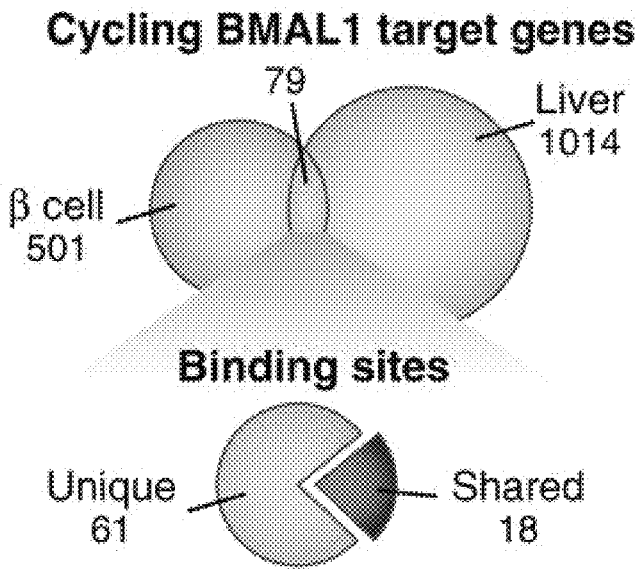
Figure 9E:
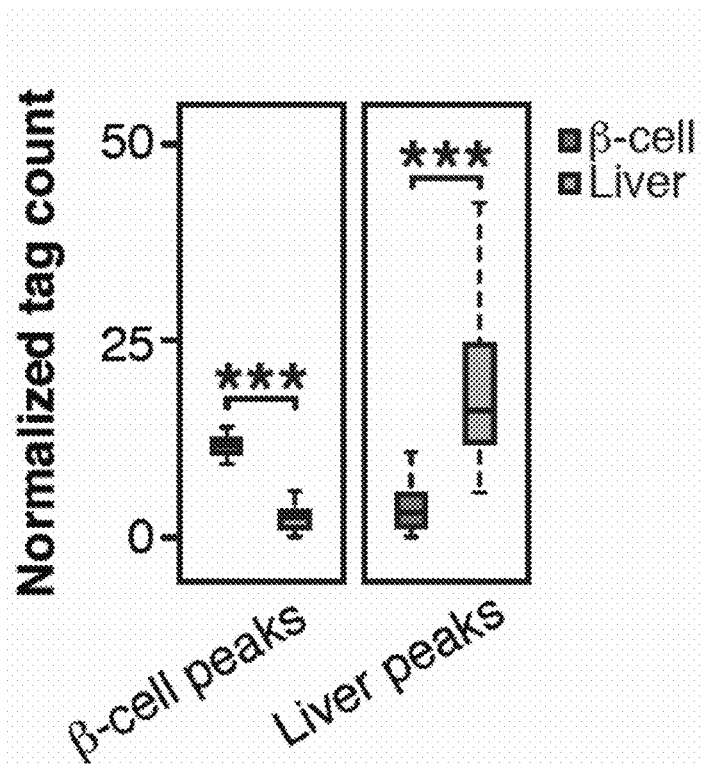
Figure 9F:
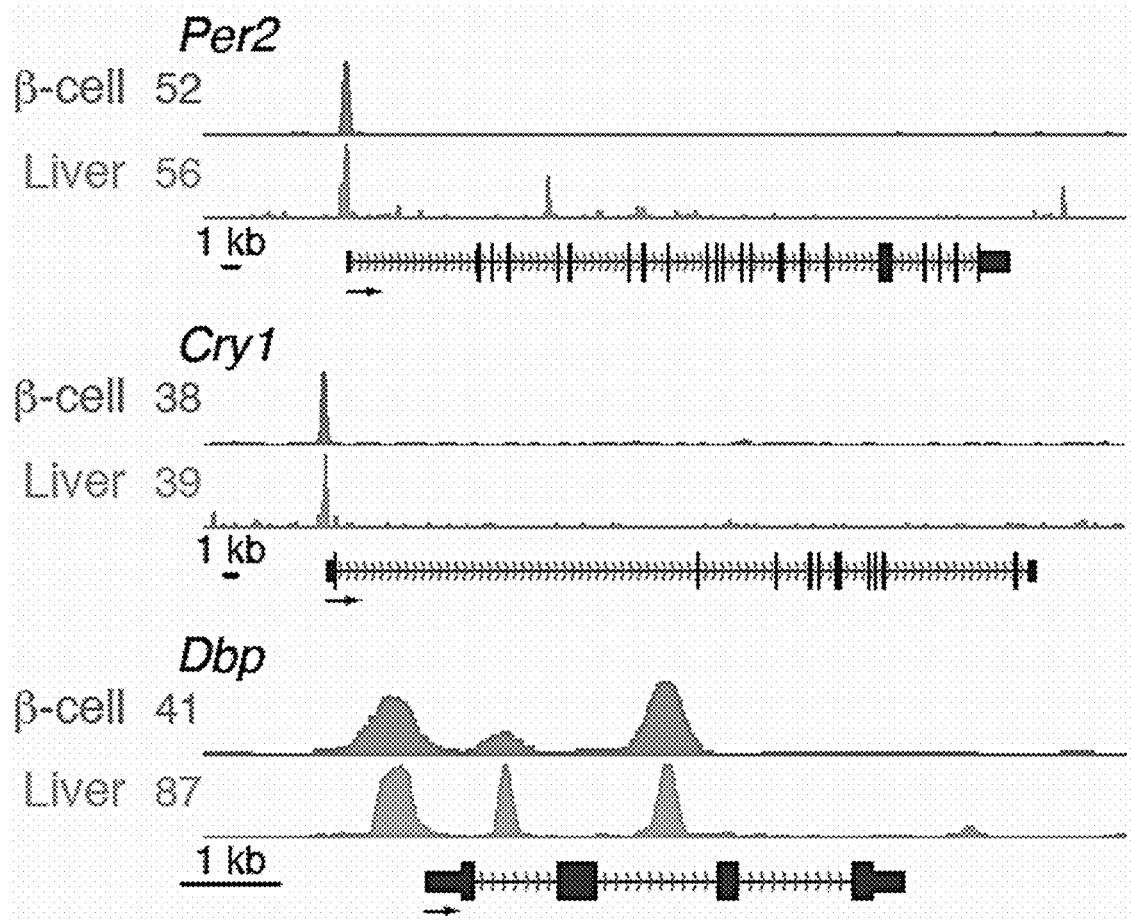

Although clock factors have been shown to exert distinct physiologic functions across tissues, a major gap remains in understanding the underlying genomic mechanisms accounting for these tissue-specific functions. To determine whether BMAL1 regulates rhythmic genes through unique sites in the β cell compared to liver, the tissue in which the circadian cistrome has been best characterized (9-11, 34, 38), sites of BMAL1 occupancy in the β cells were compared to a published set of liver BMAL1 peaks (9). Unexpectedly, although there was a considerable overlap of genes identified as direct BMAL1 binding targets in β cells and liver (40%, 1063 genes out of 2660 total β cell target genes) (FIG. 3A), BMAL1 binding at the regulatory regions of those shared gene sets localized to distinct sites (FIG. 3A). In comparing genome-wide binding patterns, common locations of binding were observed in only 4% of these instances; thus, BMAL1 binding at all β cell-defined sites is uncorrelated with BMAL1 binding at all liver-defined sites (FIG. 3A and FIG. 9E) ($R^2$=0.01874 and 0.03286 for BMAL1 binding at β cell and liver sites, respectively), whereas binding at canonical E-box sites in Per2, Cry1, and Dbp was similar between tissues (FIG. 9F). Furthermore, when the shared set of BMAL1 target genes that were rhythmic in islets and also reported to be rhythmic at the mRNA level in liver were compared, BMAL1 likewise bound to unique sites (9) (FIG. 3B). These data support convergent regulation of BMAL1 targets in β cell and liver sites through divergent regulatory elements.

Figure 3D:
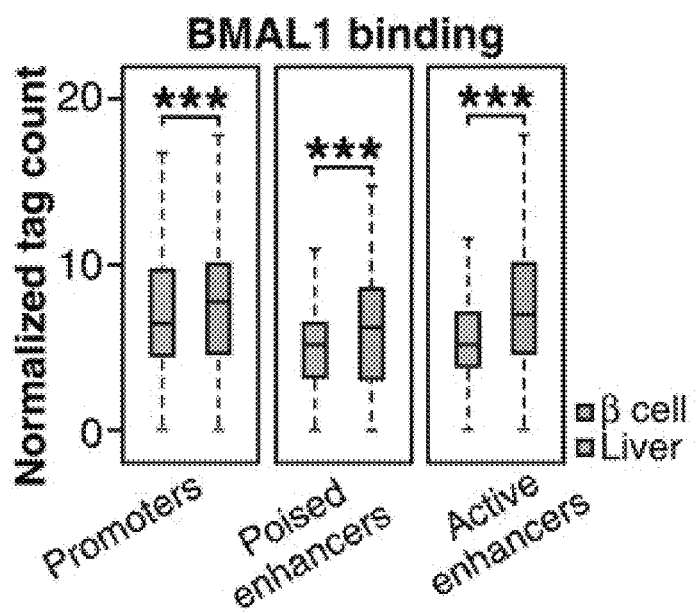
Figure 3C:
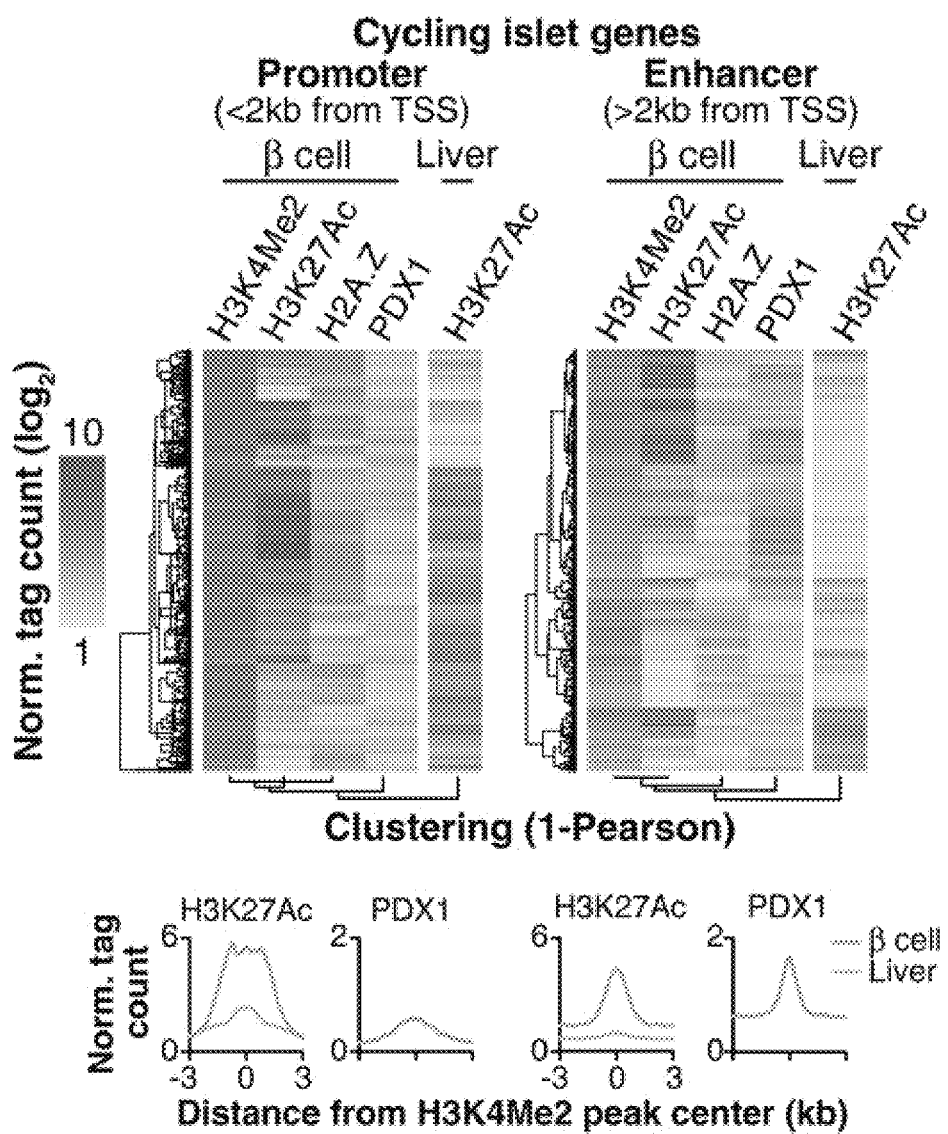
Figure 4A:
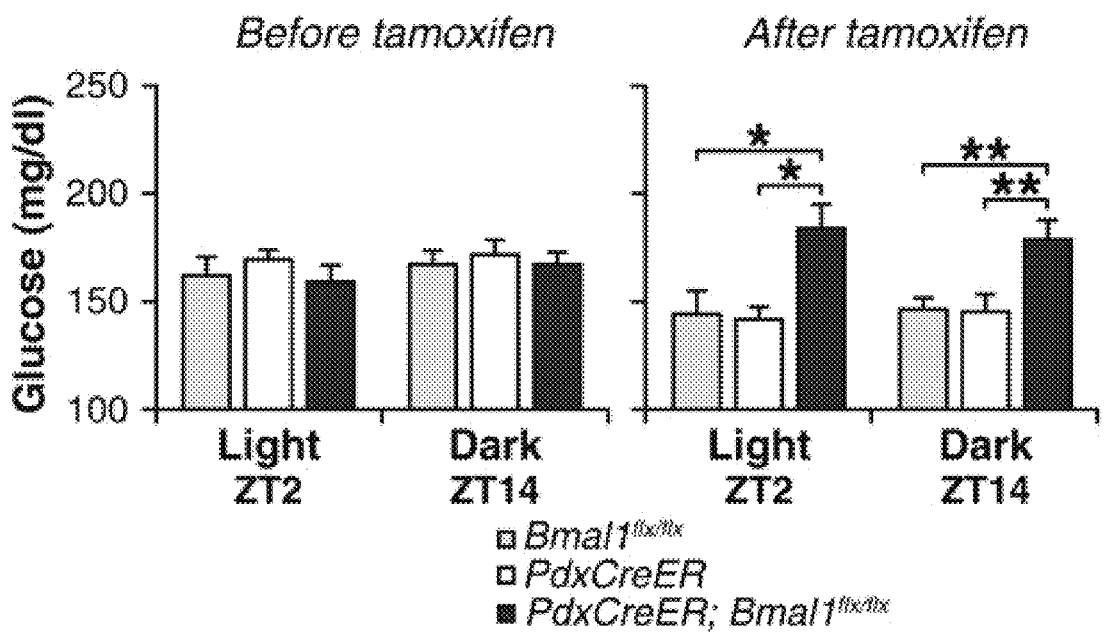
FIGS. 4A-4F show that clock disruption in β cells during adulthood causes acute hypoinsulinemic diabetes in mice.
Figure 4E:
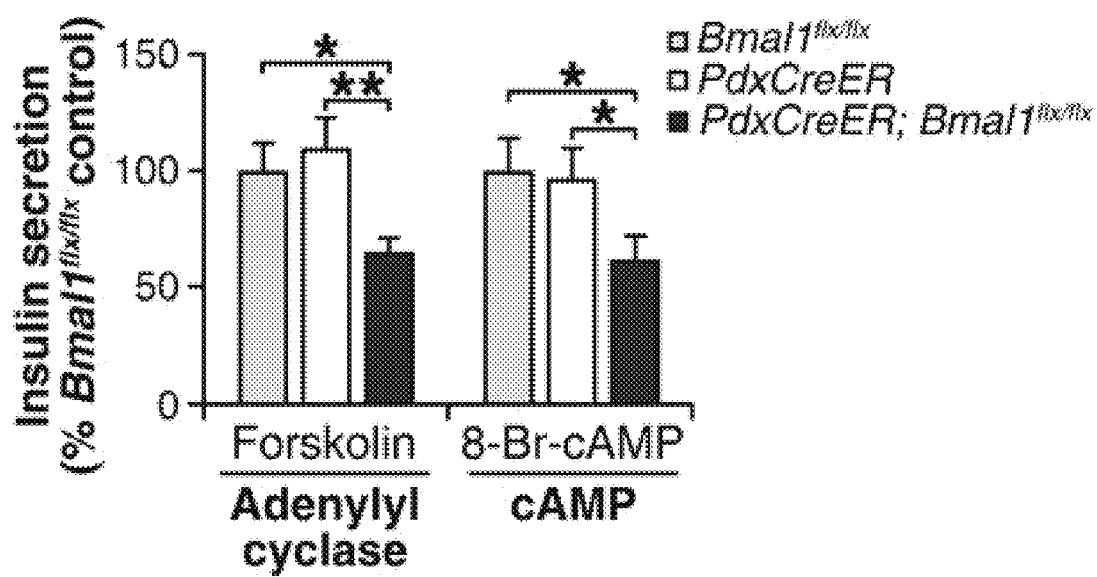
Figure 4B:
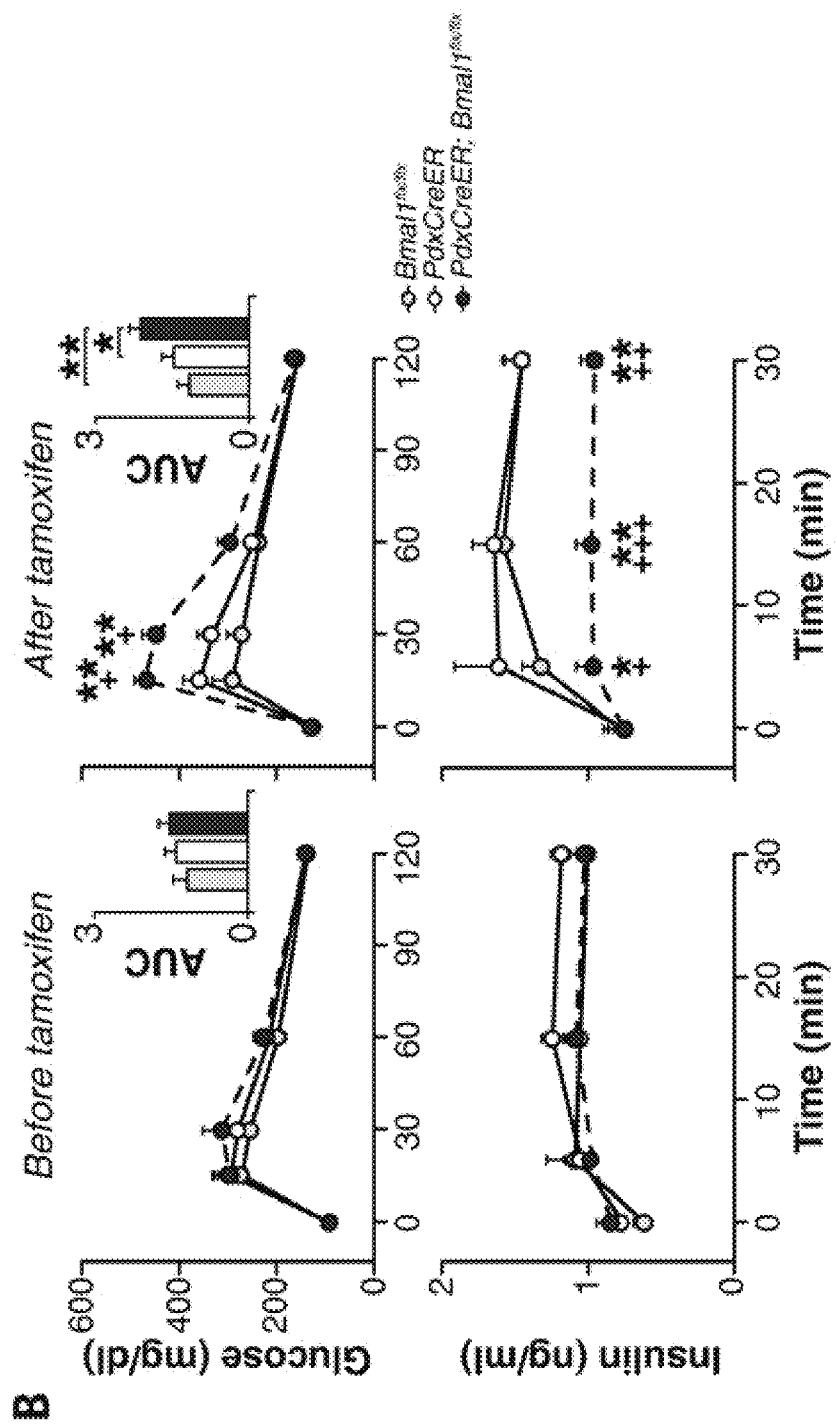
Figure 4C:
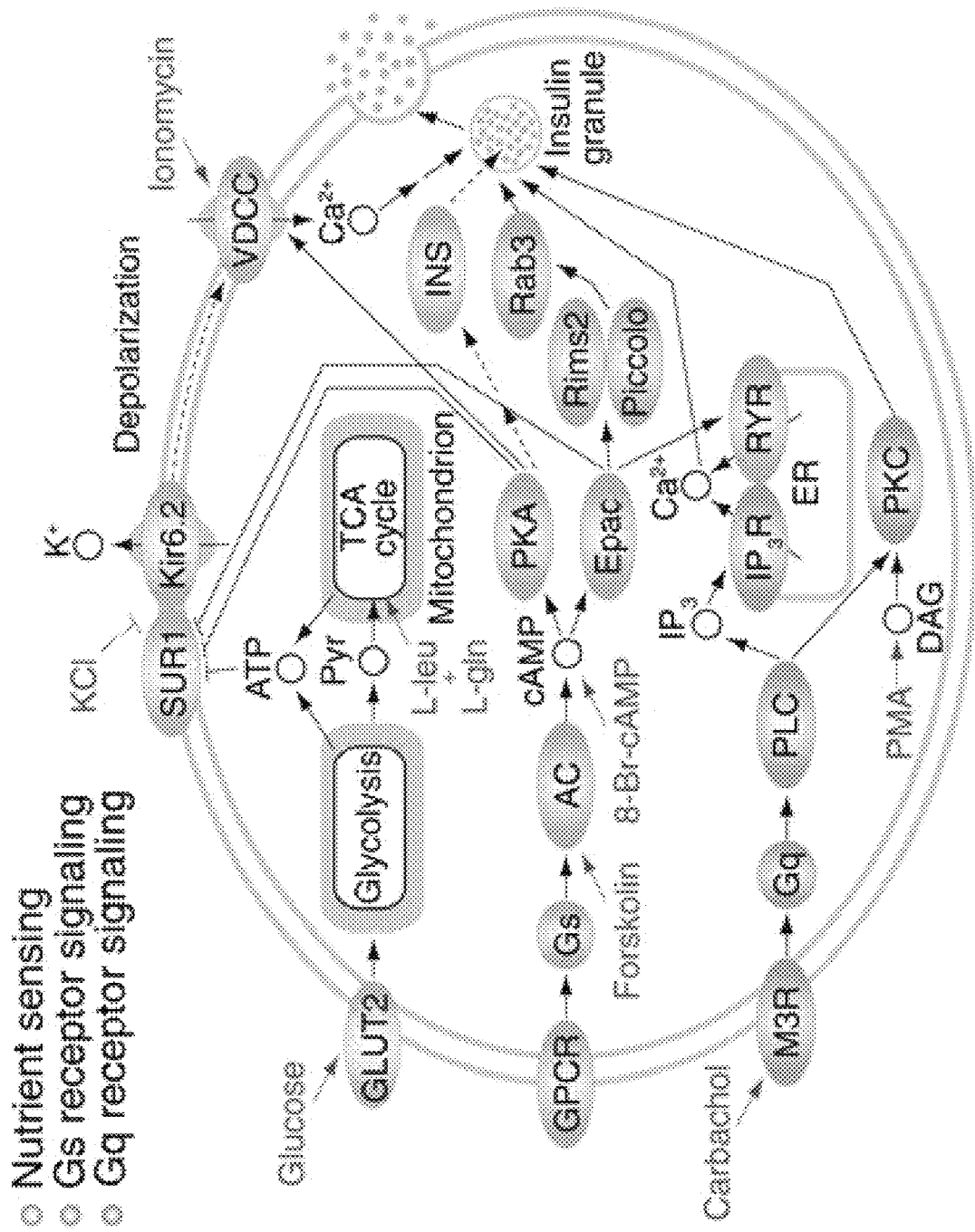
Figure 4D:
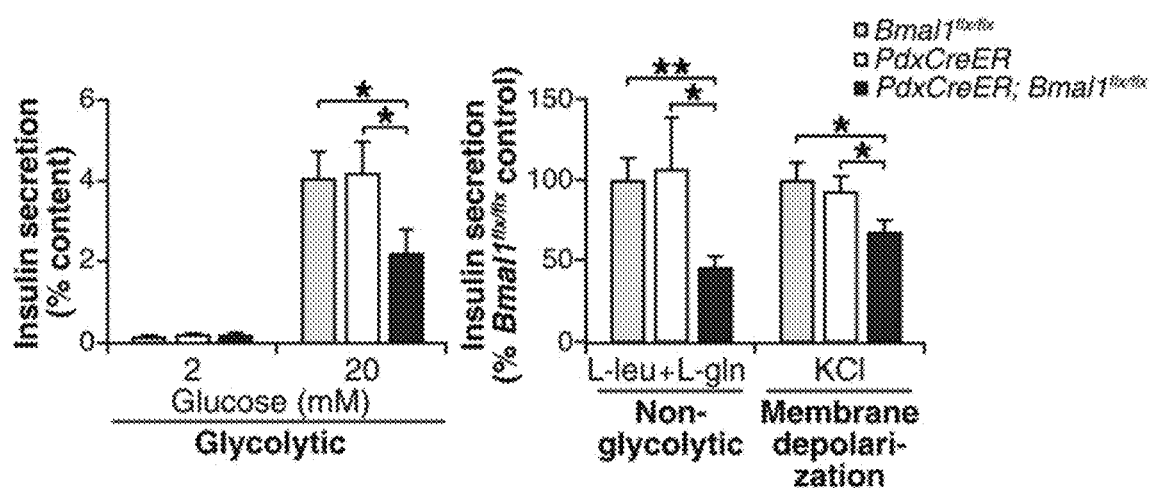
Figure 4F:
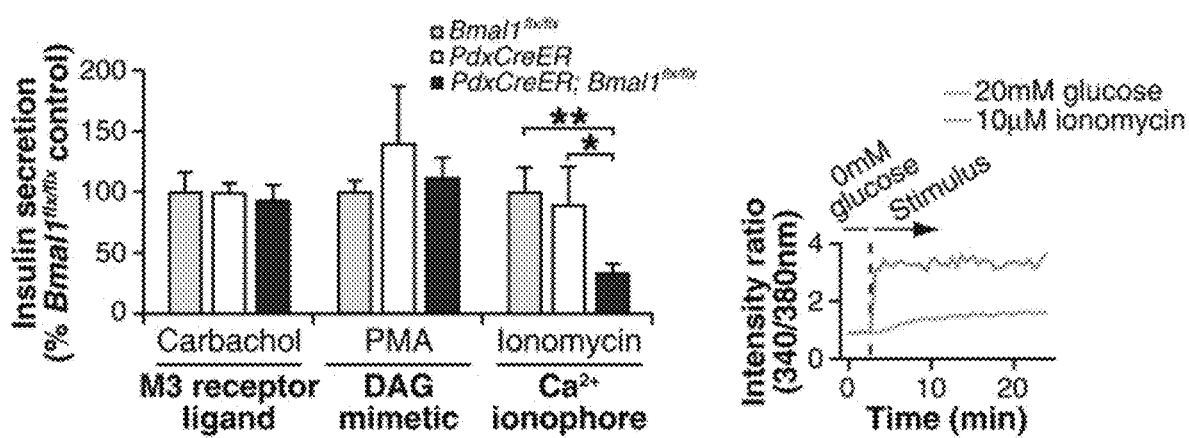
Figure 10A:
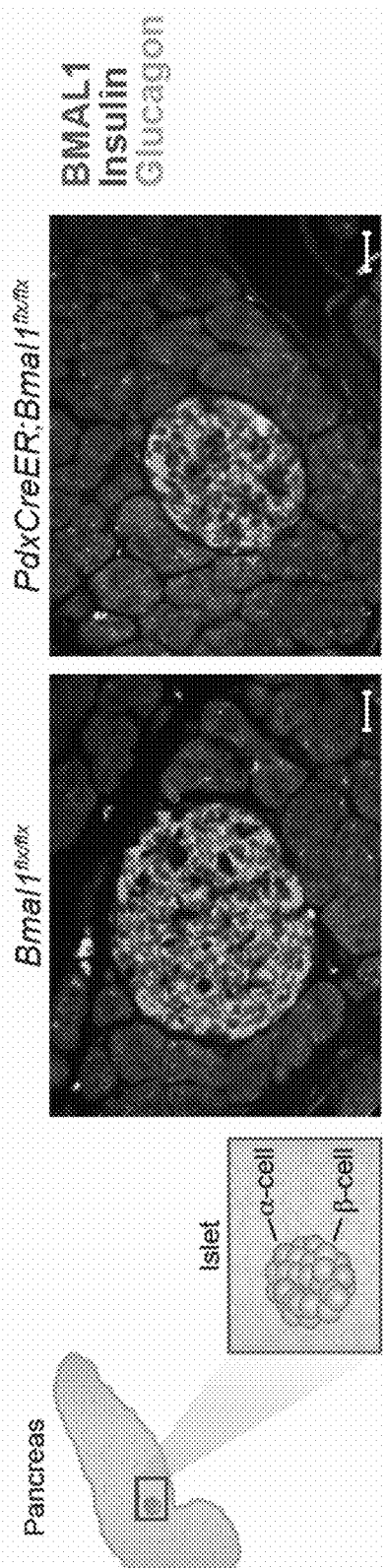
FIGS. 10A-10C show that Tamoxifen-induced adult-life Bmal1 deletion is limited to pancreatic β-cells.
Figure 10B:
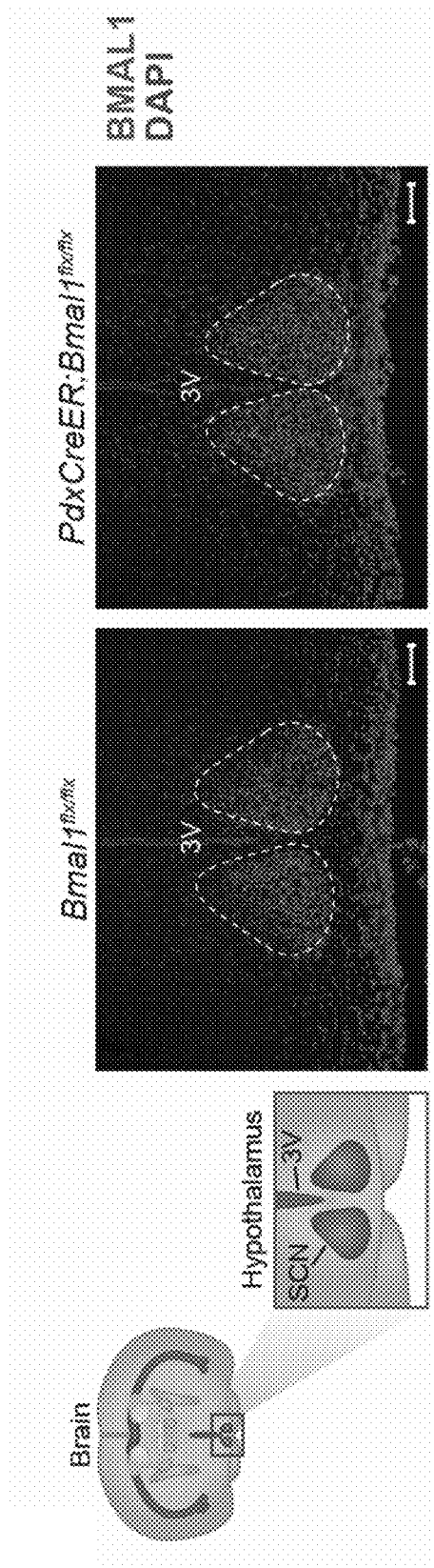
Figure 10C:
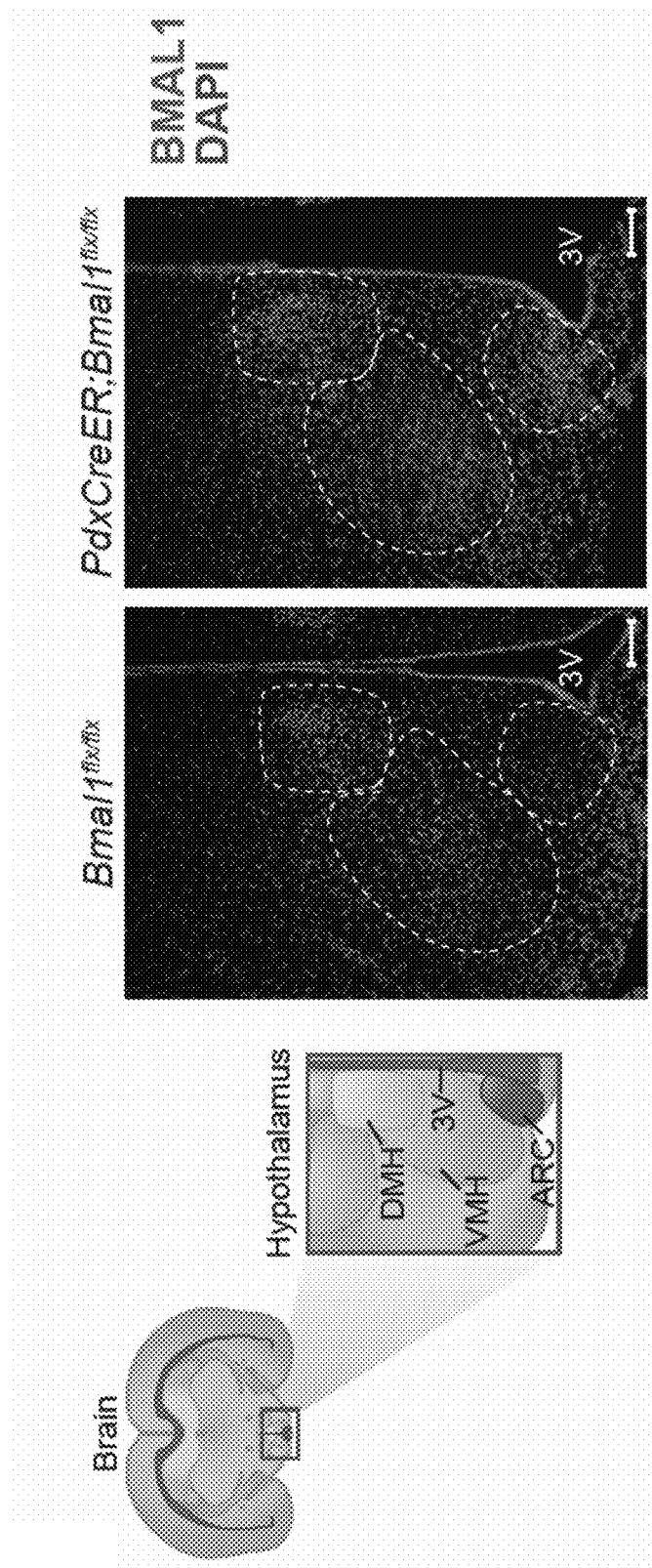
Figure 11A:
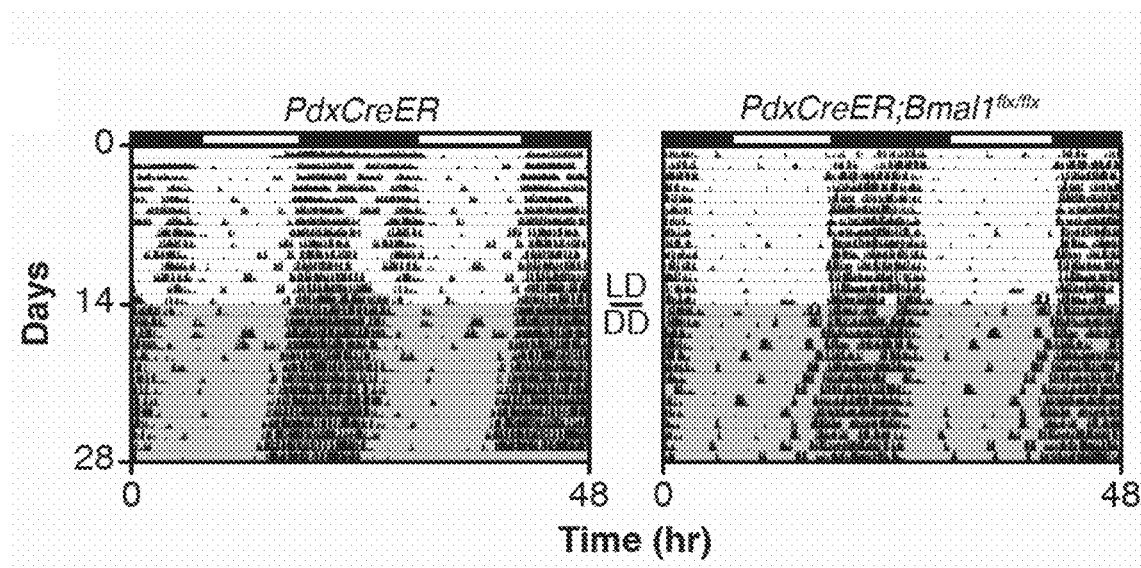
FIGS. 11A-11E show that adult-life pancreatic β-cell-specific loss of BMAL1 does not impact behavior, feeding, or body weight.
Figure 11B:
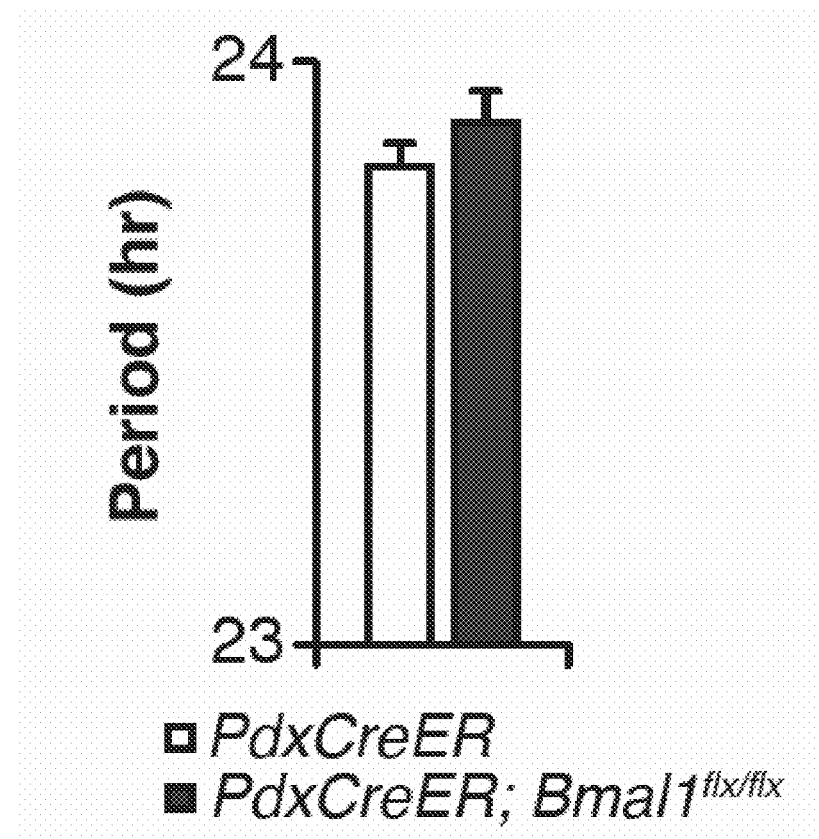
Figure 11C:
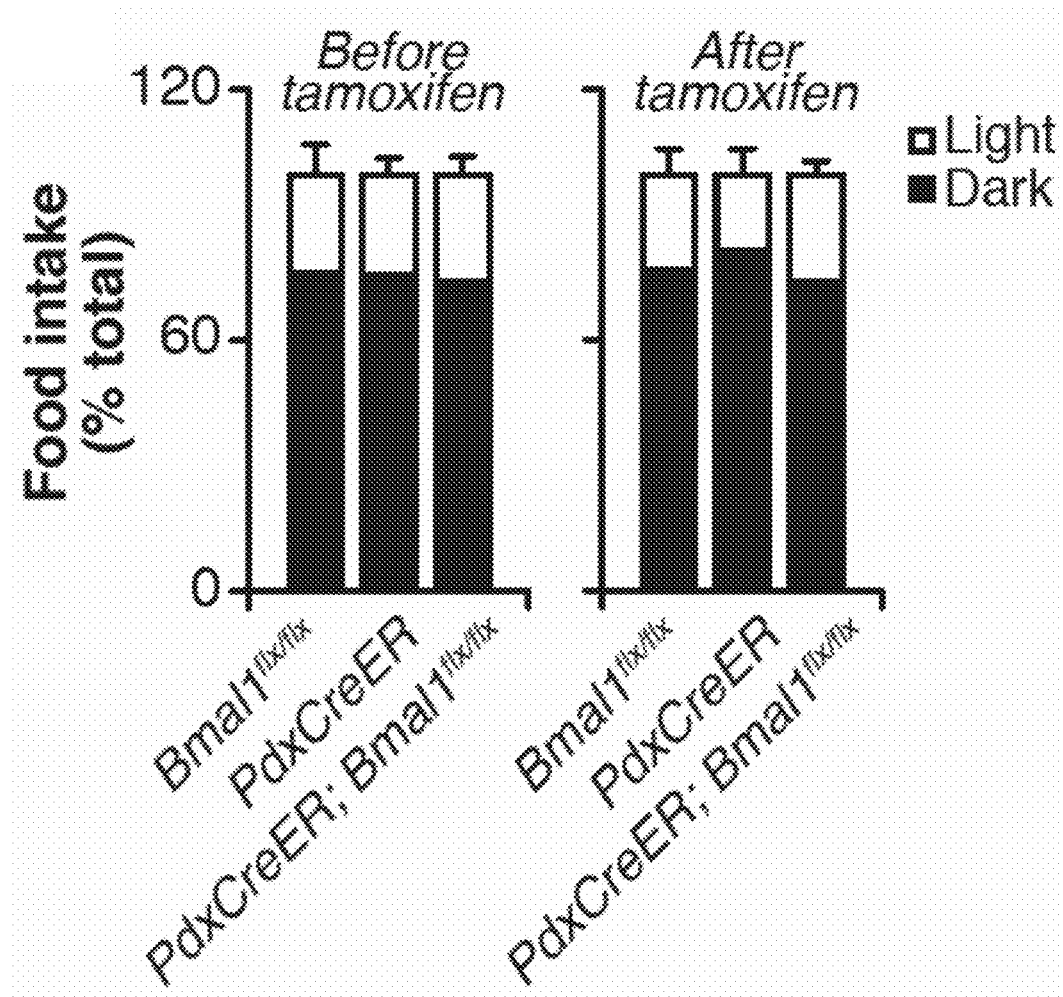
Figure 11D:
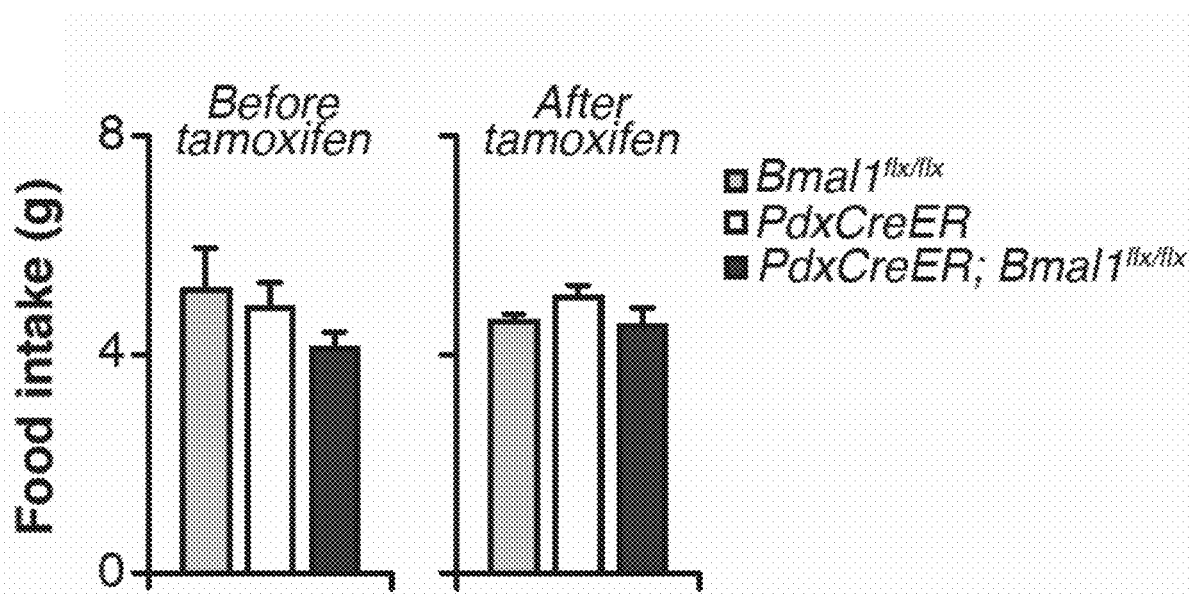
Figure 11E:
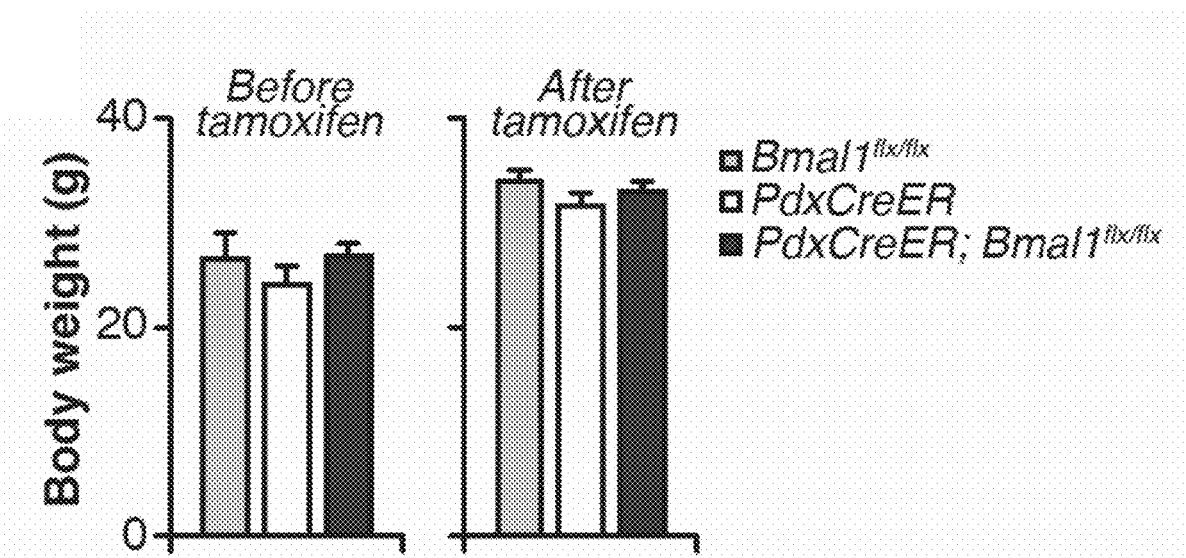
Figure 12:
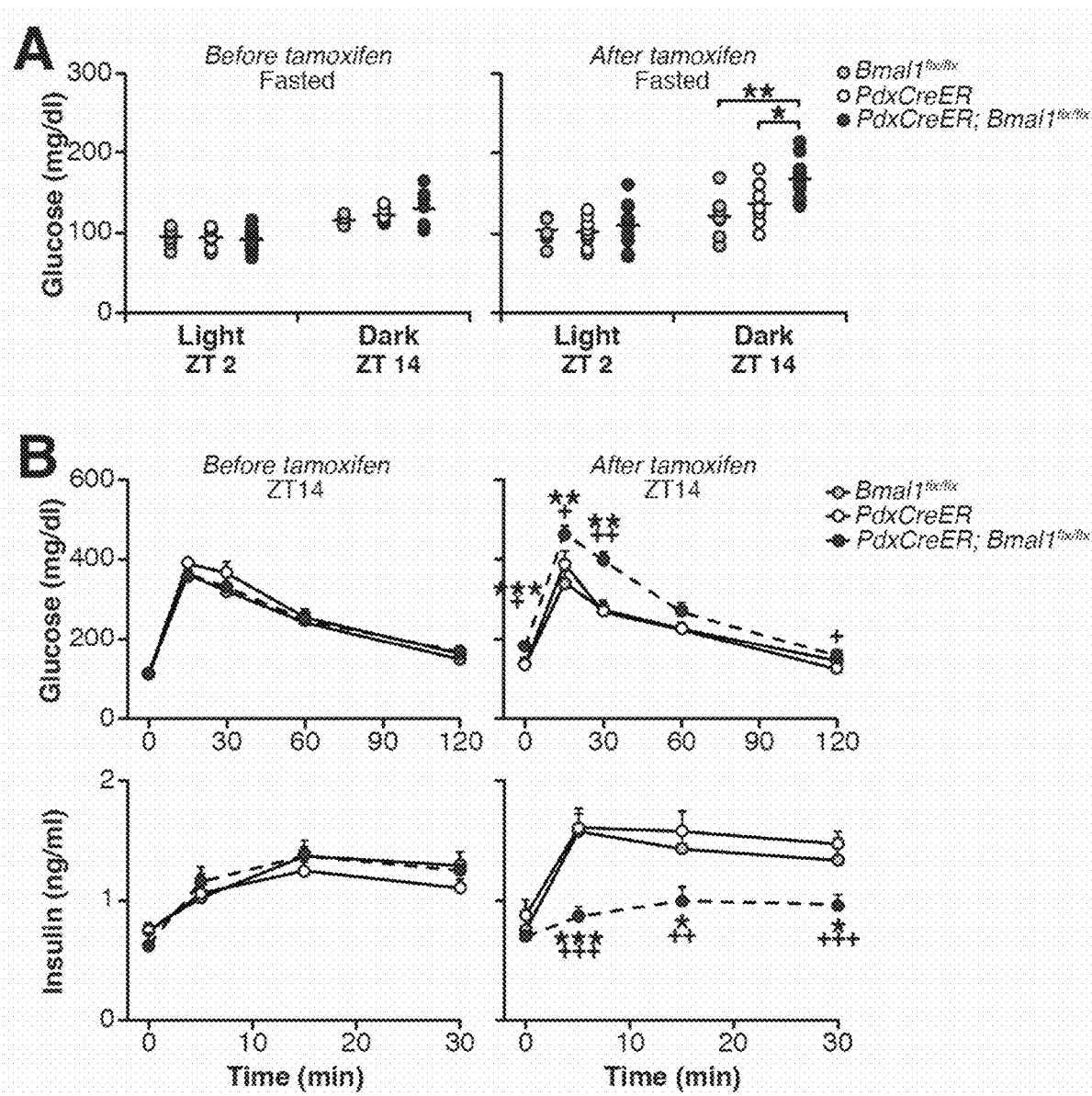
FIG. 12 shows that acute Bmal1 deletion in adult β-cells impairs glucose homeostasis. (Panel A) Fasting glucose in PdxCreER;Bmal1flx/fix and littermate control mice before and after tamoxifen treatment (n=7-11 mice per genotype). (Panel B) Glucose tolerance and insulin secretion at ZT14 following intraperitoneal glucose administration of 2 and 3 g/kg body weight, respectively, in PdxCreER;Bmal1flx/fix mice and littermate controls before and after tamoxifen treatment (n=4-10 mice per genotype). *$p<0.05$, $p<0.01$, *$p<0.001$.
Figure 13:
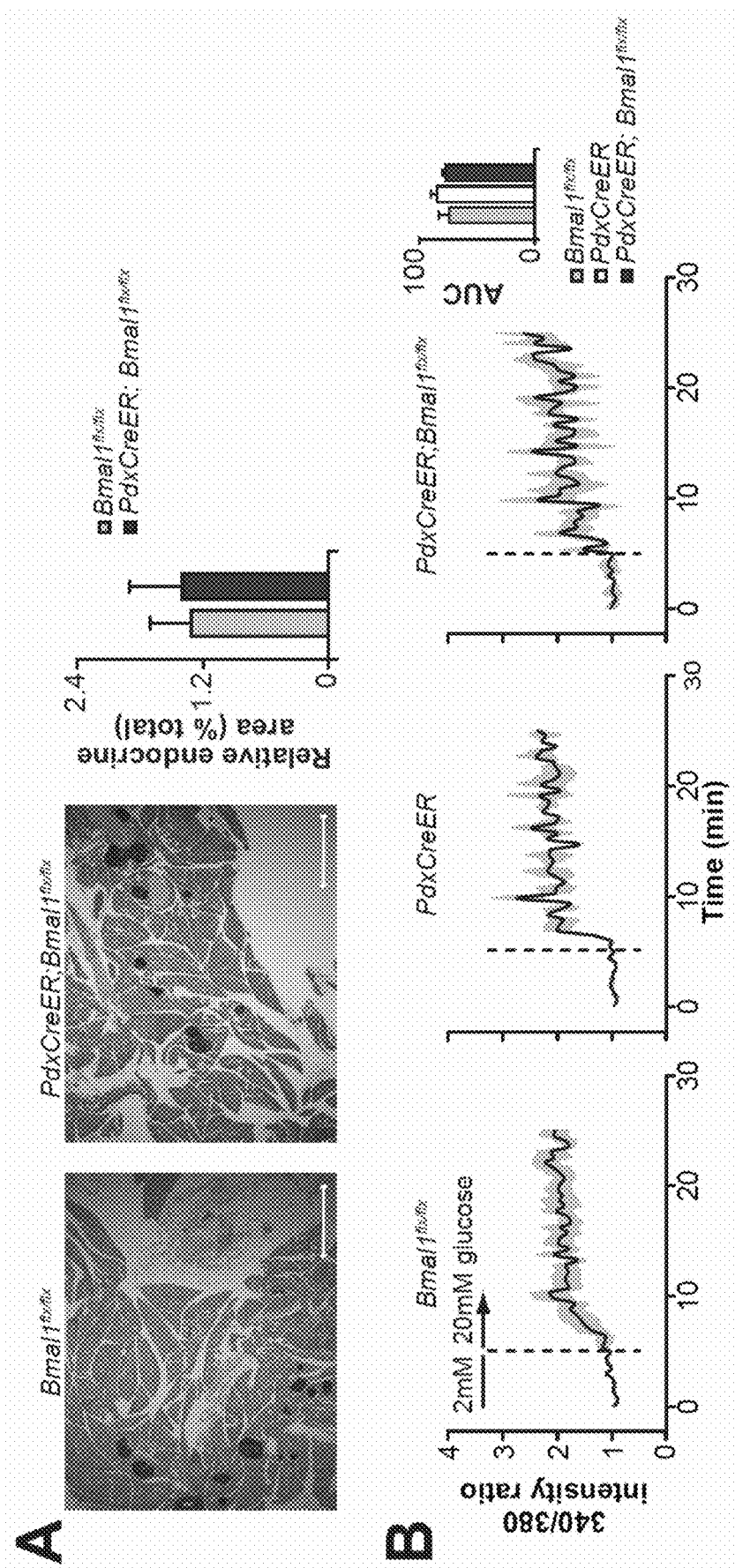
FIG. 13 shows islet mass and glucose-stimulated calcium influx are normal in adult-life Bmal1 knockout islet cells. (Panel A) Morphometric analysis of insulin-positive area in the pancreas of PdxCreER;Bmal1flx/flx and Bmal1flx/fix control mice (n=3 mice per genotype). Scale bars, 1000 μm. (Panel B) Ratiometric determination of intracellular Ca2+ using Fura2-AM dye in islets isolated from PdxCreER, Bmal1flx/flx, and PdxCreER;Bmal1flx/fix mice following ex vivo challenge with 20 mM glucose, where the dashed line indicates the time when glucose was injected (left) and area under the curve (right) (n=2-4 mice per genotype). All values represent mean±SEM.

Because BMAL1 predominantly bound at distal regulatory regions in islets that were divergent from liver, the chromatin regulatory context at all cycling genes in β cells was examined by defining all regulatory regions at cycling loci using dimethylated histone 3 Lys4 (H3K4Me2) peaks within 2 kb of the TSS (promoter) and more than 2 kb from the TSS (enhancer) (FIG. 3C). The binding patterns of the histone marks H3K4Me2, H2A.Z, and H3K27Ac (which represent promoter/enhancer regulatory regions, chromatin accessibility, and enhancer activity, respectively), as well as binding of the lineage-determining transcription factor for β cells PDX1 (39) at promoters and enhancer regions, are displayed in heat maps in FIG. 3C. Hierarchical clustering revealed that all epigenetic and PDX1 signals at promoter and distal enhancer regions at cycling genes more frequently displayed correlated binding than did H3K27Ac at these loci in liver, as indicated by the clustering dendrogram (FIG. 3C). Accordingly, the genomic coordinates in liver corresponding to enhancers defined in β cells displayed markedly reduced H3K27Ac, indicating that these enhancers defined specific loci of β cell regulation (FIG. 3C). Frequent binding of PDX1 at distal enhancer loci suggested that tissue specificity arose from early events in islet cell development (FIG. 3C) (40). Consistent with tissue-specific clock transcription factor regulation at β cell regulatory regions, BMAL1 displayed a greater degree of binding to promoter and enhancer regions at cycling genes in β cells than in liver, particularly at active enhancers containing both H3K4Me2 and H3K27Ac (FIG. 3D). These results indicate that clock transcription factors generate unique patterns of rhythmic RNA expression across tissues according to the pattern of cell-specific enhancer repertoires and provide a molecular basis for the distinct and opposing effects of the clock in pancreas and liver, which primarily affect postprandial and fasting glucose metabolism, respectively (5, 6).

β Cell Clock Disruption During Adulthood Impairs Insulin Secretion and Causes Diabetes To test the hypothesis that clock genes modulate genome-wide transcription on a daily basis throughout adult life, the impact of acute clock inhibition on glucose metabolism in PdxCreER;Bmal1flx/flx mice at 2 to 3 months of age after administration of tamoxifen was examined, which abrogates BMAL1 expression exclusively within the β cell (FIG. 10) (41). Although these mice displayed normal wheel-running rhythms, period length, food intake, and body weight (FIG. 11) relative to littermate tamoxifen-treated PdxCreER and Bmal1flx/flx animals, they developed significant hyperglycemia, impaired glucose tolerance, and hypoinsulinemia within 10 to 14 days after tamoxifen administration during both the day (ZT2) and night (ZT14) (FIGS. 4, A and B, and FIG. 12), despite no differences in islet mass (FIG. 13A). These results establish that circadian disruption in fully differentiated cells is sufficient to induce metabolic disease, independent of effects on early development.

It was further found that islets isolated from tamoxifen-treated PdxCreER;Bmal1flx/flx mice secreted significantly less insulin relative to littermate controls when exposed to (i) 20 mM glucose; (ii) 10 mM leucine combined with 2 mM glutamine, which bypasses glycolysis to trigger mitochondrial adenosine triphosphate (ATP) production; or (iii) 30 mM KCl, which chemically closes the KATP channel, thus inducing membrane depolarization distal to glucose metabolism and an increase in cytosolic calcium (FIGS. 4, C and D); glucose-stimulated calcium influx was unchanged between the two groups (FIG. 13B). These data are consistent with the observation that circadian oscillation in insulin secretory capacity is regulated downstream of KATP channel closure. Consistent with impaired Gs-coupled GPCR signaling, PdxCreER;Bmal1flx/flx islets also secreted significantly less insulin than controls in response to glucose together with the cyclase agonist forskolin and the nonhydrolyzable cAMP analog 8-br-cAMP (FIGS. 4, C and E).

The response to Gq-type GPCR signaling was tested by stimulating islets with the muscarinic agonist carbachol, the diacylglycerol (DAG) mimetic phorbol 12-myristate 13-acetate (PMA), and the Ca2+ ionophore ionomycin. Carbachol and PMA restored insulin secretion in PdxCreER;Bmal1flx/flx islets (FIGS. 4, C and F), whereas the response to ionomycin, which raised intracellular Ca2+ in β cells (FIG. 4F), was significantly reduced in mutants, indicating that the DAG arm of the Gq pathway restored second messenger signaling. DAG regulates exocytosis in β cells and other neurosecretory cells by acting as a ligand for the vesicle priming protein Munc13-1 (42) and protein kinase C (PKC), which phosphorylates and activates SNAP25 and MUNC18-1 to initiate vesicle fusion (43). Rhythmic RNA expression of the PKC-activating Rho and Rap GTPases Rho, Rhoa, Rhob, and Rap1a was observed in wild-type islets, which raises the intriguing possibility that elevated DAG concentrations in carbachol- or PMA-treated islets pharmacologically bypass a deficiency in Rho- and Rap-mediated signaling. Together, these results demonstrate that pharmacologic Gq agonism reverses the insulin secretory blockade induced by clock disruption, indicating convergence of cholinergic and phosphoinositol signaling within the β cell in temporal homeostasis.

This example describes the genome-wide basis of coordinated cross-tissue circadian oscillation through integrated studies of β cell physiology and cistrome regulation. Pancreatic β cells were studied as a paradigm of peripheral clock regulation of metabolism because clock disruption in the islet leads to severe hypoinsulinemic diabetes and has direct application to understanding human tissue rhythms and disease. Although the circadian system functions as a hierarchy in the intact animal, the results reveal organ-autonomous cycles of nutrient-coupled insulin secretion in isolated islets ex vivo that result in a high amplitude in maximal glucose responsiveness, showing that the clock primes insulin secretion within limited windows each day. It was further found that circadian-driven transcriptional oscillation within pancreas drives daily waves of expression of genes involved in the biogenesis, transport, and signal-induced activation of peptide exocytosis, indicating that genomic rhythmicity gives rise to tissue-specific function of the clock. The observations suggest that autonomous transcription cycles enable islet cells to anticipate diurnal changes in the demand for insulin.

Cistromic profiling within the β cell provides further insight into the regulation of tissue-specific genome oscillation. CLOCK and BMAL1 bind predominantly within distal tissue-specific enhancers rather than the promoters of cycling genes in proximity to H3K4Me2-, H2A.Z-, and H3K27Ac-modified nucleosomes that are co-occupied by PDX1. Consistent with tissue specificity in enhancer selection across cell types, BMAL1 binding in islet cells was highly divergent from liver, even within shared cycling target genes across the two tissues. These findings indicate that the establishment of accessible chromatin domains during development is a critical determinant of the available regulatory sites for clock-mediated transcription across distinct cell types.

Finally, studies using chemically inducible genetic clock inactivation demonstrate that inhibition of circadian signaling in differentiated β cells acutely blocks peptide exocytosis and leads to hypoinsulinemic diabetes, providing evidence that clock function throughout adult life is necessary for glucose constancy. It is contemplated that cell-autonomous genomic rhythms may regulate peptidergic secretion across diverse secretory and neuronal cell types, coordinating the availability of signaling molecules with the sleep/wake cycle each day. Furthermore, given the association between circadian and sleep disruption with human metabolic disease in both clinical (44, 45) and genetic (46) studies, the finding that circadian transcription is conserved in human islets suggests that clock dysregulation in β cells may contribute to the pathogenesis of human diabetes. The demonstration of coordinated circadian genomic and physiologic rhythms in pancreatic β cell insulin exocytosis and its control by enhancers provides a new window to understanding how geophysical and physiologic time are transcriptionally coupled, and how errors in this process may contribute to diabetes and other metabolic disorders.

TABLE 1

| KEGG Term | $-\log_{10} P$ value | Genes in Term | Target Genes in Term | Fraction of Targets | Gene Symbol |
|---|---|---|---|---|---|
| Cycling in wild type islets | | | | | |
| Circadian rhythm | 14.2992954 | 30 | 17 | 0.013832384 | Nr1d1, Prkaa2, Clock, Rorc, Rbx1, Npas2, Creb1, Rorb, Fbxw11, Per2, Rora, Per3, Prkag2, Arntl, Btrc, Prkaa1, Cry1 |
| Insulin secretion | 10.86222887 | 86 | 22 | 0.017900732 | Cacna1c, Atf2, Chrm3, Atf4, Prkacb, Slc2a2, Camk2g, Prkcb, Prkx, Plcb1, Prkca, Cacna1d, Kcnn4, Gnaq, Creb1, Creb3, Plcb4, Pclo, Kcnn3, Atp1b2, Rims2, Stx1a |
| SNARE interactions in vesicular transport | 10.86222887 | 33 | 16 | 0.013018714 | Sec22b, Gosr1, Vti1b, Vamp8, Vamp5, Stx8, Ykt6, Vamp1, Bnip1, Vti1a, Vamp4, Stx17, Use1, Stx16, Stx4a, Stx1a |
| COPII complex | 7.449579942 | 11 | 7 | 0.005695688 | Sar1b, Sar1a, Sec31b, Sec24b, Sec31a, Sec24a, Sec13 |
| Phosphatidylinositol signaling system | 6.130040566 | 81 | 24 | 0.019528072 | Calm1, Synj2, Plcd1, Dgke, Pikfyve, Inpp5k, Itpr2, Inpp5e, Prkcb, Plcb1, Prkca, Plcg1, Calm2, Pi4ka, |

TABLE 1-continued

| KEGG Term | $-\log_{10}$ P value | Genes in Term | Target Genes in Term | Fraction of Targets | Gene Symbol |
|---|---|---|---|---|---|
| | | | | | Dgkh, Impa2, Ocrl, Pip5k1b, Itpr1, Plcb4, Inpp4a, Plcd3, Pik3r3, Synj1 |
| MAPK Signaling pathway | 5.435454827 | 253 | 58 | 0.04719284 | Rps6ka4, Il1r1, Atf4, Map2k5, Prkacb, Pdgfa, Prkx, Taok1, Cacna1a, Rapgef2, Cacna1d, Ikbkb, Nr4a1, Mapk8ip3, Map3k5, Nfkb2, Nlk, Dusp10, Rap1a, Gadd45b, Mapk10, Map2k3, Stmn1, Rap1b, Dusp4, Sos1, Traf6, Mapkapk2, Taok3, Rps6ka5, Hspa8, Map2k1, Cacna1c, Atf2, Elk4, Braf, Ppm1b, Pla2g4b, Prkcb, Mapk11, Mapkapk5, Prkca, Hspb1, Elk1, Ngf, Map3k3, Cacna2d1, Tnfrsf1a, Raf1, Cacna1b, Crkl, Sos2, Mknk1, Rps6ka3, Dusp3, Mapk9, Nf1, Nfatc3 |
| Protein export | 4.23117336 | 25 | 9 | 0.007323027 | Sec11c, Spcs2, Hspa5, Srp9, Immp2l, Sec61b, Spcs1, Srp14, Sec11a |
| Type II diabetes mellitus | 3.580764239 | 50 | 14 | 0.011391375 | Cacna1c, Mapk10, Cacna1b, Slc2a2, Mtor, Insr, Cacna1a, Ikbkb, Cacna1d, Irs1, Mapk9, Pik3r3, Socs4, Prkce |
| Differentially expressed in PdxCre; Bmal1$^{flx/flx}$ islets | | | | | |
| MAPK Signaling pathway | 4.105230153 | 253 | 26 | 0.052631579 | Dusp6, Cacna1c, Elk4, Cd14, Braf, Atf4, Myc, Prkcb, Taok1, Cacna1a, Gadd45g, Chuk, Hspb1, Rasa2, Cacna2d3, Tgfbr1, Map3k2, Cacna2d1, Cacna1h, Cacna2d2, Cacna1b, Akt3, Rras2, Pdgfra, Nf1, Jund |
| Type II diabetes mellitus | 3.580764239 | 50 | 7 | 0.01417004 | Cacna1a, Cacna1c, Hkdc1, Socs2, Cacna1b, Pklr, Socs4 |
| Phosphatidylinositol signaling system | 3.205302246 | 81 | 10 | 0.020242915 | Dgkh, Dgkb, Pikfyve, Prkcb, Plcb4, Itpr1, Plcb3, Itpk1, Pik3c2a, Synj1 |

TABLE 1-continued

| KEGG Term | $-\log_{10}$ P value | Genes in Term | Target Genes in Term | Fraction of Targets | Gene Symbol |
|---|---|---|---|---|---|
| Insulin secretion | 2.164694745 | 86 | 9 | 0.018218623 | Cacna1c, Atf4, Prkcb, Plcb4, Plcb3, Pclo, Kcnn4, Atp1b3, Rims2 |
| Circadian rhythm | 2.009822141 | 30 | 4 | 0.008097166 | Prkab2, Clock, Per2, Per3 |
| COPII complex | 1.817835746 | 11 | 2 | 0.004048583 | Sec23a, Sec24a |
| Protein export | 0.691657973 | 25 | 2 | 0.004048583 | Sec11c, Srp9 |
| SNARE interactions in vesicular transport | 4.31E−12 | 33 | 0 | 0 | 0 |
| BMAL1 Targets nonCycling | | | | | |
| Rap1 signaling pathway | 12.44593154 | 214 | 34 | 0.065637066 | Pdgfc, Sipa1l1, Adcy2, Plce1, Magi2, Pard6b, Bcar1, Rapgef1, Igf1r, Efna5, P2ry1, Akt3, Adcy8, Kit, Gnai1, Fgfr2, Kitl, Src, Pard6a, Vegfc, Pard6g, Itgb1, Hgf, Sipa1l2, Fgf14, Kdr, Ins1, Prkd1, Tek, Magi3, Gnao1, Rac1, Mapk1, Nras |
| MAPK Signaling pathway | 8.881669516 | 253 | 34 | 0.065637066 | Cd14, Gadd45g, Ecsit, Map3k7, Mapk8, Rps6ka2, Cacng4, Dusp1, Cacna2d3, Rps6ka1, Map3k14, Jun, Akt3, Ppm1a, Rasgrf2, Tgfb2, Flnb, Fgfr2, Nfatc1, Ppp3ca, Dusp6, Casp3, Myc, Mef2c, Fgf14, Nfkb1, Rac1, Tgfbr1, Mapk1, Pla2g4a, Nras, Dusp5, Grb2, Cacnb3 |
| Insulin secretion | 7.184122363 | 86 | 15 | 0.028957529 | Gcg, Atp1b1, Rab3a, Cckar, Camk2d, Kcnma1, Kcnn2, Creb3l2, Ins1, Abcc8, Adcy2, Adcy8, Pdx1, Atp1a1, Atp1a3 |
| Phosphatidylinositol signaling system | 2.936660459 | 81 | 10 | 0.019305019 | Cds1, Dgkb, Dgkg, Inpp4b, Pi4kb, Pi4k2a, Plce1, Itpk1, Pten, Inpp5j |
| Circadian rhythm | 2.927736192 | 30 | 5 | 0.00965251 | Cry2, Cul1, Bhlhe40, Bhlhe41, Per1 |
| Type II diabetes mellitus | 2.031842078 | 50 | 6 | 0.011583012 | Mapk1, Mapk8, Hk3, Ins1, Abcc8, Pdx1 |
| Protein export | 1.386777127 | 25 | 3 | 0.005791506 | Sec63, Spcs3, Sec62 |
| SNARE interactions in vesicular transport | 0.387042009 | 33 | 2 | 0.003861004 | Vamp3, Stx18 |
| COPII complex | 1.38097E−11 | 11 | 0 | 0 | 0 |

TABLE 1-continued

| KEGG Term | −log₁₀ P value | Genes in Term | Target Genes in Term | Fraction of Targets | Gene Symbol |
|---|---|---|---|---|---|
| CLOCK targets nonCycling | | | | | |
| Rap1 signaling pathway | 12.87814504 | 214 | 23 | 0.085185185 | Pard6a, Vegfc, Pard6g, Itgb1, Cdc42, Hgf, Sipa1l2, Dock4, Prkd1, Adcy2, Magi2, Mapk1, Bcar1, Pard6b, Rapgef1, Efna5, Akt2, Gnai3, Ngfr, F2rl3, Vegfb, Kit, Gnai1 |
| MAPK Signaling pathway | 7.105451517 | 253 | 20 | 0.074074074 | Dusp7, Dusp6, Cdc42, Tab2, Max, Map3k4, Map3k7, Mapk8, Dusp1, Mecom, Gng12, Mapk1, Rps6ka1, Jun, Map4k2, Dusp5, Akt2, Mknk2, Tgfb2, Ppp3ca |
| Circadian rhythm | 5.503601854 | 30 | 5 | 0.018518519 | Cry2, Fbxl3, Bhlhe40, Bhlhe41, Per1 |
| Insulin secretion | 2.396637964 | 86 | 6 | 0.022222222 | Abcc8, Adcy2, Kcnj11, Camk2d, Kcnma1, Atp1b3 |
| Type II diabetes mellitus | 2.241662226 | 50 | 4 | 0.014814815 | Mapk1, Mapk8, Abcc8, Kcnj11 |
| Phosphatidylinositol signaling system | 0.567315545 | 81 | 3 | 0.011111111 | Dgkg, Inpp4b, Pten |
| SNARE interactions in vesicular transport | 0.34973543 | 33 | 1 | 0.003703704 | Gosr2 |
| COPII complex | 1.40878E-11 | 11 | 0 | 0 | 0 |
| Protein export | 1.1483E-11 | 25 | 0 | 0 | 0 |
| BMAL1 targets Cycling | | | | | |
| Circadian rhythm | 10.2035023 | 30 | 6 | 0.037037037 | Nr1d1, Prkag2, Prkaa2, Rbx1, Arntl, Clock |
| Insulin secretion | 4.527557 | 86 | 6 | 0.037037037 | Pclo, Chrm3, Slc2a2, Camk2g, Rims2, Gnaq |
| Rap1 signaling pathway | 3.138964233 | 214 | 9 | 0.055555556 | Rapgef6, Ngf, Magi1, Skap1, Insr, Pard3, Cnr1, Adora2b, Gnaq |
| Type II diabetes mellitus | 2.361287911 | 50 | 3 | 0.018518519 | Irs1, Slc2a2, Insr |
| MAPK Signaling pathway | 2.306955066 | 253 | 9 | 0.055555556 | Ngf, Il1r1, Dusp4, Ppm1b, Mknk1, Taok1, Rps6ka3, Rps6ka5, Nfkb2 |
| Protein export | 2.285014334 | 25 | 2 | 0.012345679 | Sec61b, Immp2l |
| SNARE interactions in vesicular transport | 1.829545138 | 33 | 2 | 0.012345679 | Stx17, Stx16 |
| COPII complex | 1.537746457 | 11 | 1 | 0.00617284 | Sec31a |
| Phosphatidylinositol signaling system | 1.355737038 | 81 | 3 | 0.018518519 | Pikfyve, Pip5k1b, Itpr2 |
| CLOCK targets Cycling | | | | | |
| Circadian rhythm | 11.92035309 | 30 | 6 | 0.037037037 | Nr1d1, Rorc, Arntl, Per2, Cry1, Per3 |

TABLE 1-continued

| KEGG Term | $-\log_{10}$ P value | Genes in Term | Target Genes in Term | Fraction of Targets | Gene Symbol |
|---|---|---|---|---|---|
| MAPK Signaling pathway | 4.899304791 | 253 | 10 | 0.055555556 | Cacna1c, Cacna2d1, Stmn1, Rps6ka4, Dusp4, Mknk1, Cacna1a, Prkca, Hspb1, Nfatc3 |
| COPII complex | 4.353710244 | 11 | 2 | 0.00617284 | Sec31a, Sec24a |
| Insulin secretion | 1.828132526 | 86 | 3 | 0.037037037 | Cacna1c, Prkca, Chrm3 |
| Type II diabetes mellitus | 1.649314642 | 50 | 2 | 0.018518519 | Cacna1a, Cacna1c |
| Rap1 signaling pathway | 1.339863213 | 214 | 5 | 0.055555556 | Prkca, Cnr1, Vegfa, Calm2, Pfn2 |
| Phosphatidylinositol signaling system | 0.977936239 | 81 | 2 | 0.018518519 | Prkca, Calm2 |
| SNARE interactions in vesicular transport | 0.878529011 | 33 | 1 | 0.012345679 | Stx16 |
| Protein export | 1.66591E−11 | 25 | 0 | 0.012345679 | 0 |

TABLE 2

| | Differentially Expressed in Cycling | Bmal1 KO at ZT2 | BMAL1 Target |
|---|---|---|---|
| Signature β-Cell Genes | | | |
| Glut2 | Yes | No | Yes |
| Gck | No | No | No |
| Kcnj11 | No | No | No |
| Abcc8 | No | No | Yes |
| Pcsk1 | No | No | No |
| Glp1r | No | No | No |
| Ins1 | No | No | Yes |
| Ins2 | No | No | No |
| Key Transcription Factors | | | |
| Pdx1 | NO | No | Yes |
| Nkx2.2 | No | No | No |
| Pax6 | No | No | No |
| NeuroD1 | No | No | No |
| MafA | No | No | No |
| Ngn3 | No | No | No |
| Pax4 | No | No | No |
| "Disallowed" Genes | | | |
| Ldha | Yes | No | No |
| Slc61a1 | No | No | No |
| Pdgfra | No | 2.3 fold increase | No |
| Cxcl12 | No | No | Yes |
| Maf | No | 0.3 fold increase | Yes |
| Lmo4 | No | 1.8 fold increase | No |
| Hk1 | No | No | No |

Example 2

BmaL1 Deficient Beta Cell Line

Materials and Methods
Cell Culture

Beta TC-6 cells were obtained from ATCC (CRL-11506) on Jan. 24, 2014. Cells were cultured in Dulbecco's modified Eagle's Medium supplemented (Corning Cat #10-013-CV) with 15% fetal bovine serum (Cat 35-011-CV), 1% penicillin-streptomycin (Corning, Cat 30-002-CI), and 1% L-glutamine (Life Technologies, Cat #25030081) at 37 degree with 5% CO2. Culture medium was exchanged every 2 or 3 days.

Generation of CRISPR-CAS9 Plasmids Targeting Mouse Bmal1

CRISPR-CAS9 gene editing enables precision gene editing by targeting the CAS9 endonuclease to specific genomic locations using homologous RNA guides. We targeted exon 8 in the mouse Bmal1 gene encoding the DNA binding bHLH domain to mimic the effect of Cre-LoxP models of Bmal1 deletion in vivo which delete this essential domain in mice (PMID 18779586) and we have demonstrated that excision of this exon in beta cells causes hypoinsulinemia and diabetes (PMID 20562852, PMID 26542580). Exon 8 of the mouse Bmal1 gene was targeted by designing RNA guides (sgRNAs) using the Zhang lab CRISPR design tool and the likelihood of targeting off-target templates was minimized by aligning these sequences to the mouse genome. The CAS9 nuclease requires recognition of a PAM consensus sequence (NGG) to cleave DNA so "CACC" nucleotide sequence was added to the 5' end of the sgRNA and "AAAC" was added to the 5' end of the reverse complement of the sgRNA oligos for cloning into the pSpCas9(BB)-2A-Puro vector (Addgene plasmid #48139, deposited by Feng Zhang) using the BbsI restriction enzyme.

sgRNA oligo sequences targeting Bmal1 exon 8 are as follows:

5' forward targeting sequence:
(SEQ ID NO: 13)
CACCGCTGGACATTGCATTGCATGT

5' reverse complement:
(SEQ ID NO: 14)
AAACACATGCAATGCAATGTCCAGC

-continued

```
3' forward targeting sequence:
                                       (SEQ ID NO: 15)
CACCGTAGATAAACTCACCGTGCTA 3' reverse complement:
                                       (SEQ ID NO: 16)
Rev AAACTAGCACGGTGAGTTTATCTAC
```

The two sgRNA oligos were annealed to form double stranded DNA and cloned into the pSpCas9(BB)-2A-Puro plasmid encoding the CRISPR-CAS9 nuclease using the BbsI restriction enzyme.

Figure 14:
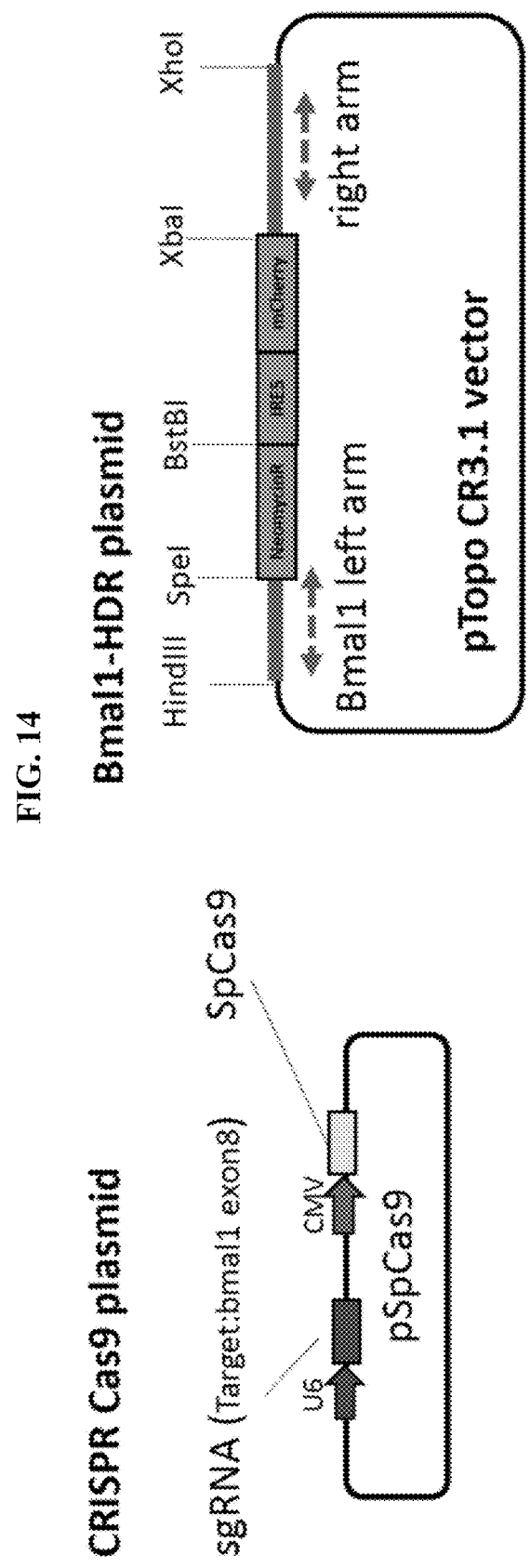
FIG. 14 shows a model of CRISPR-CAS9 plasmids and Bmal1-HDR plasmid targeting mouse Bmal1.

To enable stable selection of Beta TC-6 clones with constitutively disrupted expression of Bmal1 a homology directed repair template (Bmal1-HDR plasmid) encoding a fluorescent marker (mCherry) and selectable marker (neomycin resistance) that was inserted into the region in exon 8 cleaved by the CAS9 endonuclease was utilized (FIG. 14). To do so, a double stranded DNA oligo encoding both an mCherry reporter and neomycin resistance cassette flanked by 1 kb of the complimentary sequence homologous to Bmal1 exon 8 surrounding the PAM sequence recognized by the sgRNAs was used. To generate this plasmid mCherry (pMSCV-IRES-mCherry, Addgene plasmid #52114, deposited by Dario Vignali) and a neomycin resistance cassette (pcDNA3.1, Invitrogen) were cloned into the PCR2.1-TOPO vector (pCR2.1-TOPO, Invitrogen). First the Neomycin resistance cassette was cloned into the Topo cloning site of pCR2.1-TOPO and then the IRES-mcherry sequence was cloned into BstB1 site located between neomycin resistance cDNA and its terminator. Finally, 1 kb sequences homologous to 5' and 3' sequences surrounding the CAS9 targeted region in Bmal1 exon 8 were isolated from mouse genomic DNA and cloned into the PCR2.1-TOPO vector using Hind3/Spe1 sites for the 5' homologous sequence and Xho1/Xba1 sites for 3' homologous sequence, respectively. The whole HDR template sequence including unique homology arms is included.

Figure 15:
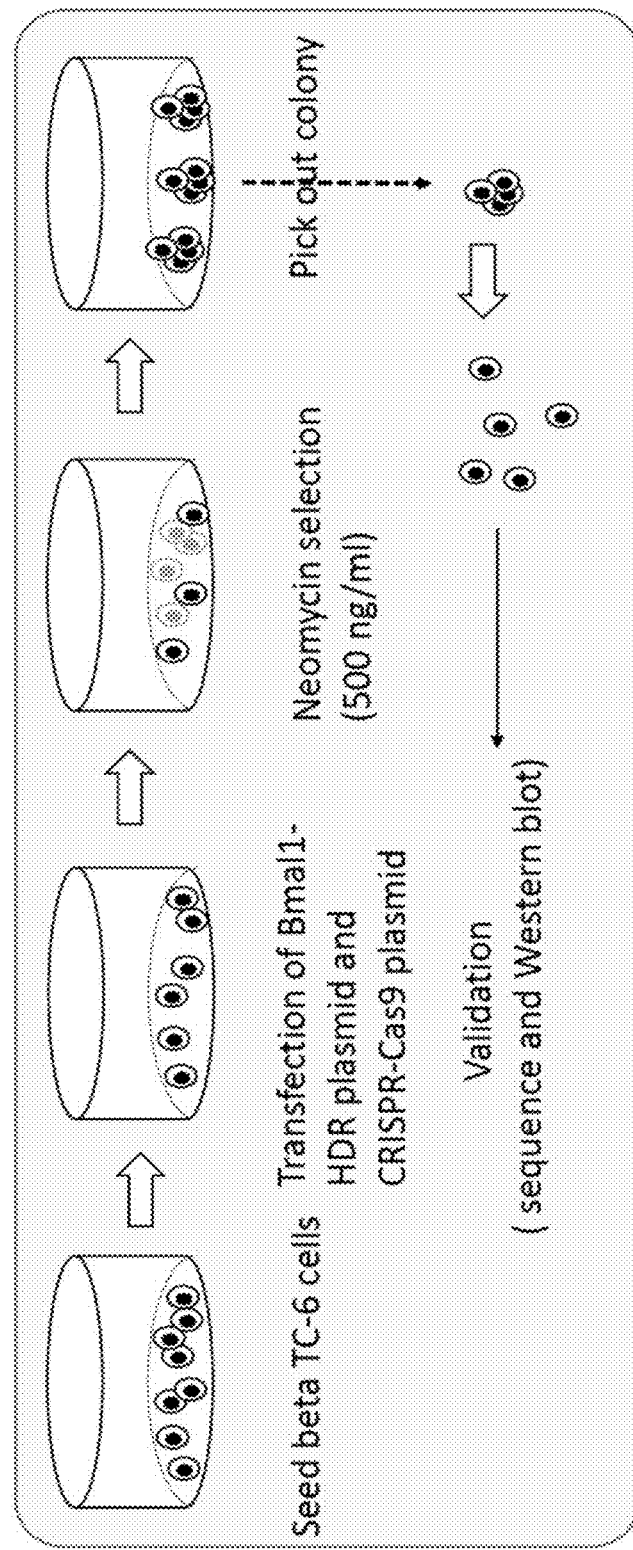
FIG. 15 shows establishment of Bmal1$^{-/-}$ Beta TC-6 Cells

Transfection of CRISPR-CAS9 Plasmids and Stable Selection of Bmal1$^{-/-}$ Cells Beta TC-6 cells (passages 25-30) were plated into 6 well plates (Corning, 353046) and cultured overnight. The pSpCas9 vector containing sgRNAs (400 ug) and the Bmal1-HDR vector (600 ug) were transfected into Beta TC-6 cells using Lipofectamine 2000 (Thermo Fisher Scientific, Cat #11668027) according to the manufacturer's instructions (FIG. 15). After 48 hours transfection, the cells were treated with 500 ng/ml of G418 Sulfate (Corning, 30-234-CR) to select for neomycin resistant clones for 14 days. After G418 selection, more than 10 single colonies were handpicked and cultured individually in 96 well plates (Coring 3603). RNA and protein were extracted from these colonies and Bmal1 expression was assessed by Q-PCR and Western blot.

Generation of Bmal1$^{-/-}$ Beta TC-6 Cells Stably Expressing Insulin Nanoluc

Figure 16:
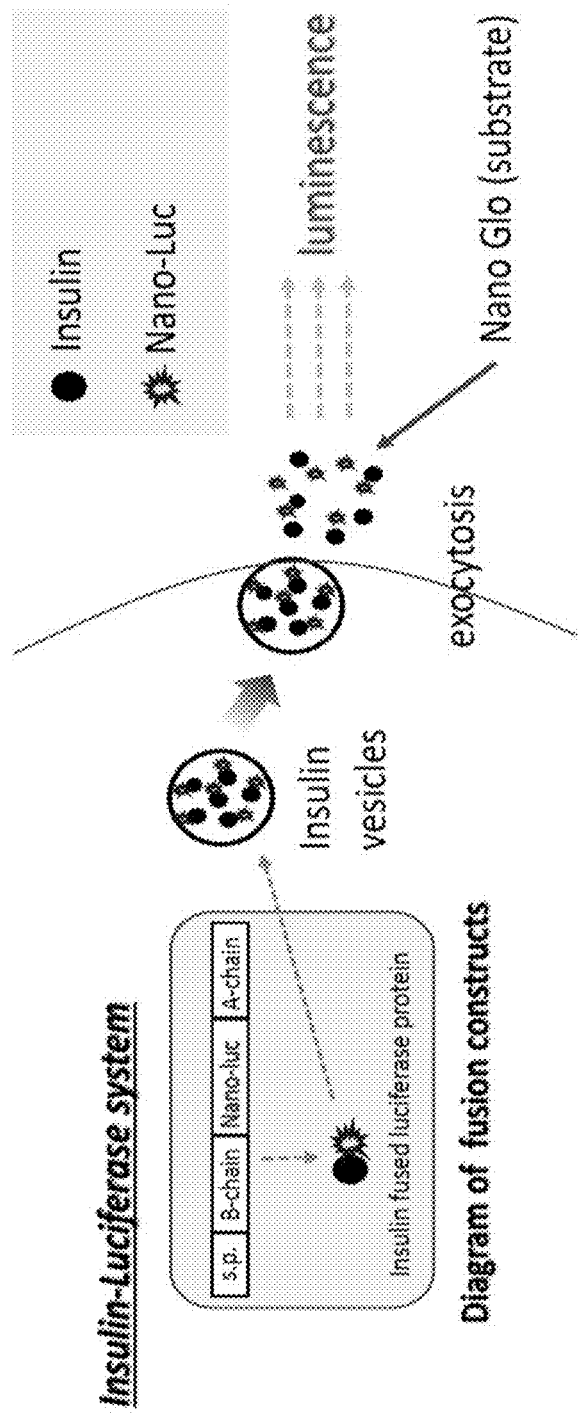
FIG. 16 shows a schematic of an exemplary insulin-NanoLuc System.

The Insulin Nanoluc plasmid (Addgene plasmid #62057, deposited by David Altshuler) was used to provide a low cost, scalable, and rapid method to detect insulin secretion (FIG. 16). The gene encoding Nano luciferase (Nanoluc) is cloned into the C-peptide portion of mouse proinsulin such that cleavage within insulin vesicles by pH-sensitive prohormone convertase results in the cosecretion of Nanoluc with endogenous insulin in a stimulus-dependent manner.

The pLX304 lentivirus packaging plasmid containing the Proinsulin-NanoLuc construct was transfected into HEK293T (ATCC CRL-11268) cells with pCMV-VSVG (envelope vector) and 8.91 (packaging vector) which were obtained from Jeff Milbrandt at Washington University in St. Louis. Supernatant containing lentivirus particles was harvested 48 hours after transfection. Beta TC-6 cells were infected with Insulin-NanoLuc lentivirus and stably expressing cells were selected by treating with puromycin (2 µg/ml, 2 days).

Validation of Insulin Nanoluc Method

Figure 17:
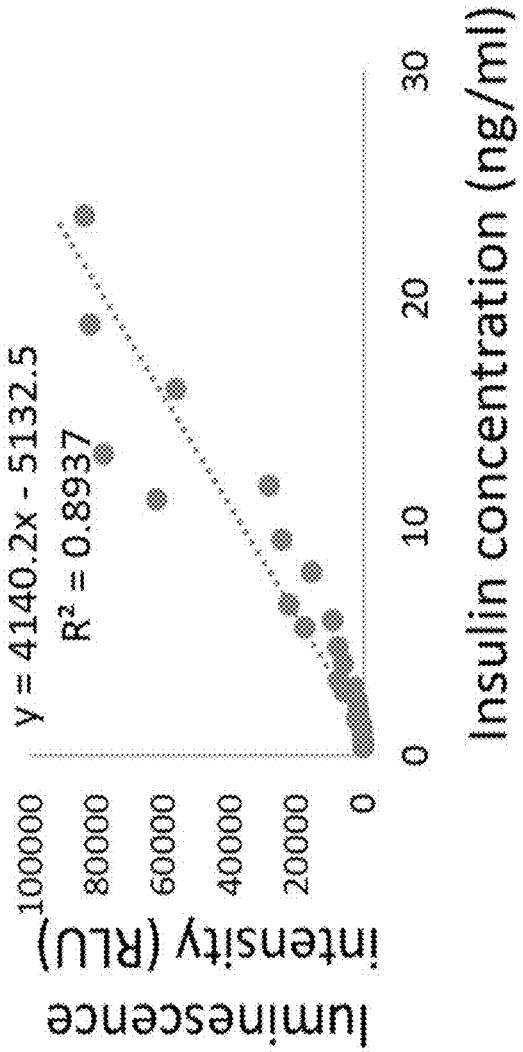
FIG. 17 shows a comparison between luminescence intensity and insulin concentration measured by ELISA.
Figure 19:
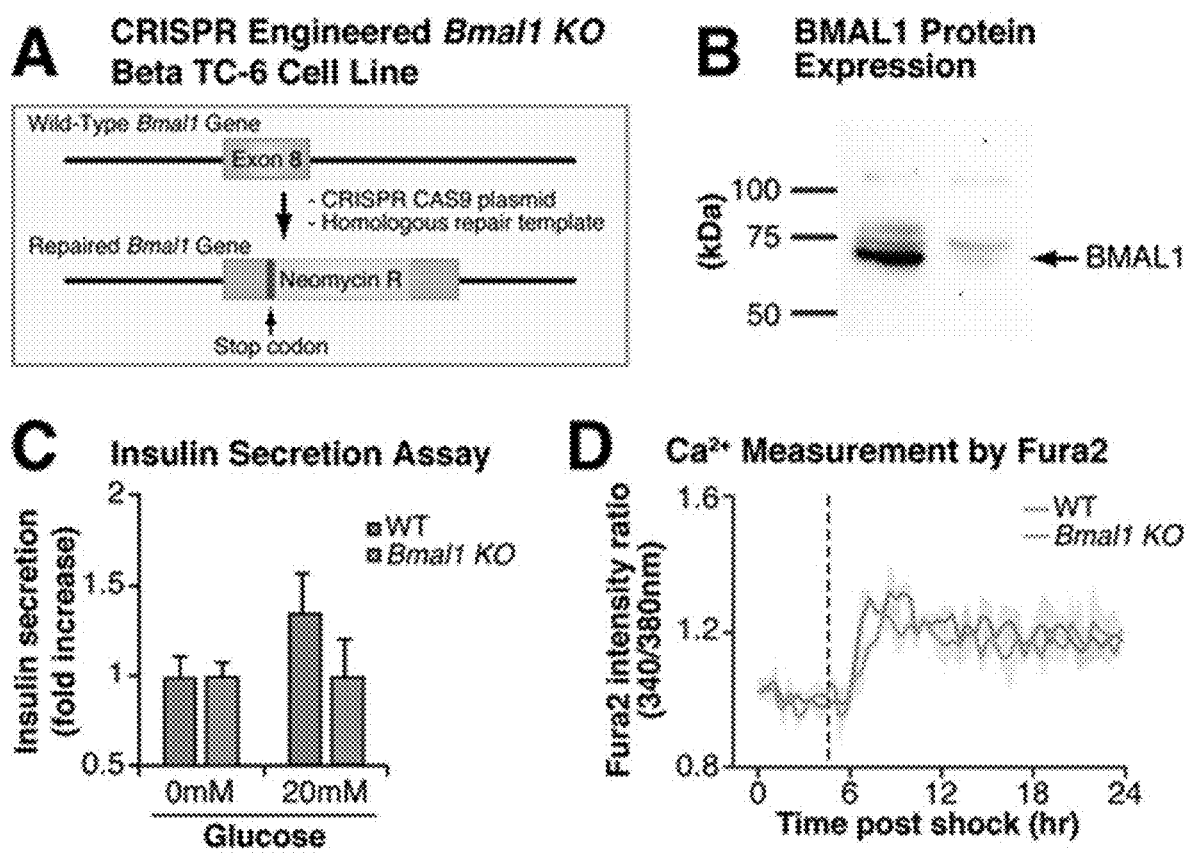
FIG. 19, Panels A-D show generation and characterization of clock mutant Beta TC-6 cell line.
Figure 20:
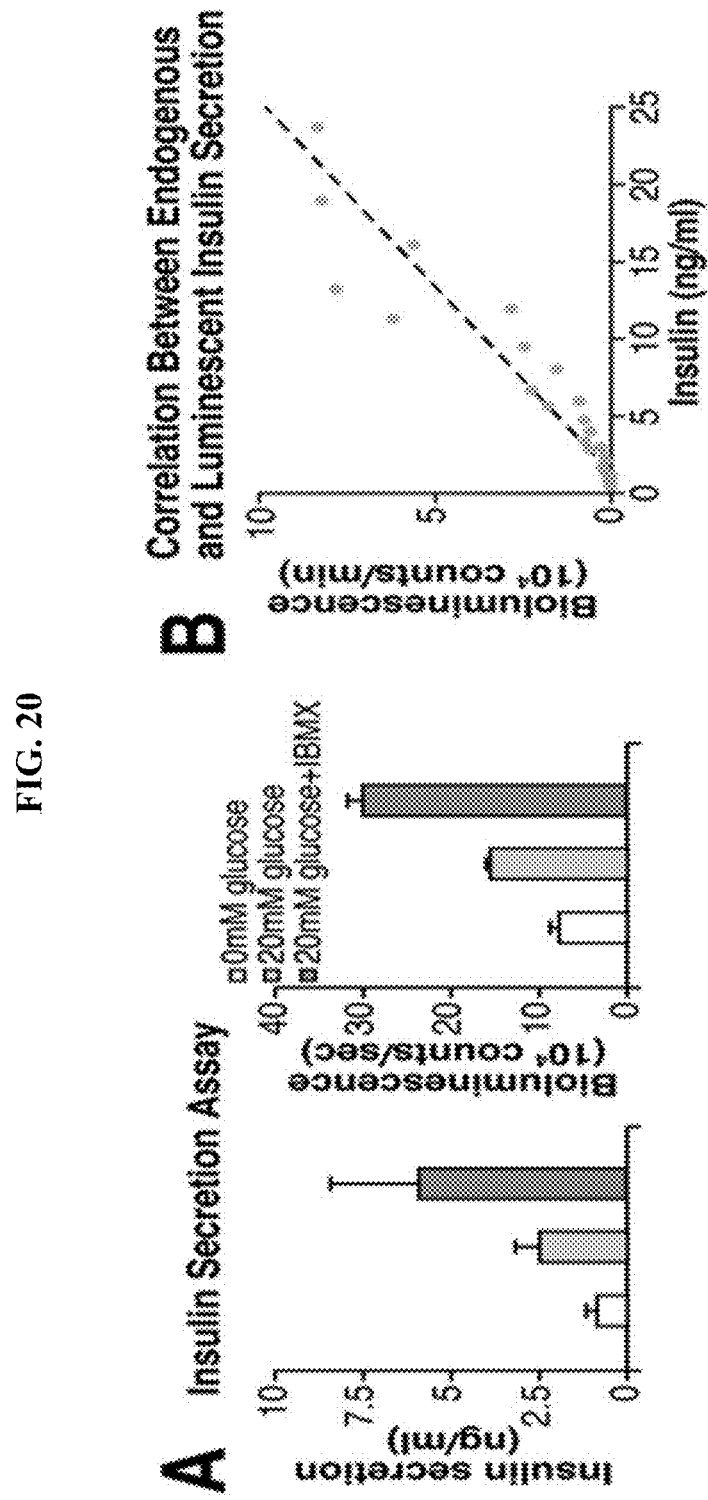
FIG. 20, Panels A and B show bioluminescent detection of INS::Luciferase in Beta TC-6 Cells
Figure 21:
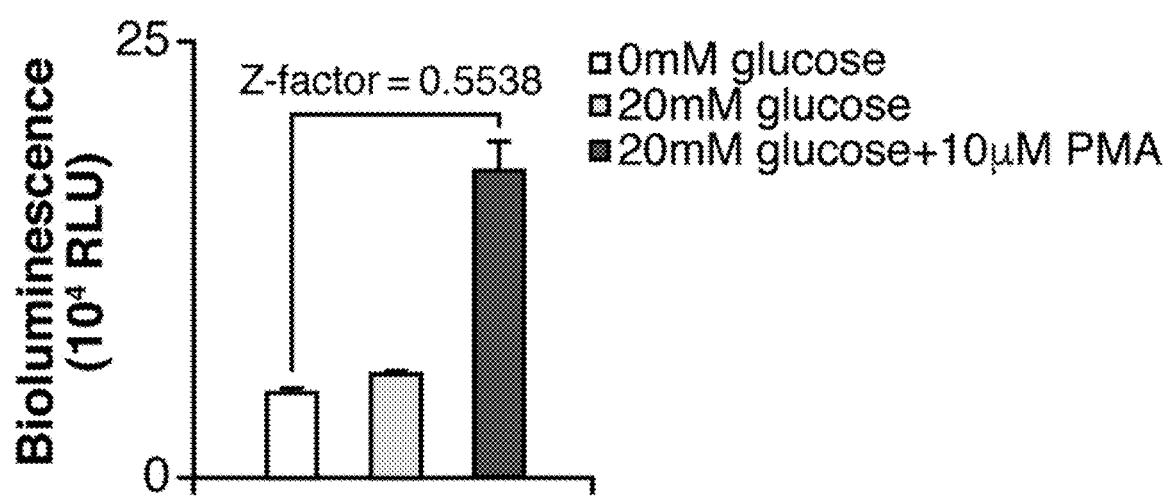
FIG. 21 shows a test of clock mutant INS::Luc Beta TC-6 cells in 384-well format

To ensure that the Insulin Nanoluc secretion is correlated to the secretion of endogenous insulin, luciferase intensity and insulin concentration measured by ELISA in supernatants of Insulin Nanoluc-expressing Beta TC-6 cells was compared following stimulation with 20 mM glucose. It was confirmed that luciferase intensity is highly correlated with endogenous insulin secretion (FIG. 17).

High Throughput Screen for Drugs to Rescue Insulin Secretion in Bmal1$^{-/-}$ Beta Cells A high throughput screen was used to identify small molecule drugs capable of restoring glucose-stimulated insulin secretion in clock-deficient beta cells. Bmal1$^{-/-}$ beta cells and primary islets display reduced glucose-stimulated insulin secretion (GSIS) and that agonists of $G_q$-coupled muscarinic receptor and diacyl glycerol (DAG) signaling rescue secretion to that of wild type cells. Compounds to augment GSIS in Bmal1$^{-/-}$ cells were identified by adding compounds in combination with 20 mM glucose and using the DAG mimetic Phorbol 12-myristate 13-acetate (PMA), which rescues GSIS in these cells, as a positive control. The spectrum collection small molecule compound library (MicroSource Discovery Systems, Inc) consisting of 2700 known drugs and drug-like molecules was screened for compounds that augment insulin secretion in Bmal1$^{-/-}$ Beta TC-6 cells. Insulin Nanoluc expressing Bmal1$^{-/-}$ Beta TC-6 cells (30,000 cells/well) were plated in 384 well plates and cultured for 4 days at 37° C. with 5% CO2. Prior to the assay, cells were washed once with KRB buffer containing 0 mM glucose and starved in glucose-free KRB buffer for 1 hour. After aspirating, KRB buffer containing 20 mM glucose in addition to small molecules (10 uM) were added, and the cells were incubated for 1 hour. As a negative control, 16 wells received only 20 mM glucose, which fails to elicit insulin secretion in Bmal1$^{-/-}$ cells, and an additional 16 wells received KRB buffer containing 20 mM glucose and 10 µM PMA, which is known to induce insulin secretion in Bmal1$^{-/-}$ mouse islets and Beta TC-6 cells. After 1 hour, the supernatant was collected and centrifuged at 500G for 30 min. The supernatant was transferred into a fresh 384-well assay plate containing Nano-Glo Luciferase Assay Substrate (Promega) and luciferase intensity was measured by EnSpire Plate Reader (PerkinElmer) Intensity was measured within 30 minutes.

Figure 22:
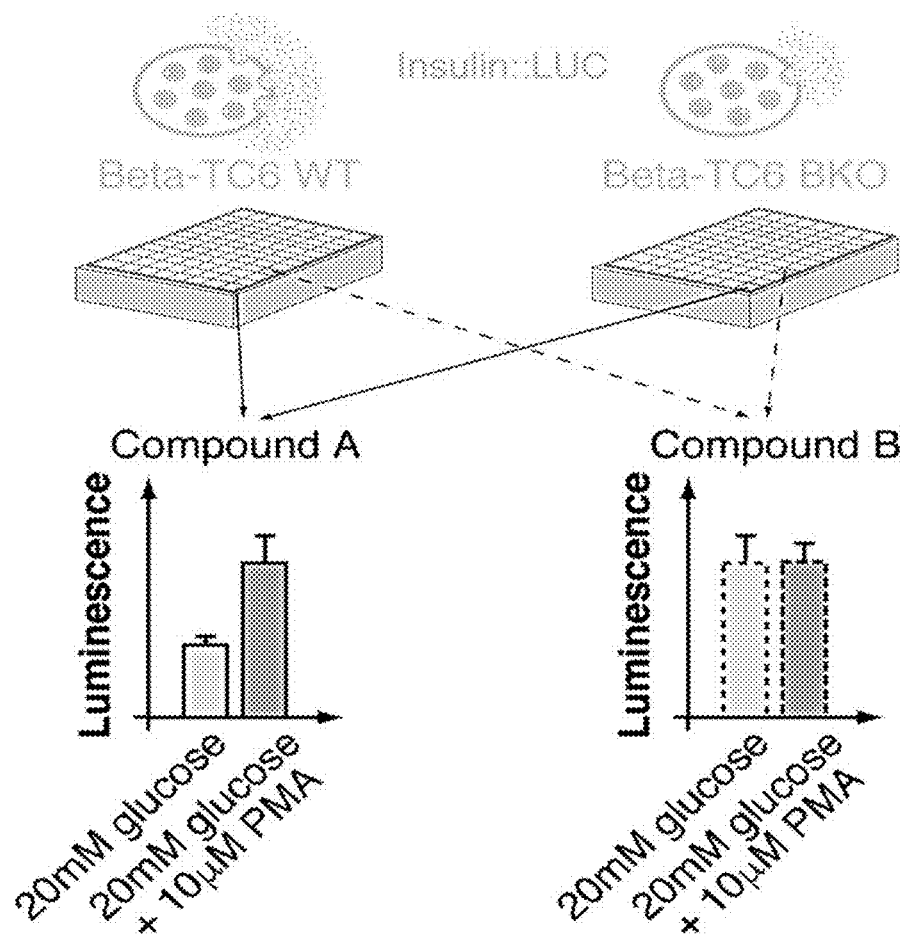
FIG. 22 shows high throughput screening for insulin agonists using clock mutant INS::Luc cell line.
Figure 23A:
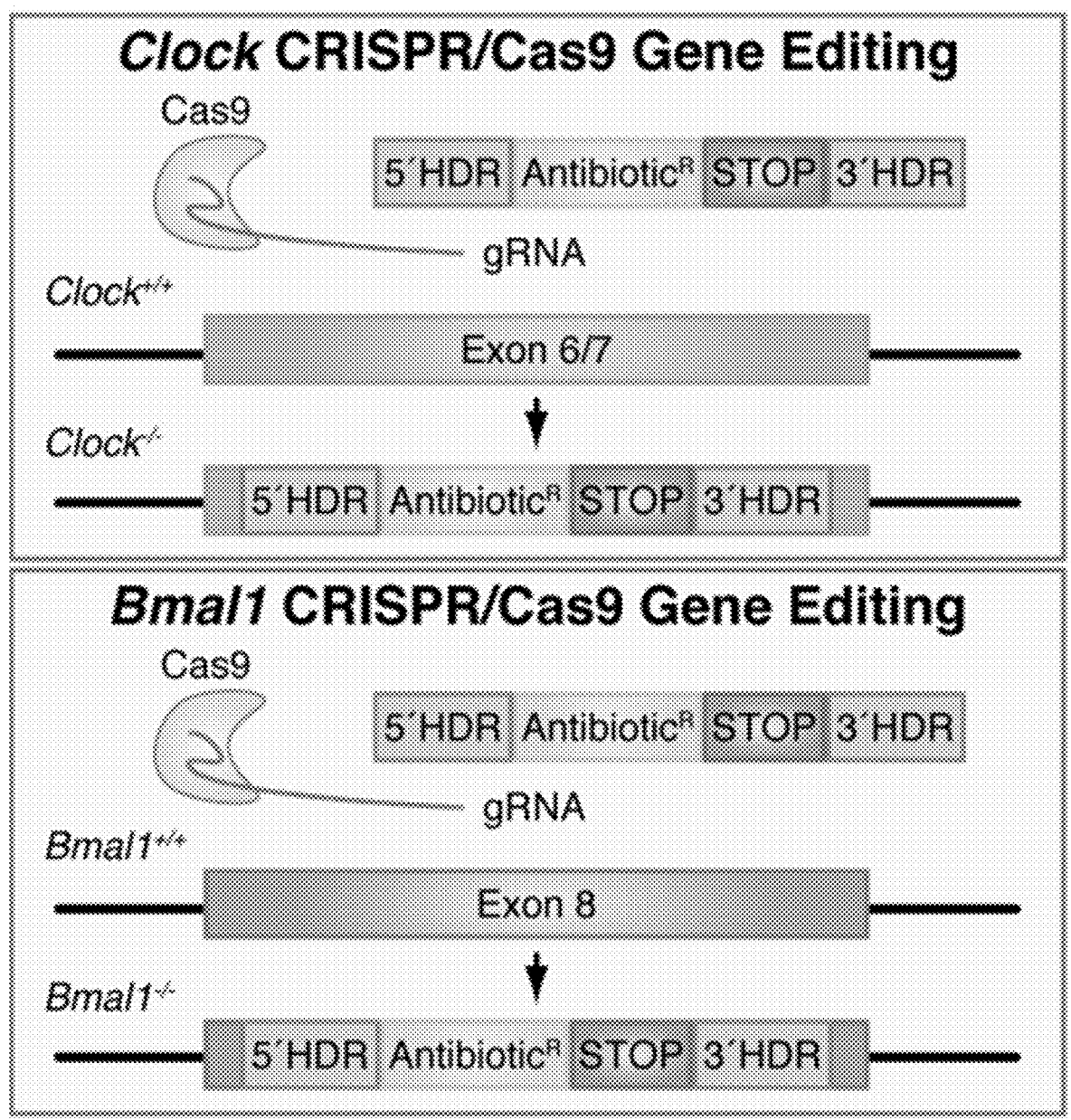
FIGS. 23A-23E show CRISPR/Cas9-generated β-cell lines with impaired clock function and insulin secretion.
Figure 23B:
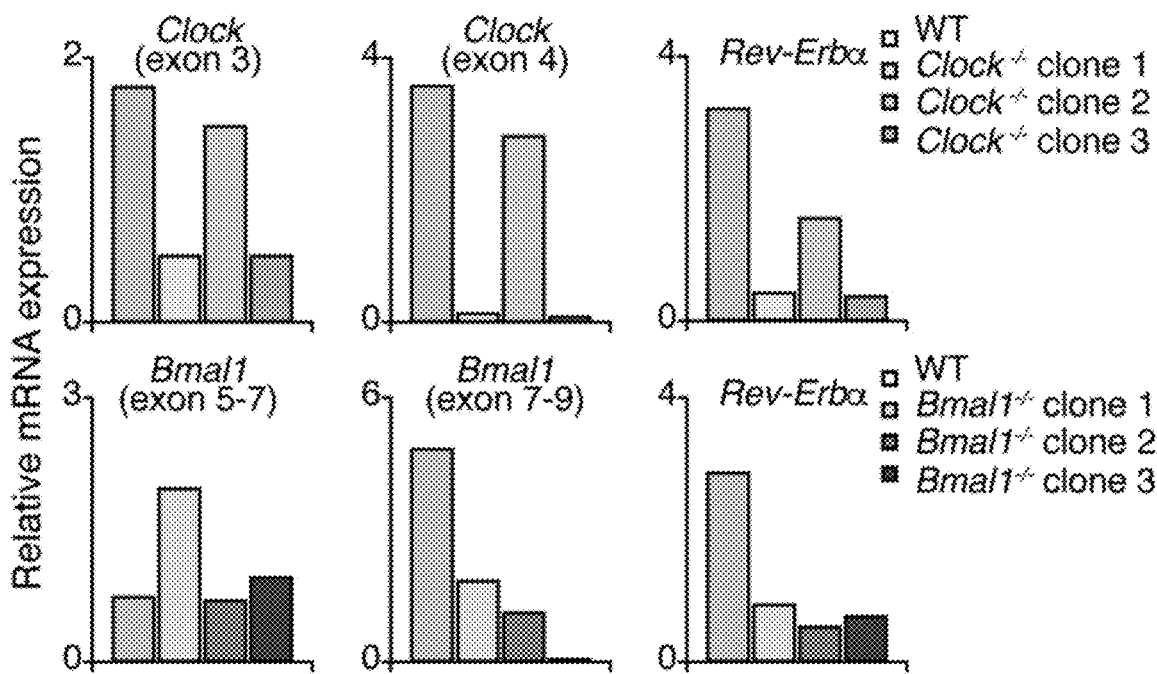
Figure 23C:
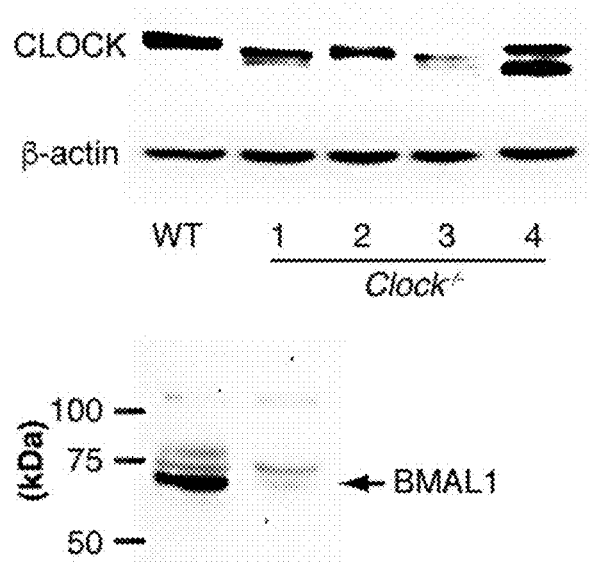
Figure 23D:
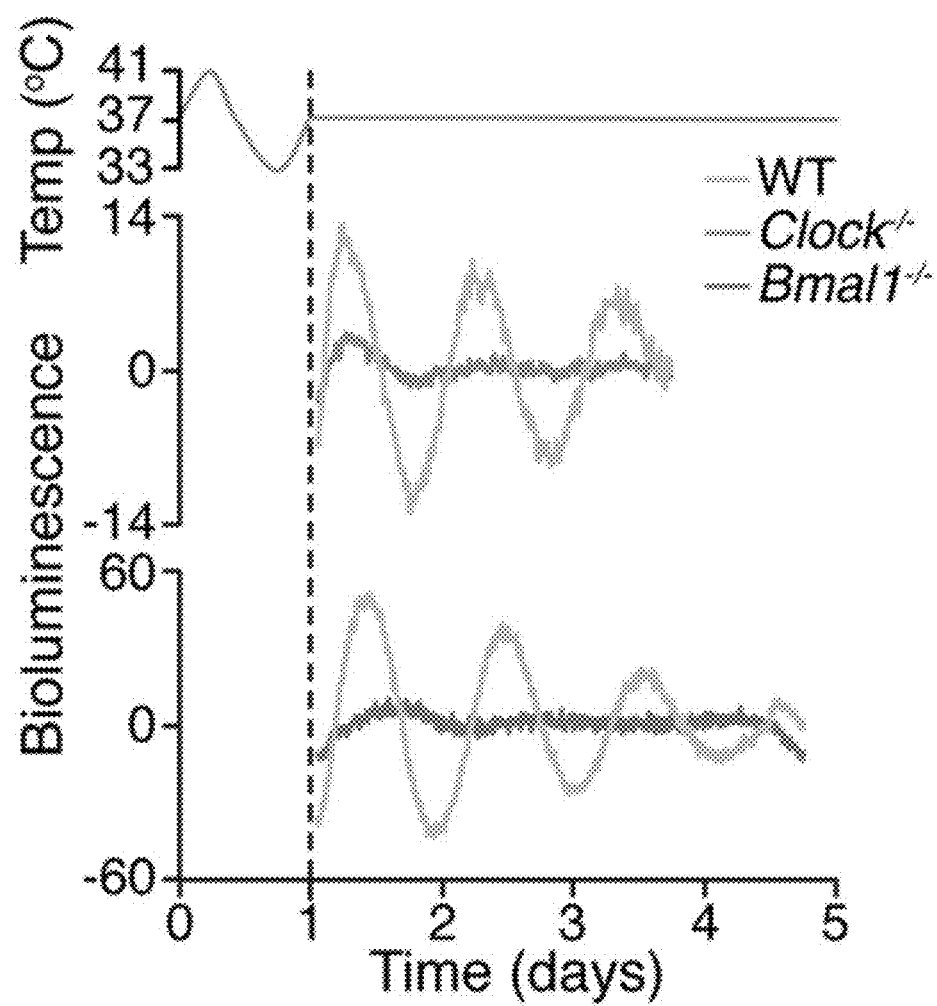
Figure 23E:
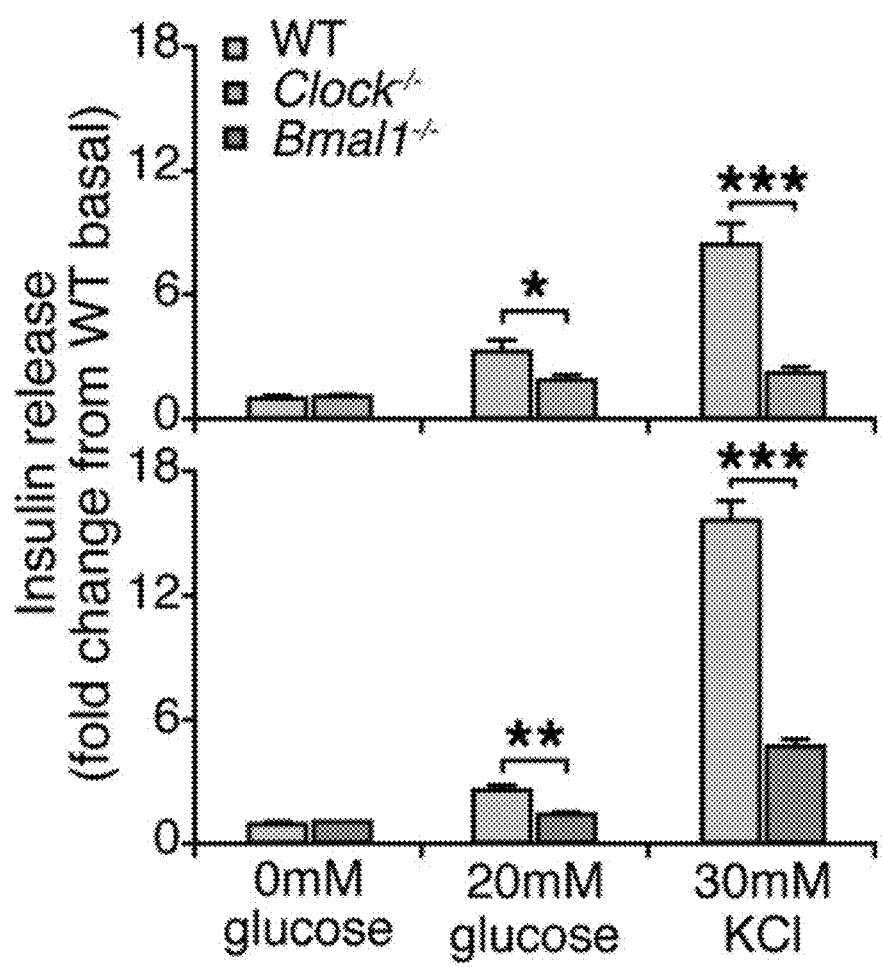

FIG. 22 shows generation and characterization of the Bmal1$^{-/-}$ β-cell line. Immortal mouse beta cells lacking a functional circadian clock were generated using CRISPR-CAS9 gene editing. These cells recapitulated the phenotypes observed in clock primary clock mutant mouse islet β-cells, including impaired glucose-stimulated insulin secretion, yet normal glucose-stimulated calcium flux.

FIG. 23 shows bioluminescent detection of INS::Luciferase in beta TC-6 cells. Stable cell lines expressing a fusion protein consisting of INSULIN and a low molecular weight variant of luciferase, Nanoluc (Promega, N1321) were generated by lentivirus gene delivery. INS::Luc secretion in response to glucose and the cAMP agonist IBMX is highly correlated with the secretion of endogenous insulin.

Figure 24:
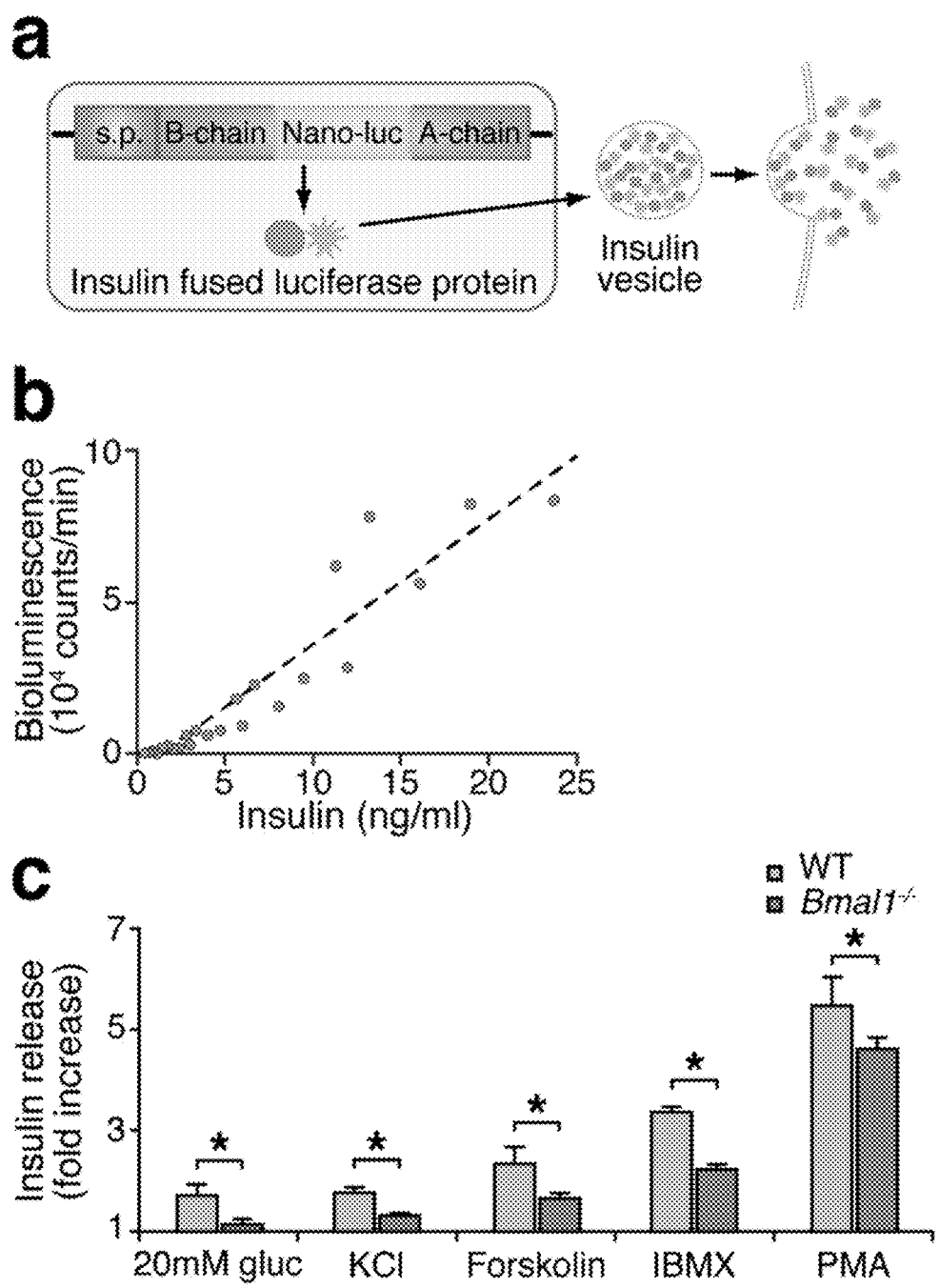
FIG. 24 shows validation of insulin-luciferase-expressing Bmal1 KO reporter cell lines for use in high throughput screening. (Panel a) Schematic for insulin-nano-luc construct incorporated into the CRISPR/Cas9-generated Bmal1 KO cell line. (Panel b) Correlation between endogenous (x-axis) and luminescent (y-axis) insulin. (Panel c) Insulin secretion as measured by luminescent intensity following exposure to indicated secretatogue.

FIG. 24 shows a test of clock mutant INS::Luc beta TC-6 cells in a 384-well format. INS::Luc secretion can be robustly detected using cells plated in 384-well format. Comparison of signal in cells treated with 0 mM glucose, 20 mM glucose, and 20 mM glucose+10 µM PMA as positive control produced a Z-factor greater than 0.5, indicating that a screen for agonists that increase secretion to the level of PMA is feasible.

Figure 25:
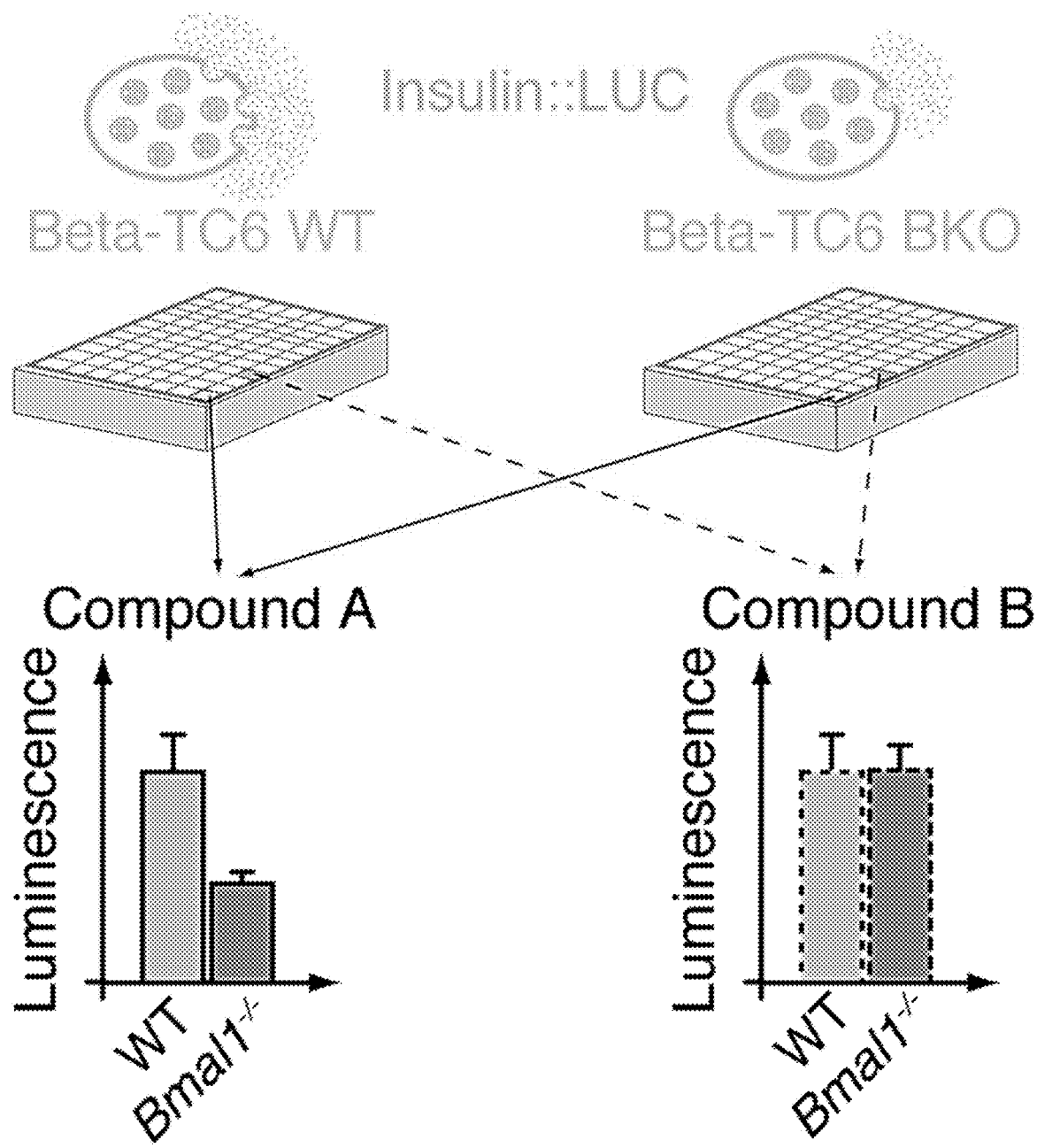
FIG. 25 shows a schematic for high-throughput chemogenetic screening of the Spectrum library to identify enhancers of insulin secretion during circadian disruption. An example is shown whereby Compound A has no effect on restoration of insulin secretion in the Bmal1 KO cells, while Compound B restores insulin secretion in the Bmal1 KO cells to that of WT levels, thus identifying a "hit" compound that rescues insulin secretion in the setting of circadian disruption.

FIG. 25 shows high throughput screening for novel insulin agonists using clock mutant INS::Luc cell line. Clock mutant INS::Luc cells are used to screen for compounds that restore insulin secretion in the absence of a functional molecular clock in 384-well format. As a positive control a subset of cells on each 384-well plate are treated with 20 mM glucose+10 µM PMA and the effectiveness of individual compounds is assessed based on their ability to increase glucose-stimulated secretion.

Determination of Hit Compounds

Z scores for luciferase intensities produced by screened compounds were calculated from the following formula:

$$z=(X-\mu)/\sigma$$

where z is the z-score, X is intensity of compounds, $\mu$ is the intensity of negative control (20 mM glucose), and $\sigma$ is the standard deviation of negative control. Hit compounds were defined as those that elicited a response of more than 3 standard deviations from the mean (Z score>3).

Hit Compounds

Screening the spectrum library of 2700 compounds in Bmal1$^{-/-}$ Insulin Luc expressing cells yielded 34 hit compounds that displayed a Z score>3 (as described above). A literature search revealed that the known and predicted targets for 23 of the hits are cell surface receptor and ion channel proteins. Among these were 4 compounds targeting ion channels including the glutamate-gated cation channel NMDAR, ligand and temperature gated TRPV1 cation channel, and a glutamate gated chloride channel. The targets of the remaining 19 compounds are membrane bound receptors belong to the 7 transmembrane g-coupled protein receptor superfamily including muscarinic and nicotinic acetylcholine receptors, dopamine receptors, serotonin receptors, a g coupled bile acid receptor and the beta 2 adrenergic receptor. Eleven of these GPCRs are known to couple to the $G_q$ protein, which is consistent with these compounds operating through DAG signaling which we have previously found to rescue GSIS in Bmal1$^{-/-}$ beta cells. Two compounds target $G_s$ coupled receptors that signal via adenyl cyclase and cAMP and the remaining 6 compounds targeted receptors coupled to the $G_{i/o}$ protein that inhibits adenyl cyclase and activates phospholipase C/DAG signaling.

Example 3

Circadian Clock Interaction with HIF1α Mediates Cellular Oxygenic Energy Production and Glycolysis Materials and Methods Animals All animal care and use procedures were in accordance with guidelines of the Institutional Animal Care and Use Committee. Bmal$^{fx/fx}$ mice (25512522) were crossed with ACTA-rtTA-TRE-Cre transgenic mice (kindly provided by Dr. Grant Barish) 19263419) to generate ACTA-rtTA-TRE-Cre;Bmal1$^{fx/fx}$ mice, as well as Bmal1$^{fx/fx}$ and ACTA-rtTA-TRE-Cre littermate controls. Vhl$^{fx/fx}$ mice (Jackson Laboratories) (11171994) were crossed with CAG-Cre-ER transgenic mice (Jackson Laboratories) (11944939) to generate CAG-Cre-ER; Vhl$^{fx/fx}$ mice, as well as Vhl$^{fx/fx}$ and CAG-Cre-ER controls. All experiments were performed using male C57BL/6J mice between 3-5 months of age, and mice were maintained on a 12:12 light dark (LD) cycle in the Northwestern University Center for Comparative Medicine.

CRISPR Mediated Gene Deletion in C2C12 Myoblasts

CRISPR-Cas9 technology was utilized to direct homologous recombination-mediated excision of exon 8 of the Bmal1 gene in C2C12 myoblasts (18779586). The mouse Bmal1 gene was targeted by designing RNA guides (sgRNAs) using the Zhang lab CRISPR design tool and the likelihood of targeting off-target templates was minimized by aligning these sequences to the mouse genome. (pSpCas9 (BB)-2A-Puro). An additional plasmid was generated from pTOPO2.1 (Invitrogen) containing the Neomycin resistance cassette from pCDNA3.1-neo (Invitrogen) flanked by ~1 kb intronic regions of genomic DNA directly to the 5' and 3' of BMAL1 exon 8 (named pBmal1-HR). C2C12 myoblasts were co-transfected with guide RNA and pBmal1-HR plasmids, and stably-integrated clones were selected for neomycin resistance (G418, Mediatech). Clones were assayed for loss of Bmal1 mRNA and protein expression. Data shown are averaged data from two independent Bmal1$^{-/-}$ clones.

Oxygen Consumption Rate (OCR) and Extracellular Medium Acidification Rate (ECAR) Measurements OCR and ECAR were measured in differentiated C2C12 myyotubes as previously described (24051248, 21189469). Cells were plated and differentiated on Seahorse Biosciences 96-well culture plates and transferred to fresh glucose-containing medium (for OCR) and no glucose-containing medium (for ECAR) without sodium bicarbonate 1 hour prior to measurements. Plates were placed in a XF96 Bioanalyzer, and OCR and ECAR were measured before and after sequential addition of 10 µM Oligomycin and 10 µM carbonylcyanide-p-trifluoromethoxyphenylhydrazone (FCCP) (for OCR wells) or 10 mM glucose and 10 µM Oligomycin (for ECAR wells).

Protein Gel Electrophoresis and Immunoblotting

MEF and C2C12 whole cell lysates were prepared in CelLytic™ MT Mammalian Tissue Lysis Reagent (Sigma) supplemented with protease inhibitors. Snap-frozen mouse skeletal muscle tissue was diluted in CelLytic™ MT Mammalian Tissue Lysis Reagent (Sigma) supplemented with protease inhibitors and homogenized using a TissueLyser II apparatus (Qiagen). Protein levels were quantified using DC Protein Assay (Biorad), and protein extracts were subject to SDS-PAGE gel electrophoresis and transferred to nitrocellulose membranes (GE Healthcare). Primary antibodies used were anti-HIF1α (Novus Biologicals) and anti-β-actin (Cell Signaling).

Quantitative Real-Time PCR

Total RNA was extracted from C2C12 and MEF cell pellets and snap-frozen mouse skeletal muscle tissue using Tri-Reagent (Molecular Research Center, Inc). For muscle tissue samples, tissue was homogenized using a TissueLyser II apparatus (Qiagen). cDNA was synthesized using the High Capacity cDNA Reverse Transcription kit (Applied Biosystems). Real-time PCR was performed and analyzed using a CFX384 (Biorad). PCR conditions were: 10 min at 95° C., then 35 cycles of 10 s at 95° C., 15 s at 60° C. Relative expression levels (normalized to 18S rRNA (C2C12 and MEF) or β-actin (skeletal muscle)) were determined using the comparative CT method.

Luciferase Assays

Undifferentiated C2C12 myoblasts were transfected with plasmids expressing either the PER2:LUCIFERASE (15620658, 18454201) or hypoxia response element (HRE)-luciferase reporters (kindly provided by Dr. Navdeep Chandel) (18268343), as well as plasmids expressing genes encoding bHLH-PAS proteins including CLOCK, BMAL1, HIF1α, and ARNT (HIF1β). 48 hours after transfection, cells were assayed for luciferase activity using the Dual Luciferase Assay Kit (Promega).

C2C12 Myotube Synchronization

For RNA expression studies, confluent dishes of C2C12 myoblasts were first differentiated with 2% horse serum two days prior to cell synchronization. Cells were then synchronized by serum shock every 4 hours for 44 hours with 50% horse serum as previously described (22210883). Twenty-four hours after the final shock, cells were collected and analyzed for mRNA expression. For PERIOD2:LUCIFERASE (PER2:LUC) reporter assays, C2C12 myoblast cells were first infected with PER2:LUC-expressing lentivirus (gift of A. Liu, University of Memphis) (18454201) and maintained in DMEM that included 10% FBS and 2.5 µg/ml blastocidin to select for stable Per2-luc integration. Myoblasts were then differentiated for 5 days with 2% horse serum, and then synchronized in 50% horse serum for 2 hours. Myotubes were then treated with either 62.5 uM Dimethyloxalylglycine (DMOG) (Sigma) or DMSO (vehicle) in DMEM plus 0.1 mM luciferin and 0.5% horse serum, and luciferase activity was continuously monitored using a LumiCycle apparatus (Actimetrics).

Chromatin Immunoprecipitation (ChIP)

ChIP experiments were performed as previously described. Briefly, C2C12 myotubes were dual-crosslinked with Disuccinimidyl glutarate DSG for 30 min followed by 1% formaldehyde for 10 min. Myotubes were collected, and nuclei were isolated via needle lysis in IP buffer (ref). Chromatin was sheared by sonication and incubated overnight with 2 µg of either anti-HIF1α antibody (Novus Biologicals) or anti-BMAL1 antibody (generated as described (26542580)) followed by 2 hours with pre-blocked protein A Agarose beads (Millipore). Beads were washed 6 times followed by de-crosslinking using Chelex beads (Sigma) and proteinase K (Invitrogen) digestion. Eluted immunoprecipitated DNA and input DNA were purified by Qiaprep mini-elute reagents and subjected to qPCR analysis using primers specific to known CLOCK/BMAL1 E-box target sites.

Mouse Embryonic Fibroblast (MEF) Isolation

MEFs were isolated as previously described (24051248). Pregnant mice were sacrificed at pcd 14-15, and embryos were dissected away from the uterus and placed in 1×PBS. Heads and internal organs were removed, and heads were subsequently used for genotyping. Blood was washed away from the remaining carcasses with 1×PBS, and tissue was minced in Trypsin-EDTA, followed by incubation with stirring for 30 minutes. Trypsin was neutralized with heat-inactivated FBS, and cells were pelleted by centrifugation at 270×g for 5 minutes. Following centrifugation, cells were resuspended in DMEM containing 15% FBS and plated at $1 \times 10^6$ cells per 100 mm dish. Media was changed 24 hours after plating. Cells were maintained in DMEM containing 15% FBS.

Mouse Treadmill Exercise 3-4 month old male C57B6L/J mice were familiarized with the treadmill (Columbus Instruments) by running for 15 min at 6 m/min on two consecutive days prior to our experiments. On the third day, mice were placed on the treadmill for 3 min at 6 m/min. After 3 min, the treadmill speed was increased by 1 m/min every minute until exhaustion, which was defined as more than 10 falls onto the stimulus grid per minute. Mice were euthanized by $CO_2$ inhalation followed by cervical dislocation, and skeletal muscle tissue was snap-frozen in liquid nitrogen.

Results

Tissue-Specific Circadian Control of HIF-Mediated Anaerobic Glycolysis

To determine whether the cell autonomous circadian clock in skeletal muscle contributes to regulation of fuel utilization and glycolytic flux, oxygen consumption (OCR) and extracellular medium acidification (ECAR) rates, which quantify mitochondrial respiration and glycolysis, respectively, were assessed in $Bmal1^{-/-}$ C2C12 mouse myoblasts generated using CRISPR-CAS9-mediated homologous recombination under relative normoxic conditions. Similar to previous findings in $Bmal1^{-/-}$ liver, impaired OCR was observed in $Bmal1^{-/-}$ myotubes compared to WT myotubes both in basal conditions and in response to the ATP synthase inhibitor oligomycin and the drug FCCP, which measure uncoupled respiration and maximal flux through the electron transport chain (ETC), respectively (24051248). A major difference was observed, however, in comparing anaerobic glycolysis in liver and skeletal muscle metabolism in $Bmal1^{-/-}$ myotubes. Specifically, in contrast to $Bmal1^{-/-}$ liver, which exhibits increased anaerobic glycolysis and lactate production (24051248), $Bmal1^{-/-}$ myotubes exhibited reduced extracellular lactate production, as indicated by decreased ECAR both in basal conditions and in response to glucose and when the ETC is blocked by oligomycin, indicating tissue-specific differences in the circadian regulation of fuel selection between liver and muscle.

Since HIF1α is known to be important for glycolytic metabolism in oxidative tissues such as skeletal muscle during both rest and in response to hypoxia (15328538, 26391197, 24619881), as well as for promoting aerobic glycolysis in von Hippel Lindau angioblastomas, renal cell carcinoma, and other endocrine neoplasms (12209156), it was contemplated that reduced HIF1α within $Bmal1^{-/-}$ skeletal muscle may underlie their impaired ECAR, and that the muscle clock may mediate anaerobic glycolytic metabolism through interactions with the HIF pathway. Furthermore, in contrast to tissues such as liver where basal levels of HIF1α are low, skeletal muscle expresses relatively high levels of HIF1α protein even under normoxic conditions (11689469), indicating potential tissue-specific roles of HIF1α in normoxic and hypoxic conditions. Moreover, loss of HIF1α specifically in skeletal muscle leads to decreased basal and exercise-induced expression of glycolytic genes and correspondingly low lactate production and impaired tolerance to strenuous acute exercise in mice (15328538, 16043777, 18269201, 16043777). Thus, the impact of genetic disruption of both the circadian clock activator versus repressor TFs on the HIF-mediated response to hypoxia was next assessed. In mouse embryonic fibroblasts (MEFs) isolated from mice lacking the clock activator BMAL1, HIF1α accumulation was observed in response to increasing doses of cobalt chloride ($CoCl_2$), an iron antagonist and 'hypoxia-mimetic' which stabilizes HIF1α by inactivating prolyl hydrolyases, rendering them incapable of marking HIF1α for degradation (7539918). Conversely, MEFs lacking the circadian repressors CRY1 and CRY2 displayed increased HIF1α accumulation compared to control cells following CoCl2 exposure, indicating that the core circadian clock feedback loop controls HIF protein levels and the hypoxic response. In addition, we observed a similar reduction in HIF accumulation in $Bmal1^{-/-}$ myotubes exposed to environmental hypoxia (1% 02 for up to 6 hrs), in parallel with reduced expression of known HIF1α target genes in the absence of Bmal1, including its own negative regulator Prolyl hydroxylase 3 (Phd3) and the pro-angiogenesis factor Vascular endothelial growth factor-alpha (Vegfα), as well as several genes important for anaerobic glycolysis, including Lactate dehydrogenase A (Ldha), Pyruvate kinase muscle isoform (Pk-m), and the Monocarboxylate transporter 4 (Mct4) (15823097, 8089148, 15288294, 16452478, 9113979). Finally, a similar decrease in Ldha and Mct4 expression was observed in gastrocnemius muscle of skeletal muscle-specific Bmal1 knockouts (ACTA-rtTA-TRE-Cre;Bmal$^{fx/fx}$) compared to controls (19263419), indicating cell-autonomous in vivo regulation of the glycolytic fuel utilization pathways in skeletal muscle. Together, these data indicate a role for the circadian clock in mediating HIF-dependent control of muscle lactate production and its secretion at both the cell autonomous level in myoblasts and in the intact animal in vivo.

The impaired hypoxia-induced HIF1α accumulation and transcriptional activity in the Bmal1 mutant cells may be due to reduced HIF1α/BMAL1 heterodimerization due to the absence of BMAL1, potentially leading to reduced stability of the nuclear monomeric form of HIF1α, as is the case in cells lacking HIF1β (10085255). In support of a physiologic interaction between HIF1α and BMAL1, in vitro structural and biochemical studies reveal direct dimerization between bHLH-PAS protein components of the HIF and clock pathways, as a high degree of sequence- and structure-level similarity exists between HIF1β (aka ARNT) and the core clock activator BMAL1 (also termed ARNT-like), particularly within the protein-protein PAS domain interaction surfaces (22653727, 24263188). While the N-terminus contains the bHLH domain for DNA binding, the conserved central PASA and PASB domains are responsible for nutrient sensing, recruitment of transcriptional co-regulatory proteins, and determining specificity for heterodimerization with other bHLH-PAS factors (22653727, 17024177, 23240775, 21512126, 24263188, 9632792). To test functional interactions between HIF1α/BMAL1 heterodimers, the transactivation by these TFs of the hypoxia-response element (HRE), a canonical regulatory motif present within the promoter of HIF1α-target genes, was examined in mammalian skeletal muscle cells. Specifically, the ability of HIF1α, in combination with either HIF1β (ARNT) or BMAL1 (ARNT-like), to activate a HRE-luciferase reporter was assessed (18268343). It was found that HIF1α/BMAL1 trans-activated HRE-luciferase to an even greater extent than HIF1α/HIF1β (ARNT), whereas CLOCK/BMAL1 and CLOCK/ARNT did not activate HRE-luciferase, demonstrating the formation of a transcriptionally competent HIF1α/BMAL1 complex in mouse skeletal muscle cells and providing further evidence that the circadian clock regulates the hypoxic response pathway through HIF1α.

Hypoxia and HIF1α Exert Reciprocal Control of Circadian Transcription Cycles

Given the functional interaction observed between HIF1α and BMAL1, and that they both target similar E-box-like motifs, it was contemplated that a bi-directional relationship may exist between the circadian and hypoxic pathways. Several approaches were taken to determine whether the HIF pathway exerts reciprocal effects upon the core clock itself. First, to determine the impact of hypoxia on the period length of the autonomous circadian clock within muscle cells, synchronized C2C12 myotubes that stably expressed the circadian reporter PERIOD2:LUCIFERASE (PER2:LUC) were treated with the HIF1/2α-stabilizing drug dimethyloxalyl glycine (DMOG), which inhibits PDH/VHL-mediated HIF degradation similarly to CoCl2 but without causing toxicity due to long-term culture (11595184, 15620658, 18454201, 1321909, 11292861). Continuous monitoring of luciferase activity revealed significant period lengthening of PER2:LUC oscillations in the presence of DMOG (22 hrs in DMSO-treated controls compared to 23 hrs in DMOG-treated cells, p<0.05), demonstrating that HIF directly impacts a core property of the circadian clock within muscle.

Second, to determine whether HIF1α localizes to regulatory regions within core clock genes in skeletal muscle, directed chromatin immunoprecipitation (ChIP) of HIF1α was performed at endogenous CLOCK/BMAL1 targets containing canonical E-box binding sites (5'-CACGTG-3') (22936566). Significantly enhanced binding of HIF1α to the E-box within the promoter regions of Per1 and Cry1 was found, as well as to canonical HRE targets sites within the Ldha and Vegfa promoters (24360282, 21343542), but not within a non-specific promoter for Slc2a2, the solute carrier family 2 gene encoding the glucose transporter GLUT2, which does not contain a canonical CLOCK/BMAL1 E-box binding site. Direct binding of HIF1α to circadian target genes suggests a role for the hypoxic response in regulating circadian gene transcription and is consistent with the impact of HIF1α on period length. Third, the ability of HIF1α to trans-activate the Period2 gene through co-expression of HIF1α and BMAL1 was assessed and it was found that HIF1α/BMAL1 stimulated the transcription of the PER2:LUC reporter expressed within C2C12 myoblasts to a similar extent as CLOCK/BMAL1. Furthermore, increased expression of core clock genes was found in both myotubes and MEFs in response to hypoxia induced by either exposure to 1% $O_2$ or with the chemical mimetic $CoCl_2$. These findings are consistent with the previous observations that increased period length correlates with increased expression of circadian repressors (10408444, 11395012, 10217146). Importantly, nearly all of the induced genes are direct targets of CLOCK/BMAL1 and contain E-box regulatory sites within their promoters.

Finally, to test the epistatic relationship between HIF and CLOCK/BMAL1 activity in response to hypoxia, clock gene expression was examined in MEF cells generated from mice carrying a tamoxifen-inducible CRE-mediated deletion of the Von Hippel-Lindau (Vhl) gene (Cag-CRE-ER;Vhl$^{fx/fx}$) (11171994), a tumor suppressor and E3 ligase that is deficient in clear-cell carcinomas and haemangioblastomas and responsible for the rapid turnover of HIF1α in normoxic tissues (12209156). Consistent with the effect of hypoxia and HIF stabilization on clock gene expression in wild-type embryonic fibroblasts and C2C12 myotubes, Vhl$^{-/-}$ MEFs displayed increased expression of core clock genes, indicating that hypoxia induces circadian gene expression through induction of the HIF pathway. Together, these data uncover a bi-directional relationship between the circadian and hypoxic pathways, whereby hypoxia and HIF stabilization reciprocally feedback to regulate the core clock itself.

Circadian Clock Generates Time-of-Day-Dependent Hypoxic Response to Exercise

The findings above highlight a reciprocal interaction between circadian and HIF TFs in skeletal muscle. To determine whether the circadian clock and HIF TFs act cooperatively to control gene expression in muscle tissue in vivo in response to a hypoxi challenge, a model of acute strenuous exercise in mice to induce hypoxic stress was employed. Mice lacking HIF1α in skeletal muscle fail to induce the expression of HIF1α-regulated genes important in the production of ATP via glycolysis and lactate and display reduced tolerance to strenuous exercise, indicating a defect in type II fast-twitch muscle fibers and suggesting a role of HIF1α in acute exercise tolerance (15328538). Thus, using strenuous exercise a paradigm, assays were performed to test 1) whether HIF induction is gated by activity of the circadian clock (e.g., by time of day), and 2) whether clock gene expression is altered by hypoxic stress in skeletal muscle tissue in vivo. WT mice were exercised by treadmill running to exhaustion at either ZT0 or ZT12, the start of the light or dark period, respectively (total run time was approximately 20-35 minutes depending on the mouse). Gastrocnemius muscle (i.e. primarily type II fiber-containing) was then rapidly excised and assayed for both HIF1α- and clock-target gene expression. Of note, induction of both HIF1α targets, including Pk-m, Ldha, and Vegfα, and clock targets, including Bmal1, Per1, Cry2, and Nampt, was observed when mice were exercised at ZT0, but not at ZT12, indicating that circadian timing controls the induction of the HIF- and clock-dependent transcriptional response to exercise in vivo. These data demonstrate a clear time-of-day dependent effects of hypoxia on both core clock and HIF target genes, reinforcing the reciprocal nature of the circadian and hypoxic response pathways in response to both time of day and alterations in the oxygenic environment.

Circadian clocks are unique in that they are capable of not only anticipating daily changes in the solar cycle, leading to daily oscillations in the expression of oxidative and reductive metabolic enzymes, but also retaining plasticity, enabling adaptation to flux in the nutrient and oxygen environment. The capacity of circadian clocks to exhibit flexibility can be understood at the molecular level since clock TFs contain PAS domains that are canonical environmental response modules important in sensing flux in xenobiotic, metabolite, and oxygen, and transducing such changes into adaptive transcriptional programs (24263188, 20148691, 10357859). Described herein is a previously uncharacterized relationship between molecular clocks and the activity of HIF1α in mouse skeletal muscle, revealing how peripheral clocks collaborate with the central oxygen-responsive TF HIF1α to promote rhythmic tissue-specific metabolic function. While in silico and in vitro biochemical analyses have led to the proposal that HIF TFs may form complexes with circadian clock proteins due to the high degree of structural similarity between the HIF and clock TFs, a hypothesis supported by studies in the vertebrate zebrafish model (23421720, 25730270, 9576906), it has remained unclear whether functional interactions between the bHLH-PAS proteins might occur in mammalian tissues important in the balance between oxidative and reductive metabolism. To address the potential integration of circadian and oxygen-sensing mechanisms under physiologic conditions in mammalian cells, skeletal muscle tissue was utilized for several reasons including: (i) muscle tissue displays abundant HIF1α protein levels and transcriptional activity relative to other tissue types, showing that circadian clock/HIF interactions may participate in basal ('normoxic') metabolic function (11689469), (ii) HIF1α is a determinant of exercise tolerance in type IIX glycolytic muscle fibers (15328538, 18269201, 24794533), and (iii) genetic disruption of the ARNT-like circadian activator, BMAL1, leads to impaired muscle fiber distribution, glycolytic gene expression, and glucose tolerance (26000164, 26486627, 24567902). Thus, it was hypothesized that the skeletal muscle circadian clock may play a role in both anticipating oxidative-reductive fuel cycles each day, but also gating the capacity of oxidative skeletal muscle to augment glycolytic energy production through regulation of HIF signaling.

The data provide several lines of evidence that crosstalk between circadian and oxygen-sensing pathways is established through physical and functional interaction between HIF1α and the circadian protein BMAL1. First, dose-dependent transactivation of both the HRE- and PER2-luciferase reporters was observed when BMAL1 and HIF1α were co-expressed, indicating that these factors form heterologous and transcriptionally competent complex. Second, HIF1α enrichment was observed at canonical CLOCK/BMAL1 E-box sites, including those present in the Per1 and Cry1 promoters, demonstrating direct HIF1α occupancy localized to regulatory sites within the promoter regions of core clockgenes.

The ability of cells to respond to acute changes in oxygen levels is an important feature of aerobic organisms and requires a functional HIF1α network. As oxygen levels decrease, the generation of ATP shifts from mitochondrial oxidative phosphorylation to oxygen-independent glycolysis in the cytoplasm, a HIF1α-dependent process. Interestingly, the findings show an important role for the clock in this process, as we reveal that HIF1α-BMAL1 interactions may regulate glucose metabolism in a tissue-specific manner. Remarkably, whereas Bmal1$^{-/-}$ liver showed increased anaerobic glycolytic gene expression and lactate production under normoxic conditions (24051248), Bmal1 myotubes display an opposite phenotype of reduced extracellular lactate production and reduced expression of known HIF1α targets, consistent with the reduced levels and transcriptional activity of HIF1α in muscle. This observation has important implications for defining the tissue-specific physiologic role of the HIF1α-clock TF interaction in mediating basal muscle metabolism even in the resting normoxic state, in contrast to liver, where HIF1α-clock TF interactions likely only induce glycolysis during hypoxic stress.

The studies presented here reveal endogenous HIF-clock TF interactions in skeletal muscle under both normoxic and hypoxic conditions that may have broader implications for understanding the interplay between circadian and oxygen sensing pathways in pathological hypoxic states including anemia and cardiac and ischemic cerebral injury. Furthermore, while BMAL1-mediated HIF activation may be beneficial to promote adaptation to hypoxic stress such as exercise and ischemic stress, it is possible that circadian regulation of HIF may contribute to pathologies in which HIF drives aberrant aerobic glycolysis including tumor growth and progression. In this instance, it is tempting to speculate that pharmacological modulation of clock activity may aid in HIF down-regulation particularly in cancers involving mutations in Vhl and mitochondrial oxidative enzymes (e.g. succinate dehydrogenase (Sdh)) (16892081).

In summary, the clock system functions not only to anticipate changes in the external light cycle, but peripheral clocks also act as a rheostat to regulate oxygen sensing in oxidative tissues under both basal and hypoxic conditions.

Example 4

Figure 26A:
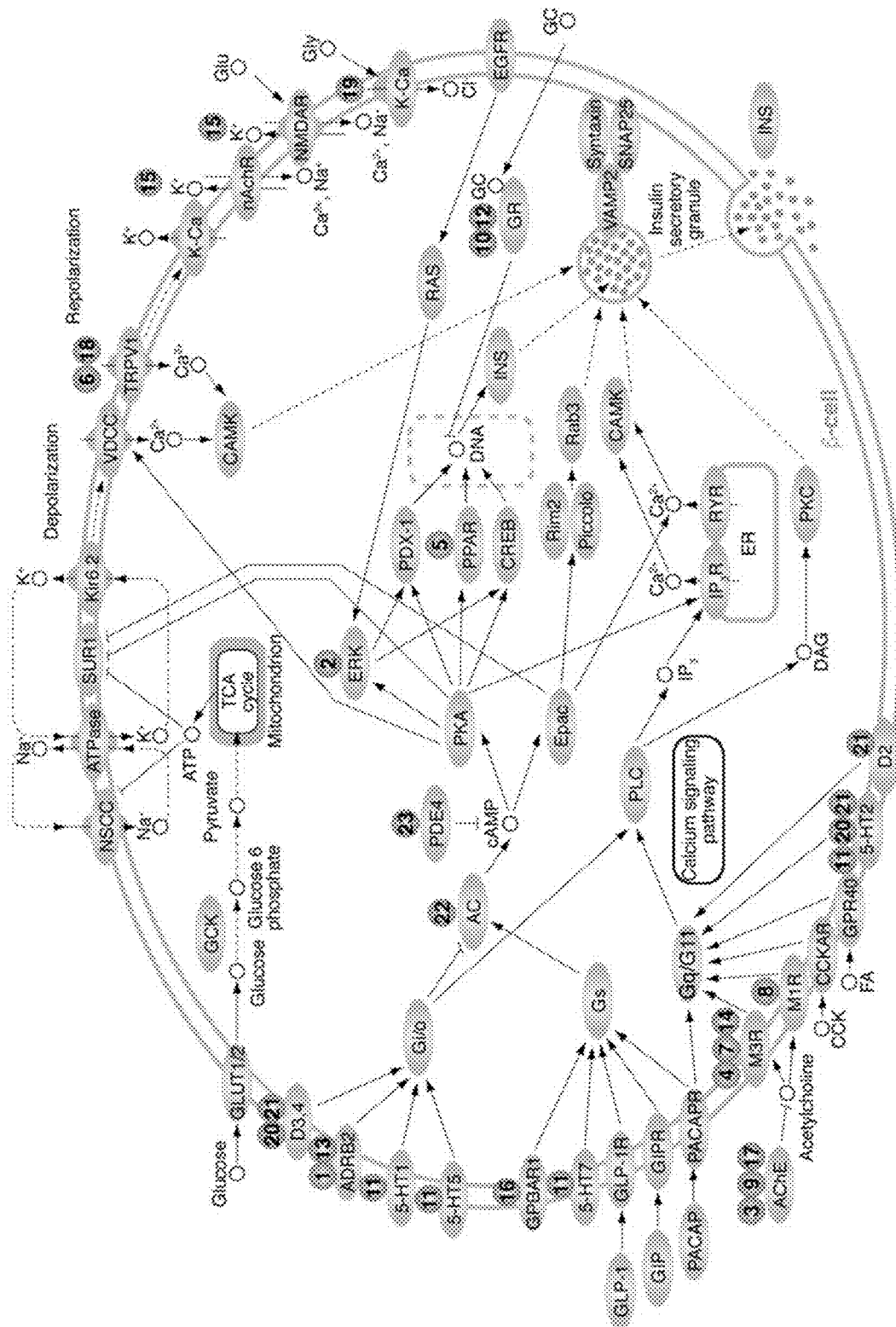
Figure 27:
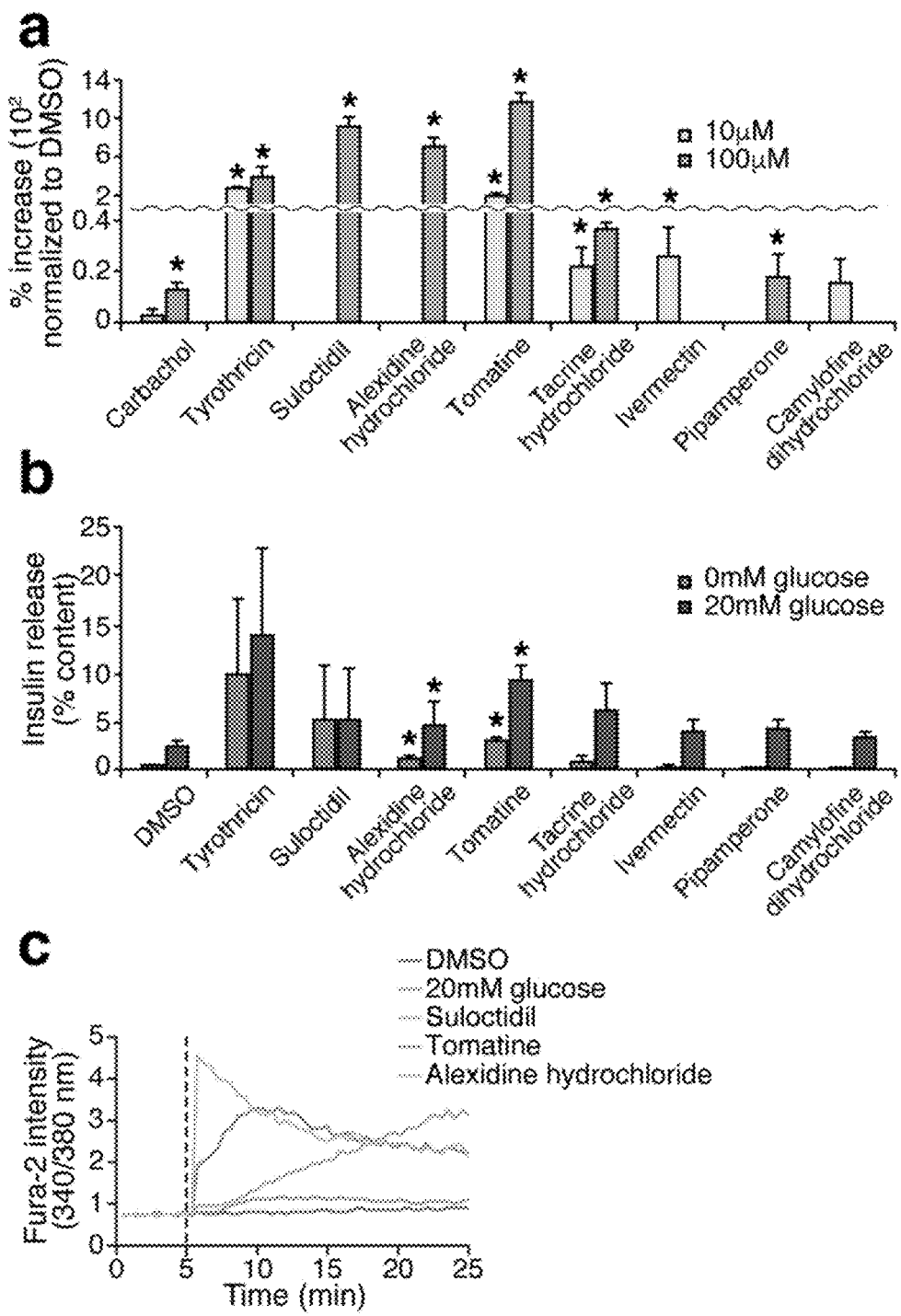
FIG. 27 shows validation of primary screening compounds' effect on insulin secretion and calcium flux. Insulin secretion in presence of (Panel a) increasing doses of indicated drugs in Bmal1-deficient β-cell lines and (Panel b) 0 vs 20 mM glucose+ indicated drugs in primary mouse islets. (Panel c) Influx of calcium indicated by Fura-2 intensity following exposure to indicated drugs. *p<0.05.
Figure 28:
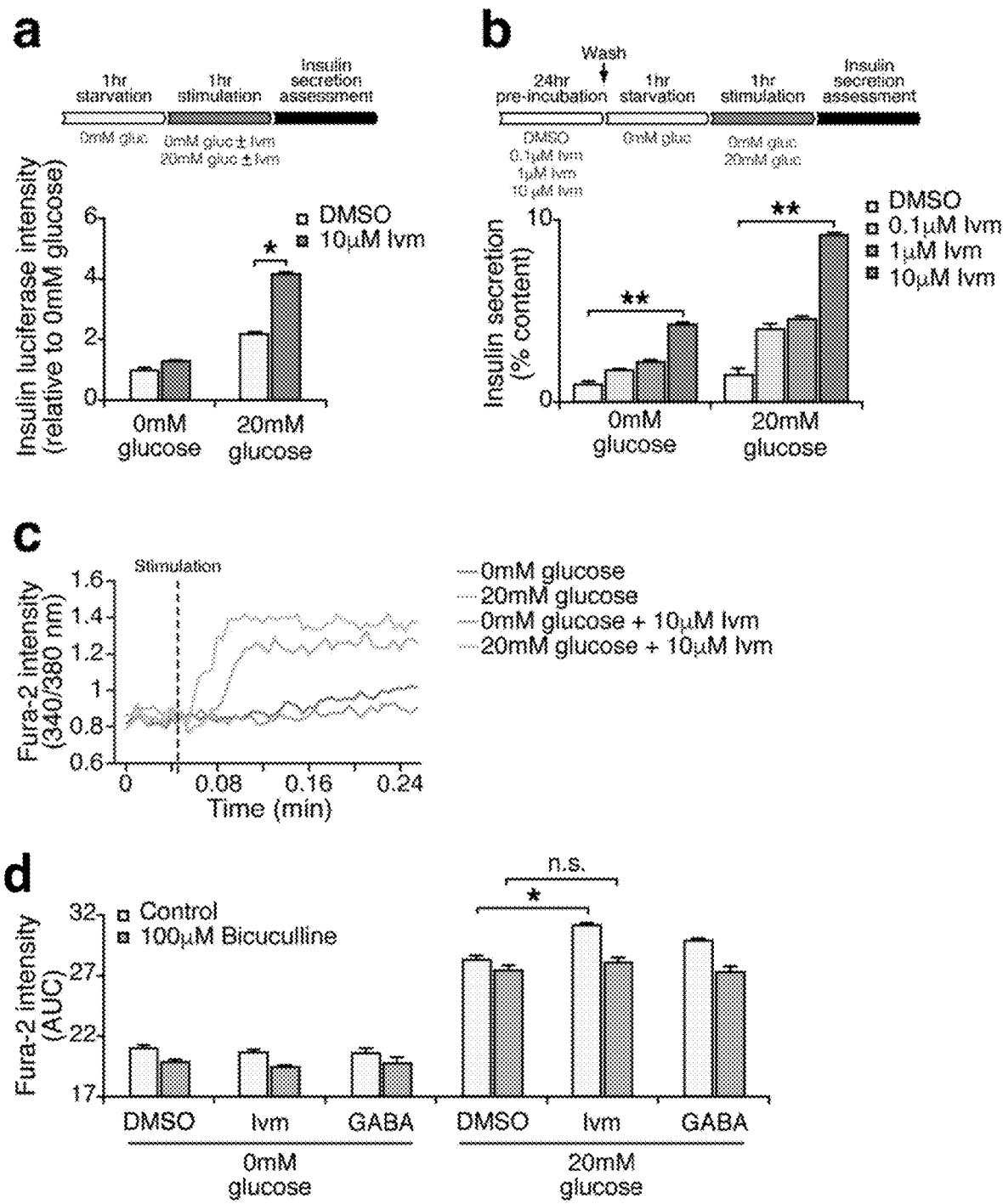
FIG. 28 shows that ivermectin enhances glucose-stimulated insulin secretion and calcium flux in wild-type βTC-6 cells. (Panels a-b) Glucose-stimulated insulin secretion in wild-type βTC-6 cells following either (Panel a) acute or (Panel b) prolonged exposure to ivermectin (IVM) at indicated concentrations in the presence or absence of glucose. (Panels c-d) Calcium flux in wild-type βTC-6 cells following exposure to glucose in the presence or absence of (Panel c) ivermectin (10 μM) or (Panel d) ivermectin (10 μM) and 100 uM Bicuculline, a GABAA receptor. *p<0.05, **p<0.01.

Chemogenetic Screen for Identification of Circadian Regulators of Insulin Secretion Impaired circadian function is associated with reduced insulin secretion in pancreatic β cells. Experiments were conducted during development of embodiments herein to identify small molecule and biologic agonists that restore the insulin secretory defects in the setting of circadian disruption. A high-throughput chemo-genetic screen was performed in Bmal1 null β cell lines established by CRISPR gene editing that also express an insulin nano-luciferase reporter (FIGS. 23-25). 23 "hit" compounds were identified which stimulate glucose-dependent insulin secretion in the absence of BMAL1 (FIG. 26). Hit compounds included both agonists of muscarinic GPCR signaling (carbachol and mecamylamine hydrochloride), which were previously found to enhance insulin secretion in Bmal1 cells, and a variety of novel insulinotropic molecules (e.g., ivermectin, alexidine hydrochlodire, and tomatine) that impact both glucose-stimulated insulin secretion and calcium flux (FIGS. 27-28). These cell-based experiments exploit new methodologies to identify compounds that augment insulin secretion following circadian disruption and open new opportunities to improve islet function and enhance glucose control in patients with circadian-related metabolic disorders such as diabetes mellitus.

Cell Culture

Beta TC-6 cells were obtained from ATCC (CRL-11506). Cells were cultured in Dulbecco's Modified Eagle's Medium (Corning, Cat #10-013-CV) supplemented with 15% fetal bovine serum (Corning, Cat #35-011-CV), 1% penicillin-streptomycin (Corning, Cat #30-002-CI), and 1% L-glutamine (Life Technologies, Cat #25030081) at 37° C. with 5% CO2. Culture medium was exchanged every 2-3 days.

Generation of CRISPR-CAS9 Plasmids Targeting Mouse Bmal1 and Clock (Related to FIG. 23)

For Bmal1: Exon 8 of the mouse Bmal1 gene was targeted by designing RNA guides (sgRNAs) using the Zhang lab CRISPR design tool (crispr.mit.edu). Exon 8 in BMAL1 encodes the basic-helix-loop-helix (bHLH) DNA binding domain and is the exon targeted in pancreas-specific Cre-LoxP-mediated knockout models with hypoinsulinemia and diabetes. Uniqueness of these sequences were confirmed by alignment to the mouse genome, reducing the likelihood of targeting off-target templates. Additionally, since the CAS9 nuclease requires recognition of a Protospacer Adjacent Motif (PAM) consensus sequence (5'-NGG-3') to cleave DNA, the CACC and AAAC nucleotide sequences were added to the 5' end of the forward targeting sgRNA oligos or the reverse complement of the sgRNA oligos, respectively, for cloning into the pSpCas9(BB)-2A-Puro vector (Addgene plasmid #48139, deposited by Feng Zhang) using the BbsI restriction enzyme. The sgRNA oligo sequences targeting Bmal1 exon 8 were as follows: 5' forward targeting sequence: CACCGCTGGACATTGCATTGCATGT (SEQ ID NO: 13); 5' reverse complement: AAACACATGCAATGCAATGTCCAGC (SEQ ID NO: 14); 3' forward targeting sequence: CACCGTAGATAAACTCACCGTGCTA (SEQ ID NO: 15); 3' reverse complement: AAACTAGCACGGTGAGTTTATCTAC (SEQ ID NO: 16).

To enable stable selection of Beta TC-6 clones with constitutively disrupted BMAL1 expression, a homology-directed repair (HDR) template (Bmal1-HDR plasmid) encoding a fluorescent marker (mCherry) and selectable marker (neomycin resistance) was designed that for insertion into the region in exon 8 cleaved by the CAS9 endonuclease. A double-stranded DNA oligo was synthesized encoding both an mCherry reporter and neomycin resistance cassette flanked by 1 kb of the complimentary sequence homologous to Bmal1 exon 8 surrounding the PAM sequence recognized by the sgRNAs. To generate this plasmid, a neomycin resistance cassette (pcDNA3.1, Invitrogen) was first cloned into the Topo cloning site of PCR2.1-TOPO vector (pCR2.1-TOPO, Invitrogen). Then, the IRES-mCherry sequence (pMSCV-IRES-mCherry, Addgene plasmid #52114, deposited by Dario Vignali) was cloned into the BstB1 site located between neomycin resistance cDNA and its terminator. Finally, 1 kb sequences homologous to the 5' and 3' sequences surrounding the CAS9 targeted-region in Bmal1 exon 8 were isolated from mouse genomic DNA and cloned into the PCR2.1-TOPO vector using Hind3/Spe1 sites for the 5' homologous sequence and Xho1/Xba1 sites for 3' homologous sequence, respectively. The two sgRNA oligos were annealed to form double stranded DNA and cloned into the pSpCas9(BB)-2A-Puro plasmid encoding the CRISPR-CAS9 nuclease using the BbsI restriction enzyme.

For Clock: Clock CRISPR/Cas9 KO plasmid (sc-419693) and Clock HDR plasmid (sc-419693-HDR) were obtained from Santa Cruz Biotechnology. The Clock CRISPR/Cas9 KO plasmid consists of a pool of 3 plasmids, each encoding the Cas9 nuclease and a target-specific 20 nt guide RNA (gRNA). The sgRNA oligo sequences targeting Clock were as follows: 5' forward targeting sequence: TCCATCTTTCTCGCGTTACC (SEQ ID NO: 17) for a target of exon 6; 5' forward targeting sequence: TCCTGGTAACGCGAGAAAGA (SEQ ID NO: 18) for a target of exon 6; and 5' forward targeting sequence: AGATGCTAGTGAGATTCGAC (SEQ ID NO: 19) for a target of exon 7. The Clock HDR plasmid consists of a pool of plasmids, each containing a homology-directed DNA repair template corresponding to the cut sites generated by the Clock CRISPR/Cas9 KO plasmid. Each HDR template contains two 800 bp homology arms designed to specifically bind to the genomic DNA surrounding the corresponding Cas9-induced double-strand DNA break site. The HDR plasmid also incorporates an antibiotic resistance gene (puromycin) for selection of cells containing a successful CRISPR/Cas9 double strand break.

Transfection of CRISPR-CAS9 Plasmids and Stable Selection of Bmal1$^{-/-}$ and Clock$^{-/-}$ Cells (Related to FIG. 23)

Beta TC-6 cells (passages 25-30) were plated into 6-well plates (Corning, Cat #353046) and cultured overnight. For Bmal1: The pSpCas9 vector containing sgRNAs (400 ng) and the Bmal1-HDR vector (600 ng) were transfected into Beta TC-6 cells by Lipofectamine 2000 (Thermo Fisher Scientific, Cat #11668027). After 48 hrs of transfection, the cells were treated with 500 µg/ml of G418 Sulfate (Corning, Cat #30-234-CR) to select for neomycin resistant clones for 14 days. After G418 selection, more than 10 single colonies were hand-picked and cultured individually in 96 well plates (Corning, Cat #3603). RNA and protein were extracted from these colonies and Bmal1 expression was assessed by qPCR and Western blot. For Clock: The Clock CRISPR/Cas9 KO Plasmid (1 µg) and Clock HDR Plasmid (1 µg) were transfected into Beta TC-6 cells by Lipofectamine 2000 (Thermo Fisher Scientific, Cat #11668027). After 48 hrs of transfection, the cells were treated with 2 µg/ml of puromycin (Sigma-Aldrich, Cat # P8833) to select for puromycin resistant clones for 14 days. After puromycin selection, more than 10 single colonies were hand-picked and cultured individually in 96 well plates (Corning, Cat #3603). RNA and protein were extracted and Clock expression was assessed by qPCR and Western blot.

Generation of Bmal1$^{-/-}$ Beta TC-6 Cells Stably Expressing Insulin Nanoluc (Related to FIG. 24)

The Insulin Nanoluc plasmid (David Altshuler, Addgene plasmid #62057) was used to provide a low cost, scalable, and rapid method to detect insulin secretion. The gene encoding Nano luciferase was cloned into the C-peptide portion of mouse proinsulin such that cleavage within insulin vesicles by pH-sensitive prohormone convertase results in the co-secretion of Nanoluc with endogenous insulin in a stimulus-dependent manner. The pLX304 lentivirus packaging plasmid containing the Proinsulin-NanoLuc construct was transfected into HEK293T (ATCC CRL-11268) cells with pCMV-VSVG (envelope vector) and 8.91 (packaging vector) (obtained from Jeff Milbrandt, Washington University in St. Louis). Supernatant containing lentivirus particles was harvested 48 hrs after transfection. Beta TC-6 cells were infected with Insulin-NanoLuc lentivirus, and stably expressing cells were selected by treating with puromycin (2 μg/ml, 2 days).

High-Throughput Screen for Drugs to Restore Insulin Secretion in Bmal1$^{-/-}$ Beta Cells and Insulin Secretion Assays (Related to FIG. 25):

The Spectrum Collection small molecule compound library (MicroSource Discovery Systems, Inc), which consists of 2700 known drugs and drug-like molecules, was screened for compounds that augment insulin secretion in Bmal1$^{-/-}$ Beta TC-6 cells. Insulin Nanoluc-expressing Bmal1$^{-/-}$ Beta TC-6 cells (30,000 cells/well) were placed into 384 well plates and cultured for 4 days at 37° C. and 5% CO2. The cells were washed once and starved in KRB buffer containing 0 mM glucose for 1 hr. After removing the KRB, KRB buffer containing 20 mM glucose in addition to the small molecules (10 uM) were added, and the cells were incubated for 1 hr. As a negative control, 16 wells received KRB buffer with only 20 mM glucose, which fails to elicit insulin secretion in Bmal1$^{-/-}$ cells, and as a positive control, 16 wells received KRB buffer containing 20 mM glucose and 10 μM PMA, which is known to induce insulin secretion in both Bmal1$^{-/-}$ mouse islets and Beta TC-6 cells. After 1 hr, the supernatant was collected and centrifuged at 500 g for 30 min. The supernatant was transferred into a fresh 384-well assay plate containing Nano-Glo Luciferase Assay Substrate (Promega), and luciferase intensity was measured by EnSpire Plate Reader (PerkinElmer) within 30 minutes.

Determination of Hit Compounds (Related to FIG. 26)

Z scores for luciferase intensities produced by screened compounds were calculated from the following formula: $z=(X-\mu)/\sigma$ (where z is the Z score, X is the intensity of the compounds, μ is the intensity of negative control (20 mM glucose), and σ is the standard deviation of negative control). A row-based correction factor was applied to all luciferase readings to adjust for logarithmic signal decay. Hit compounds were defined as those that elicited a response of greater than 3 standard deviations from the mean (Z score>3) and more than 1.2-fold increase compared to negative control.

Insulin Secretion Assays in Beta TC-6 Cells (Related to FIGS. 27-28)

Beta TC-6 cells (300,000 cells/well) were seeded into poly-L-lysine-coated 24 well plates and cultured for 48-72 hrs at 37° C. and 5% CO2. The cells were washed once and incubated in KRB buffer containing 0 mM glucose for 1 hr. Cells were then treated for 1 hr with KRB buffer containing 0 or 20 mM glucose in the presence of hit compounds (including ivermectin, alexidine, and tomatine at final concentrations of 10 and 100 μM) or an equivalent volume of DMSO as a vehicle control. Supernatants were then collected and centrifuged at 500G for 30 min and assayed for insulin content by ELISA (Crystal Chem Inc). Cell lysates were harvested in acid-ethanol solution (0.18M HCl in 70% Ethanol), sonicated, and solubilized overnight at 4° C. before assaying total insulin content by ELISA. For insulin secretion assays following prolonged ivermectin treatment, cells were first treated with 10 μm ivermectin for 24 hrs prior to the 1 hr incubation with 0 mM glucose KRB buffer.

Insulin Secretion Assays in Isolated Islets (Confirmation of Hit Compounds) (Related to FIG. 27)

Mouse pancreatic islets were isolated via bile duct collagenase digestion (Collagenase P, Sigma) and Ficoll gradient separation and left to recover overnight (16 hrs) at 37° C. in RPMI 1640 with 10% FBS, 1% L-glutamine, and 1% penicillin/streptomycin. For insulin release assays, 5 islets were statically incubated in Krebs-Ringer Buffer (KRB) and stimulated for 1 hr at 37° C. with 2 or 20 mM glucose in the presence or absence of 10 μM ivermectin. Supernatant was collected and assayed for insulin content by ELISA (Crystal Chem Inc). Islets were then sonicated in acid-ethanol solution and solubilized overnight at 4° C. before assaying total insulin content by ELISA.

Figure 29:
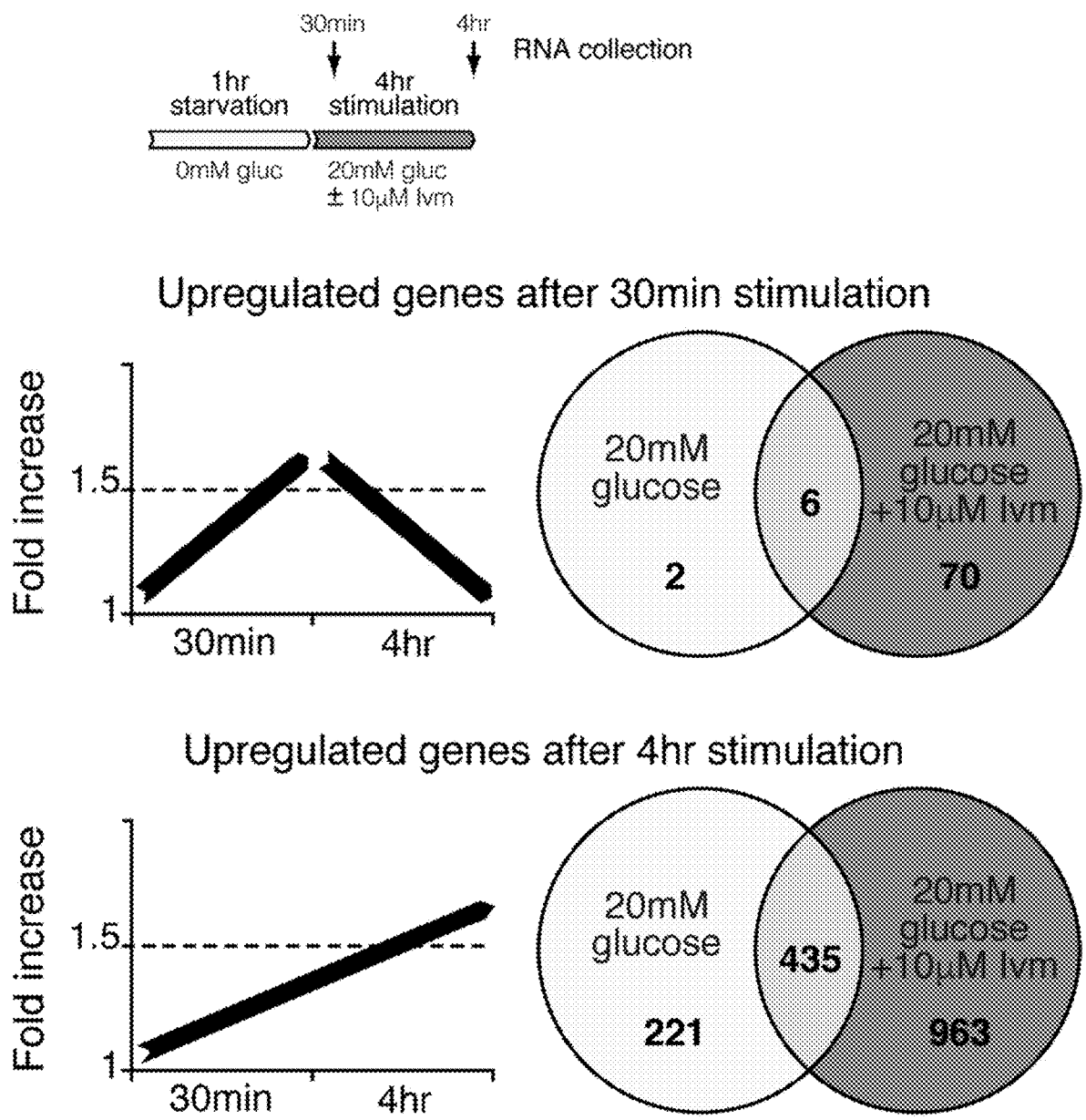
FIG. 29 shows induction of unique gene sets following acute vs longer-term treatment of βTC-6 cells with ivermectin. Schematic on top shows RNA collection occurs either 30 min or 4 hrs post-ivermectin treatment with glucose. RNA-sequencing was performed, and Venn diagrams show the number of genes upregulated in both conditions that are unique to IVM (orange). GO analysis indicates genes upregulated after 30 min include those involved in pancreatic cell proliferation (Nr4a1, Nr4a3, Cebpb), while those upregulated after 4 hrs are enriched for tyrosine kinase signaling pathway members (Bmpr2, Igf1r, Cav1).

RNA Isolation and qPCR mRNA Quantification (Related to FIGS. 23 and 29)

RNA was extracted from Beta TC-6 cells using the Tri Reagent (Molecular Research Center, Inc) and frozen at −80° C. RNA was isolated according to the manufacturer's protocol and purified using Quick-RNA™ MiniPrep (ZYMO RESEARCH). cDNAs were then synthesized using the High Capacity cDNA Reverse Transcription Kit (Applied Biosystems). Quantitative real-time PCR analysis was performed with SYBR Green Master Mix (Applied Biosystems) and analyzed using a Touch™ CFX384 Real-Time PCR Detection System (Bio-Rad). Relative expression levels were determined using the comparative CT method to normalize target gene mRNA to Gapdh. Primer sequences for qPCR as follows: Gapdh Forward: 5'-ATCGCAAGAG-GAAAGGCAGT-3'(SEQ ID NO: 2), Reverse: 5'-ATCCTTCCTTGGTGTTCTGCAT-3 (SEQ ID NO: 3); Chop Forward: 5'-CCACCACACCTGAAAGCAGAA-3' (SEQ ID NO: 20), Reverse: 5'-AGGT-GAAAGGCAGGGACTCA-3 (SEQ ID NO: 21); Atf3 Forward: 5'-GCTGGAGTCAGTTACCGTCAA-3' (SEQ ID NO: 22), Reverse: 5'-ATGTGTTGCAGAACGCACCT-3 (SEQ ID NO: 23); Nr4a2 Forward: 5'-CACGCGAGTGTTCTTTTCCG-3' (SEQ ID NO: 24), Reverse: 5'-AAGTCCGTGGTGATGCTACG-3 (SEQ ID NO: 25).

RNA-Sequencing and Analysis (Related to FIG. 29)

Following RNA isolation (described above), RNA quality was assessed using a Bioanalyzer (Agilent), and sequencing libraries were constructed using a NEBNext® Ultra™ Directional RNA Library Prep Kit for Illumina (New England BioLabs, E7420L) according to the manufacturer's instructions. Libraries were quantified using both a Bioanalyzer (Agilent) and NEBNext® Library Quant Kit for Illumina (New England BioLabs, E7630L) and sequenced on either an Illumina NextSeq 500 instrument to a depth of at least 10 million reads using 75 bp paired-end reads. For differential expression analysis, RNA raw sequence reads were aligned to the reference genome (mm10) using STAR version 2.3.1s_r366 and transcripts were counted using the featureCounts function within the R package subRead version 1.5.1. Differentially expressed RNAs were identified using DESeq2 version 1.6.3. (FDR-adjusted p-value<0.05). For gene ontology enrichment analysis, deferential expressed gene list were assessed with Metascape 1.0 (http://metascape.org).

Intracellular Calcium Determination (Related to FIGS. 27-28)

BetaTC-6 cells were plated at a density of 100,000 cells per well in black 96-well plates with clear bottoms and cultured overnight at 37° C. and 5% CO2. Cells were then washed with BSA-free KRB buffer with no glucose and loaded with 5 μM Fura-2 (Invitrogen) and 0.04% Pluronic F-127 (Invitrogen) for 30 min at 37° C. Following a wash with BSA-free KRB, Fura-2 intensity was measured following injection of either glucose alone or indicated compounds. Cells were alternately excited with 340 nm and 380 nm wavelength light, and the emitted light was detected at 510 nm using a Cytation 3 Cell Imaging Multi-Mode Reader (Bio Tek) at sequential 30-second intervals. Raw fluorescence data were exported to Microsoft Excel and expressed as the 340/380 ratio for each well.

Protein Gel Electrophoresis and Immunoblotting (FIG. 23)

Beta TC-6 cells lysates were prepared in CelLytic™ MT Mammalian Tissue Lysis Reagent (Sigma) supplemented with protease inhibitors. Protein levels were quantified using DC Protein Assay (Bio-Rad), and protein extracts were subject to SDS-PAGE gel electrophoresis and transferred to nitrocellulose membranes (GE Healthcare). Primary antibodies used were anti-BMAL1 (Santa Cruz Biotechnology, sc-48790), anti-CLOCK (Santa Cruz Biotechnology, sc-25361) and anti-β-ACTIN (Cell Signaling).

REFERENCES

The following references, some of which are cited above, are incorporated by reference in their entireties.

N. Preitner, F. Damiola, L. Lopez-Molina, J. Zakany, D. Duboule, U. Albrecht, U. Schibler, The orphan nuclear receptor REV-ERBα controls circadian transcription within the positive limb of the mammalian circadian oscillator. Cell 110, 251-260 (2002). doi:10.1016/S0092-8674(02)00825-5 pmid:12150932

I. Zamir, H. P. Harding, G. B. Atkins, A. Hörlein, C. K. Glass, M. G. Rosenfeld, M. A. Lazar, A nuclear hormone receptor corepressor mediates transcriptional silencing by receptors with distinct repression domains. Mol. Cell. Biol. 16, 5458-5465 (1996). doi:10.1128/MCB.16.10.5458 pmid:8816459

A. Balsalobre, F. Damiola, U. Schibler, A serum shock induces circadian gene expression in mammalian tissue culture cells. Cell 93, 929-937 (1998). doi:10.1016/S0092-8674(00)81199-X pmid:9635423

F. W. Turek, C. Joshu, A. Kohsaka, E. Lin, G. Ivanova, E. McDearmon, A. Laposky, A. Losee-Olson, A. Easton, D. R. Jensen, R. H. Eckel, J. S. Takahashi, J. Bass, Obesity and metabolic syndrome in circadian Clock mutant mice. Science 308, 1043-1045 (2005). doi:10.1126/science.1108750 pmid:15845877

K. A. Lamia, K. F. Storch, C. J. Weitz, Physiological significance of a peripheral tissue circadian clock. Proc. Natl. Acad. Sci. U.S.A. 105, 15172-15177 (2008). doi:10.1073/pnas.0806717105 pmid:18779586

B. Marcheva, K. M. Ramsey, E. D. Buhr, Y. Kobayashi, H. Su, C. H. Ko, G. Ivanova, C. Omura, S. Mo, M. H. Vitaterna, J. P. Lopez, L. H. Philipson, C. A. Bradfield, S. D. Crosby, L. JeBailey, X. Wang, J. S. Takahashi, J. Bass, Disruption of the clock components CLOCK and BMAL1 leads to hypoinsulinaemia and diabetes. Nature 466, 627-631 (2010). doi:10.1038/nature09253 pmid:20562852

L. A. Sadacca, K. A. Lamia, A. S. deLemos, B. Blum, C. J. Weitz, An intrinsic circadian clock of the pancreas is required for normal insulin release and glucose homeostasis in mice. Diabetologia 54, 120-124 (2011). doi:10.1007/s00125-010-1920-8 pmid:20890745

C. B. Peek, A. H. Affinati, K. M. Ramsey, H. Y. Kuo, W. Yu, L. A. Sena, O. Ilkayeva, B. Marcheva, Y. Kobayashi, C. Omura, D. C. Levine, D. J. Bacsik, D. Gius, C. B. Newgard, E. Goetzman, N. S. Chandel, J. M. Denu, M. Mrksich, J. Bass, Circadian clock NAD+ cycle drives mitochondrial oxidative metabolism in mice. Science 342, 1243417 (2013). doi:10.1126/science.1243417 pmid:24051248

N. Koike, S. H. Yoo, H. C. Huang, V. Kumar, C. Lee, T. K. Kim, J. S. Takahashi, Transcriptional architecture and chromatin landscape of the core circadian clock in mammals. Science 338, 349-354 (2012). doi:10.1126/science.1226339 pmid:22936566

B. Fang, L. J. Everett, J. Jager, E. Briggs, S. M. Armour, D. Feng, A. Roy, Z. Gerhart-Hines, Z. Sun, M. A. Lazar, Circadian enhancers coordinate multiple phases of rhythmic gene transcription in vivo. Cell 159, 1140-1152 (2014). doi:10.1016/j.cell.2014.10.022 pmid:25416951

J. S. Menet, J. Rodriguez, K. C. Abruzzi, M. Rosbash, Nascent-Seq reveals novel features of mouse circadian transcriptional regulation. eLife 1, e00011 (2012). pmid:23150795

S. H. Yoo, S. Yamazaki, P. L. Lowrey, K. Shimomura, C. H. Ko, E. D. Buhr, S. M. Siepka, H. K. Hong, W. J. Oh, O. J. Yoo, M. Menaker, J. S. Takahashi, PERIOD2:LUCIFERASE real-time reporting of circadian dynamics reveals persistent circadian oscillations in mouse peripheral tissues. Proc. Natl. Acad. Sci. U.S.A. 101, 5339-5346 (2004). pmid:14963227

J. S. O'Neill, E. S. Maywood, J. E. Chesham, J. S. Takahashi, M. H. Hastings, cAMP-dependent signaling as a core component of the mammalian circadian pacemaker. Science 320, 949-953 (2008). doi:10.1126/science.1152506 pmid:18487196

A. L. Hutchison, M. Maienschein-Cline, A. H. Chiang, S. M. Tabei, H. Gudjonson, N. Bahroos, R. Allada, A. R. Dinner, Improved statistical methods enable greater sensitivity in rhythm detection for genome-wide data. PLOS Comput. Biol. 11, e1004094 (2015). doi:10.1371/journal.pcbi.1004094 pmid:25793520

H. R. Ueda, S. Hayashi, W. Chen, M. Sano, M. Machida, Y. Shigeyoshi, M. Iino, S. Hashimoto, System-level identification of transcriptional circuits underlying mammalian circadian clocks. Nat. Genet. 37, 187-192 (2005). doi:10.1038/ng1504 pmid:15665827

X. W. Chen, H. Wang, K. Bajaj, P. Zhang, Z. X. Meng, D. Ma, Y. Bai, H. H. Liu, E. Adams, A. Baines, G. Yu, M. A. Sartor, B. Zhang, Z. Yi, J. Lin, S. G. Young, R. Schekman, D. Ginsburg, SEC24A deficiency lowers plasma cholesterol through reduced PCSK9 secretion. eLife 2, e00444 (2013). doi:10.7554/eLife.00444 pmid:23580231

A. J. Noble, Q. Zhang, J. O'Donnell, H. Hariri, N. Bhattacharya, A. G. Marshall, S. M. Stagg, A pseudoatomic model of the COPII cage obtained from cryo-electron microscopy and mass spectrometry. Nat. Struct. Mol. Biol. 20, 167-173 (2013). doi:10.1038/nsmb.2467 pmid:23262493

Z. Wang, D. C. Thurmond, Mechanisms of biphasic insulin-granule exocytosis—roles of the cytoskeleton, small GTPases and SNARE proteins. J. Cell Sci. 122, 893-903 (2009). doi:10.1242/jcs.034355 pmid:19295123

Y. Liu, Y. Sugiura, W. Lin, The role of synaptobrevin1/VAMP1 in Ca2+-triggered neurotransmitter release at the mouse neuromuscular junction. J. Physiol. 589, 1603-1618 (2011). doi:10.1113/jphysiol.2010.201939 pmid:21282288

M. Ohara-Imaizumi, C. Nishiwaki, Y. Nakamichi, T. Kikuta, S. Nagai, S. Nagamatsu, Correlation of syntaxin-1 and SNAP-25 clusters with docking and fusion of insulin granules analysed by total internal reflection fluorescence microscopy. Diabetologia 47, 2200-2207 (2004). doi:10.1007/s00125-004-1579-0 pmid:15647897

K. Fujimoto, T. Shibasaki, N. Yokoi, Y. Kashima, M. Matsumoto, T. Sasaki, N. Tajima, T. Iwanaga, S. Seino, Piccolo, a Ca2+ sensor in pancreatic beta-cells. Involvement of cAMP-GEFII.Rim2. Piccolo complex in cAMP-dependent exocytosis. J. Biol. Chem. 277, 50497-50502 (2002). doi:10.1074/jbc.M210146200 pmid:12401793

H. Takahashi, T. Shibasaki, J. H. Park, S. Hidaka, T. Takahashi, A. Ono, D. K. Song, S. Seino, Role of Epac2A/Rap1 signaling in interplay between incretin and sulfonylurea in insulin secretion. Diabetes 64, 1262-1272 (2015). pmid:25315008

M. Fukuda, Molecular cloning, expression, and characterization of a novel class of synaptotagmin (Syt XIV) conserved from *Drosophila* to humans. J. Biochem. 133, 641-649 (2003). doi:10.1093/jb/mvg082 pmid:12801916

A. Milochau, V. Lagrée, M. N. Benassy, S. Chaignepain, J. Papin, I. Garcia-Arcos, A. Lajoix, C. Monterrat, L. Coudert, J. M. Schmitter, B. Ochoa, J. Lang, Synaptotagmin 11 interacts with components of the RNA-induced silencing complex RISC in clonal pancreatic β-cells. FEBS Lett. 588, 2217-2222 (2014). pmid:24882364

R. A. Easom, CaM kinase II: A protein kinase with extraordinary talents germane to insulin exocytosis. Diabetes 48, 675-684 (1999). doi:10.2337/diabetes.48.4.675 pmid: 10102681

T. J. Biden, C. Schmitz-Peiffer, J. G. Burchfield, E. Gurisik, J. Cantley, C. J. Mitchell, L. Carpenter, The diverse roles of protein kinase C in pancreatic beta-cell function. Biochem. Soc. Trans. 36, 916-919 (2008). doi:10.1042/B5T0360916 pmid:18793161

X. Zhang, K. Orlando, B. He, F. Xi, J. Zhang, A. Zajac, W. Guo, Membrane association and functional regulation of Sec3 by phospholipids and Cdc42. J. Cell Biol. 180, 145-158 (2008). doi:10.1083/jcb.200704128 pmid: 18195105

G. Jedd, J. Mulholland, N. Segev, Two new Ypt GTPases are required for exit from the yeast trans-Golgi compartment. J. Cell Biol. 137, 563-580 (1997). doi:10.1083/jcb.137.3.563 pmid:9151665

P. Pulimeno, T. Mannic, D. Sage, L. Giovannoni, P. Salmon, S. Lemeille, M. Giry-Laterriere, M. Unser, D. Bosco, C. Bauer, J. Morf, P. Halban, J. Philippe, C. Dibner, Autonomous and self-sustained circadian oscillators displayed in human islet cells. Diabetologia 56, 497-507 (2013). doi: 10.1007/s00125-012-2779-7 pmid:23242133

C. Benner, T. van der Meulen, E. Cacéres, K. Tigyi, C. J. Donaldson, M. O. Huising, The transcriptional landscape of mouse beta cells compared to human beta cells reveals notable species differences in long non-coding RNA and protein-coding gene expression. BMC Genomics 15, 620 (2014). doi:10.1186/1471-2164-15-620 pmid:25051960

L. Pasquali, K. J. Gaulton, S. A. Rodriguez-Segui, L. Mularoni, I. Miguel-Escalada, I. Akerman, J. J. Tena, I. Morán, C. Gómez-Marín, M. van de Bunt, J. Ponsa-Cobas, N. Castro, T. Nammo, I. Cebola, J. García-Hurtado, M. A. Maestro, F. Pattou, L. Piemonti, T. Berney, A. L. Gloyn, P. Ravassard, J. L. Gómez-Skarmeta, F. Müllner, M. I. McCarthy, J. Ferrer, Pancreatic islet enhancer clusters enriched in type 2 diabetes risk-associated variants. Nat. Genet. 46, 136-143 (2014). doi:10.1038/ng.2870 pmid: 24413736

M. P. Creyghton, A. W. Cheng, G. G. Welstead, T. Kooistra, B. W. Carey, E. J. Steine, J. Hanna, M. A. Lodato, G. M. Frampton, P. A. Sharp, L. A. Boyer, R. A. Young, R. Jaenisch, Histone H3K27ac separates active from poised enhancers and predicts developmental state. Proc. Natl. Acad. Sci. U.S.A. 107, 21931-21936 (2010). doi:10.1073/pnas.1016071107 pmid:21106759

H. H. He, C. A. Meyer, H. Shin, S. T. Bailey, G. Wei, Q. Wang, Y. Zhang, K. Xu, M. Ni, M. Lupien, P. Mieczkowski, J. D. Lieb, K. Zhao, M. Brown, X. S. Liu, Nucleosome dynamics define transcriptional enhancers. Nat. Genet. 42, 343-347 (2010). doi:10.1038/ng.545 pmid:20208536

G. Rey, F. Cesbron, J. Rougemont, H. Reinke, M. Brunner, F. Naef, Genome-wide and phase-specific DNA-binding rhythms of BMAL1 control circadian output functions in mouse liver. PLOS Biol. 9, e1000595 (2011). doi: 10.1371/journal.pbio.1000595 pmid:21364973

N. D. Heintzman, R. K. Stuart, G. Hon, Y. Fu, C. W. Ching, R. D. Hawkins, L. O. Barrera, S. Van Calcar, C. Qu, K. A. Ching, W. Wang, Z. Weng, R. D. Green, G. E. Crawford, B. Ren, Distinct and predictive chromatin signatures of transcriptional promoters and enhancers in the human genome. Nat. Genet. 39, 311-318 (2007). doi:10.1038/ng1966 pmid:17277777

S. J. Cooper, N. D. Trinklein, E. D. Anton, L. Nguyen, R. M. Myers, Comprehensive analysis of transcriptional promoter structure and function in 1% of the human genome. Genome Res. 16, 1-10 (2006). doi:10.1101/gr.4222606 pmid:16344566

P. Carninci, A. Sandelin, B. Lenhard, S. Katayama, K. Shimokawa, J. Ponjavic, C. A. Semple, M. S. Taylor, P. G. Engström, M. C. Frith, A. R. Forrest, W. B. Alkema, S. L. Tan, C. Plessy, R. Kodzius, T. Ravasi, T. Kasukawa, S. Fukuda, M. Kanamori-Katayama, Y. Kitazume, H. Kawaji, C. Kai, M. Nakamura, H. Konno, K. Nakano, S. Mottagui-Tabar, P. Arner, A. Chesi, S. Gustincich, F. Persichetti, H. Suzuki, S. M. Grimmond, C. A. Wells, V. Orlando, C. Wahlestedt, E. T. Liu, M. Harbers, J. Kawai, V. B. Bajic, D. A. Hume, Y. Hayashizaki, Genome-wide analysis of mammalian promoter architecture and evolution. Nat. Genet. 38, 626-635 (2006). doi:10.1038/ng1789 pmid:16645617

C. Vollmers, R. J. Schmitz, J. Nathanson, G. Yeo, J. R. Ecker, S. Panda, Circadian oscillations of protein-coding and regulatory RNAs in a highly dynamic mammalian liver epigenome. Cell Metab. 16, 833-845 (2012). doi: 10.1016/j.cmet.2012.11.004 pmid:23217262

D. A. Stoffers, N. T. Zinkin, V. Stanojevic, W. L. Clarke, J. F. Habener, Pancreatic agenesis attributable to a single nucleotide deletion in the human IPF1 gene coding sequence. Nat. Genet. 15, 106-110 (1997). doi:10.1038/ng0197-106 pmid:8988180

B. G. Hoffman, G. Robertson, B. Zavaglia, M. Beach, R. Cullum, S. Lee, G. Soukhatcheva, L. Li, E. D. Wederell, N. Thiessen, M. Bilenky, T. Cezard, A. Tam, B. Kamoh, I. Birol, D. Dai, Y. Zhao, M. Hirst, C. B. Verchere, C. D. Helgason, M. A. Marra, S. J. Jones, P. A. Hoodless, Locus co-occupancy, nucleosome positioning, and H3K4me1 regulate the functionality of FOXA2-, HNF4A-, and PDX1-bound loci in islets and liver. Genome Res. 20, 1037-1051 (2010). doi:10.1101/gr.104356.109 pmid: 20551221

C. Gu, G. H. Stein, N. Pan, S. Goebbels, H. Hornberg, K. A. Nave, P. Herrera, P. White, K. H. Kaestner, L. Sussel, J. E. Lee, Pancreatic beta cells require NeuroD to achieve and maintain functional maturity. Cell Metab. 11, 298-310 (2010). doi:10.1016/j.cmet.2010.03.006 pmid:20374962

L. Kang, Z. He, P. Xu, J. Fan, A. Betz, N. Brose, T. Xu, Munc13-1 is required for the sustained release of insulin from pancreatic beta cells. Cell Metab. 3, 463-468 (2006). doi:10.1016/j.cmet.2006.04.012 pmid:16697276

O. Gen, ç O. Kochubey, R. F. Toonen, M. Verhage, R. Schneggenburger, Munc18-1 is a dynamically regulated PKC target during short-term enhancement of transmitter release. eLife 3, e01715 (2014). doi:10.7554/eLife.01715 pmid:24520164

C. J. Morris, J. N. Yang, J. I. Garcia, S. Myers, I. Bozzi, W. Wang, O. M. Buxton, S. A. Shea, F. A. Scheer, Endogenous circadian system and circadian misalignment impact glucose tolerance via separate mechanisms in humans. Proc. Natl. Acad. Sci. U.S.A. 112, E2225-E2234 (2015). doi:10.1073/pnas.1418955112 pmid:25870289

O. M. Buxton, S. W. Cain, S. P. O'Connor, J. H. Porter, J. F. Duffy, W. Wang, C. A. Czeisler, S. A. Shea, Adverse metabolic consequences in humans of prolonged sleep restriction combined with circadian disruption. Sci. Transl. Med. 4, 129ra43 (2012). pmid:22496545

A. Bonnefond, N. Clement, K. Fawcett, L. Yengo, E. Vaillant, J. L. Guillaume, A. Dechaume, F. Payne, R. Roussel, S. Czernichow, S. Hercberg, S. Hadjadj, B. Balkau, M. Mane, O. Lantieri, C. Langenberg, N. Bouatia-Naji, G. Charpentier, M. Vaxillaire, G. Rocheleau, N. J. Wareham, R. Sladek, M. I. McCarthy, C. Dina, I. Barroso, R. Jockers, P. Froguel, Rare MTNR1B variants impairing melatonin receptor 1B function contribute to type 2 diabetes. Nat. Genet. 44, 297-301 (2012). doi:10.1038/ng.1053 pmid:22286214

B. P. Johnson et al., The hepatocyte circadian clock controls acetaminophen bioactivation through NADPH-cytochrome P450 oxidoreductase. Proc. Natl. Acad. Sci. U.S.A. 111, 18757-18762 (2014). doi:10.1073/pnas.1421708111 pmid:25512522

G. Gu, J. Dubauskaite, D. A. Melton, Direct evidence for the pancreatic lineage: NGN3+ cells are islet progenitors and are distinct from duct progenitors. Development 129, 2447-2457 (2002). pmid:11973276

A. Dobin, C. A. Davis, F. Schlesinger, J. Drenkow, C. Zaleski, S. Jha, P. Batut, M. Chaisson, T. R. Gingeras, STAR: Ultrafast universal RNA-seq aligner. Bioinformatics 29, 15-21 (2013). doi:10.1093/bioinformatics/bts635 pmid:23104886

M. I. Love, W. Huber, S. Anders, Moderated estimation of fold change and dispersion for RNA-seq data with DESeq2. Genome Biol. 15, 550 (2014). doi:10.1186/s13059-014-0550-8 pmid:25516281

M. Kanehisa, S. Goto, Y. Sato, M. Kawashima, M. Furumichi, M. Tanabe, Data, information, knowledge and principle: Back to metabolism in KEGG. Nucleic Acids Res. 42, D199-D205 (2014). doi:10.1093/nar/gkt1076 pmid:24214961

H. Ogata, S. Goto, K. Sato, W. Fujibuchi, H. Bono, M. Kanehisa, KEGG: Kyoto Encyclopedia of Genes and Genomes. Nucleic Acids Res. 27, 29-34 (1999). doi:10.1093/nar/27.1.29 pmid:9847135

S. Heinz, C. Benner, N. Spann, E. Bertolino, Y. C. Lin, P. Laslo, J. X. Cheng, C. Murre, H. Singh, C. K. Glass, Simple combinations of lineage-determining transcription factors prime cis-regulatory elements required for macrophage and B cell identities. Mol. Cell 38, 576-589 (2010). doi:10.1016/j.molcel.2010.05.004 pmid:20513432

B. Langmead, C. Trapnell, M. Pop, S. L. Salzberg, Ultrafast and memory-efficient alignment of short DNA sequences to the human genome. Genome Biol. 10, R25 (2009). doi:10.1186/gb-2009-10-3-r25 pmid:19261174

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A method of screening for compounds that alter oxygen consumption, comprising:
   a) contacting a plurality of myoblasts lacking a functional Bmal1 gene with a test compound; and
   b) measuring the level of oxygen consumption said myoblasts in the presence and absence of said test compound.

2. The method of claim 1, wherein test compounds that restore oxygen consumption are identified.

3. The method of claim 1, further comprising contacting said myoblasts with glucose.

4. The method of claim 1, wherein the myoblasts are immortalized or primary myoblasts.

* * * * *